US011975172B2

(12) United States Patent
Cowan et al.

(10) Patent No.: US 11,975,172 B2
(45) Date of Patent: *May 7, 2024

(54) FLUID INJECTOR WITH SYRINGE ENGAGEMENT MECHANISM

(71) Applicant: BAYER HEALTHCARE LLC, Whippany, NJ (US)

(72) Inventors: Kevin Cowan, Allison Park, PA (US); Michael Spohn, Fenelton, PA (US); Adam Steege, Durham, NC (US); Jessie Delgado, Durham, NC (US); Keith Lipford, Baltimore, MD (US); Chet Larrow, Baltimore, MD (US); Mariano Mumpower, Baltimore, MD (US); Danica Gordon, Baltimore, MD (US)

(73) Assignee: BAYER HEALTHCARE LLC, Whippany, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/554,265

(22) Filed: Dec. 17, 2021

(65) Prior Publication Data
US 2022/0105265 A1 Apr. 7, 2022

Related U.S. Application Data

(63) Continuation of application No. 16/341,205, filed as application No. PCT/US2017/056747 on Oct. 16, 2017, now Pat. No. 11,207,462.
(Continued)

(51) Int. Cl.
A61M 5/145 (2006.01)
A61M 5/00 (2006.01)
(Continued)

(52) U.S. Cl.
CPC ........ A61M 5/14586 (2013.01); A61M 5/007 (2013.01); A61M 5/1408 (2013.01);
(Continued)

(58) Field of Classification Search
CPC .......... A61M 5/14586; A61M 5/14566; A61M 5/14546; A61M 5/31515; A61M 5/2425; A61M 2005/14553; A61M 5/1458
See application file for complete search history.

(56) References Cited

U.S. PATENT DOCUMENTS 352,715 A 11/1886 Sandmark
798,093 A 8/1905 Edward
(Continued)

FOREIGN PATENT DOCUMENTS

EP 1086661 A2 3/2001
EP 2098258 A1 9/2009
(Continued)

OTHER PUBLICATIONS

"International Preliminary Report on Patentability from PCT Application No. PCT/US2017/056747", dated May 2, 2019.

Primary Examiner — William R Carpenter
Assistant Examiner — Robert F Allen
(74) Attorney, Agent, or Firm — David Schramm; Joseph L. Kent; James R. Stevenson

(57) ABSTRACT

An engagement mechanism associated with a reciprocally movable piston of a fluid injector is configured for releasably engaging an engagement portion at a proximal end of a rolling diaphragm syringe having a flexible sidewall configured for rolling upon itself when acted upon by the piston. The engagement mechanism has a plurality of engagement elements reversibly and radially movable relative to the engagement portion of the syringe between a first position, where the plurality of engagement elements are
(Continued)

disengaged from the engagement portion of the syringe, and a second position, where the plurality of engagement elements are engaged with the engagement portion of the syringe. The engagement mechanism further has a drive mechanism for moving the plurality of engagement elements between the first position and the second position.

20 Claims, 48 Drawing Sheets

Related U.S. Application Data

(60) Provisional application No. 62/545,728, filed on Aug. 15, 2017, provisional application No. 62/545,798, filed on Aug. 15, 2017, provisional application No. 62/545,693, filed on Aug. 15, 2017, provisional application No. 62/409,044, filed on Oct. 17, 2016, provisional application No. 62/409,039, filed on Oct. 17, 2016, provisional application No. 62/409,032, filed on Oct. 17, 2016.

(51) Int. Cl.
 *A61M 5/14* (2006.01)
 *A61M 5/24* (2006.01)
 *A61M 5/315* (2006.01)

(52) U.S. Cl.
 CPC .... *A61M 5/14546* (2013.01); *A61M 5/14566* (2013.01); *A61M 5/2425* (2013.01); *A61M 5/31515* (2013.01); *A61M 5/1458* (2013.01)

(56) References Cited

U.S. PATENT DOCUMENTS

| | | | |
|---|---|---|---|
| 937,029 A | 10/1909 | Blessing et al. | |
| 1,930,929 A | 10/1933 | Joel et al. | |
| 2,062,285 A | 12/1936 | Sam et al. | |
| 2,514,575 A | 7/1950 | Hein et al. | |
| 2,592,381 A | 4/1952 | Blackman | |
| 2,667,163 A | 1/1954 | Smith | |
| 2,667,164 A | 1/1954 | Smith | |
| 2,667,165 A | 1/1954 | Smith | |
| 2,667,872 A | 2/1954 | Smith | |
| 2,672,866 A | 3/1954 | Kater | |
| 2,673,561 A | 3/1954 | Peterson, Jr. | |
| 2,688,963 A | 9/1954 | Smith | |
| 2,688,964 A | 9/1954 | Smith | |
| 2,690,179 A | 9/1954 | Fox | |
| 2,717,598 A | 9/1955 | Krasno | |
| 2,805,662 A | 9/1957 | Lawshe et al. | |
| 2,911,972 A | 11/1959 | Elinger | |
| 2,935,067 A | 5/1960 | Bouet | |
| 2,950,717 A | 8/1960 | Bonet | |
| 3,155,281 A | 11/1964 | Stracey | |
| 3,161,194 A | 12/1964 | Chapman | |
| 3,161,195 A | 12/1964 | Taylor et al. | |
| 3,172,577 A | 3/1965 | Hartung | |
| 3,190,619 A | 6/1965 | Penney et al. | |
| 3,231,139 A | 1/1966 | Bouet | |
| 3,301,293 A | 1/1967 | Santelli | |
| 3,340,869 A | 9/1967 | Bane | |
| 3,353,537 A | 11/1967 | Knox et al. | |
| 3,390,821 A | 7/1968 | Mullan | |
| 3,411,503 A | 11/1968 | Santomieri | |
| 3,442,424 A | 5/1969 | Sam et al. | |
| 3,471,058 A | 10/1969 | Peter et al. | |
| 3,473,524 A | 10/1969 | John | |
| 3,474,844 A | 10/1969 | Rudolph et al. | |
| 3,506,163 A | 4/1970 | James et al. | |
| 3,557,788 A | 1/1971 | Swartz | |
| 3,613,963 A | 10/1971 | Berkmuller | |
| 3,618,846 A | 11/1971 | Poli | |
| 3,826,409 A | 7/1974 | Chilcoate | |
| 3,873,003 A | 3/1975 | Seiferth et al. | |
| 3,938,514 A | 2/1976 | Boucher | |
| 4,035,461 A | 7/1977 | Korth | |
| 4,044,836 A | 8/1977 | Martin et al. | |
| 4,064,879 A | 12/1977 | Leibinsohn | |
| 4,066,080 A | 1/1978 | Sneider | |
| 4,131,217 A | 12/1978 | Sandegren | |
| 4,136,802 A | 1/1979 | Mascia et al. | |
| 4,171,698 A | 10/1979 | Genese | |
| 4,349,129 A | 9/1982 | Amneus | |
| 4,392,491 A | 7/1983 | Takasugi et al. | |
| 4,411,656 A | 10/1983 | Cornett, III | |
| 4,526,296 A | 7/1985 | Berger et al. | |
| 4,677,980 A * | 7/1987 | Reilly | A61M 5/31511 600/432 |
| 4,753,638 A | 6/1988 | Peters | |
| 4,773,458 A | 9/1988 | Touzani | |
| 4,850,807 A | 7/1989 | Frantz | |
| 5,000,739 A | 3/1991 | Kulisz et al. | |
| 5,201,438 A | 4/1993 | Norwood | |
| 5,209,372 A | 5/1993 | Norwood | |
| 5,236,204 A | 8/1993 | Hempel | |
| 5,238,150 A | 8/1993 | Williams | |
| 5,240,130 A | 8/1993 | Osbakk | |
| 5,242,422 A | 9/1993 | Schneberger et al. | |
| 5,269,428 A | 12/1993 | Gilbert | |
| 5,333,761 A | 8/1994 | Davis et al. | |
| 5,353,961 A | 10/1994 | Debush | |
| 5,370,250 A | 12/1994 | Gilbert | |
| 5,383,858 A | 1/1995 | Reilly et al. | |
| 5,397,157 A | 3/1995 | Hempel et al. | |
| 5,573,129 A | 11/1996 | Nagata et al. | |
| 5,584,413 A | 12/1996 | Jung | |
| 5,592,948 A | 1/1997 | Gatten | |
| 5,609,580 A | 3/1997 | Kwiatkowski et al. | |
| 5,615,791 A | 4/1997 | Vatelot et al. | |
| 5,638,995 A | 6/1997 | Mazda | |
| 5,683,369 A | 11/1997 | Tsukada | |
| 5,758,789 A | 6/1998 | Shin et al. | |
| 5,794,107 A | 8/1998 | Russell | |
| 5,827,233 A | 10/1998 | Futagawa et al. | |
| 5,836,922 A | 11/1998 | Hansen et al. | |
| 5,873,861 A | 2/1999 | Hitchins et al. | |
| 5,899,889 A | 5/1999 | Futagawa et al. | |
| RE36,377 E | 11/1999 | Gilbert | |
| 5,979,326 A | 11/1999 | Ohinata | |
| 6,054,194 A | 4/2000 | Kane | |
| 6,062,437 A | 5/2000 | Mascitelli | |
| 6,077,252 A | 6/2000 | Siegel | |
| 6,105,815 A | 8/2000 | Mazda | |
| 6,142,976 A | 11/2000 | Kubo | |
| 6,196,999 B1 * | 3/2001 | Goethel | A61M 5/31515 604/218 |
| 6,216,915 B1 | 4/2001 | Harman et al. | |
| 6,224,577 B1 | 5/2001 | Dedola et al. | |
| 6,250,505 B1 | 6/2001 | Petit | |
| 6,306,191 B1 | 10/2001 | McInerney et al. | |
| 6,315,761 B1 | 11/2001 | Shcherbina et al. | |
| 6,319,235 B1 | 11/2001 | Yoshino | |
| 6,332,876 B1 | 12/2001 | Poynter et al. | |
| 6,485,471 B1 | 11/2002 | Zivitz et al. | |
| 6,558,358 B2 | 5/2003 | Rosoff et al. | |
| 6,578,738 B1 | 6/2003 | Keller | |
| 6,620,134 B1 | 9/2003 | Trombley, III et al. | |
| 6,634,524 B1 | 10/2003 | Helmenstein | |
| 6,652,489 B2 | 11/2003 | Trocki et al. | |
| 6,702,143 B2 | 3/2004 | Wang | |
| 6,773,417 B2 | 8/2004 | Fitzgibbons et al. | |
| 6,840,164 B2 | 1/2005 | Eastman | |
| 6,866,039 B1 | 3/2005 | Wright et al. | |
| 6,869,419 B2 | 3/2005 | Dragan et al. | |
| RE38,770 E | 8/2005 | Gilbert | |
| 7,004,213 B2 | 2/2006 | Hansen | |
| 7,011,650 B2 | 3/2006 | Rosoff et al. | |
| 7,192,549 B2 | 3/2007 | Hansen | |
| 7,250,039 B2 | 7/2007 | Fitzgerald | |
| 7,309,463 B2 | 12/2007 | Hansen | |
| 7,419,478 B1 | 9/2008 | Reilly et al. | |

(56) References Cited

U.S. PATENT DOCUMENTS

| | | | |
|---|---|---|---|
| 7,513,378 B2 | 4/2009 | Mori et al. | |
| 7,553,294 B2 | 6/2009 | Lazzaro et al. | |
| 7,563,249 B2 | 7/2009 | Schriver et al. | |
| 7,604,623 B2 | 10/2009 | Brunner et al. | |
| 7,666,169 B2 | 2/2010 | Cowan et al. | |
| 7,802,691 B2 | 9/2010 | Musalek et al. | |
| 8,728,601 B2 | 5/2014 | Hutts et al. | |
| 9,173,995 B1 | 11/2015 | Tucker et al. | |
| 9,180,252 B2 | 11/2015 | Gelblum et al. | |
| 9,199,033 B1 | 12/2015 | Cowan et al. | |
| 10,124,110 B2 | 11/2018 | Dedig et al. | |
| 11,207,462 B2 * | 12/2021 | Cowan | A61M 5/14586 |
| 11,547,793 B2 * | 1/2023 | Cowan | A61M 5/007 |
| 2004/0116893 A1 * | 6/2004 | Spohn | A61M 5/14546 604/181 |
| 2004/0249344 A1 | 12/2004 | Nemoto et al. | |
| 2009/0112087 A1 | 4/2009 | Fago | |
| 2010/0091361 A1 | 4/2010 | Yuuki | |
| 2010/0286650 A1 | 11/2010 | Fitzgerald | |
| 2011/0009826 A1 * | 1/2011 | Lewis | A61M 5/14546 604/154 |
| 2012/0020911 A1 | 1/2012 | Seliktar et al. | |
| 2012/0209111 A1 | 8/2012 | Cowan et al. | |
| 2012/0253291 A1 | 10/2012 | Ivosevic et al. | |
| 2013/0030291 A1 | 1/2013 | Lewis | |
| 2013/0043273 A1 | 2/2013 | Lee et al. | |
| 2013/0204130 A1 | 8/2013 | McArthur et al. | |
| 2013/0211248 A1 | 8/2013 | Cowan et al. | |
| 2013/0281940 A1 | 10/2013 | Gelblum et al. | |
| 2014/0124087 A1 | 5/2014 | Anderson et al. | |

FOREIGN PATENT DOCUMENTS

| | | | |
|---|---|---|---|
| EP | 2767299 A1 | 8/2014 | |
| EP | 3057648 A1 | 8/2016 | |
| FR | 1288915 A | 3/1962 | |
| GB | 2214819 A | 9/1989 | |
| GB | 2374143 A | 10/2002 | |
| WO | 9221391 A1 | 12/1992 | |
| WO | WO-2009023463 A1 * | 2/2009 | ........ A61M 5/14546 |
| WO | 2010004206 A2 | 1/2010 | |
| WO | 2010014654 A1 | 2/2010 | |
| WO | 2011129175 A1 | 10/2011 | |
| WO | 2012061140 A1 | 5/2012 | |
| WO | 2012155035 A1 | 11/2012 | |
| WO | 2014027009 A1 | 2/2014 | |
| WO | 2015058088 A1 | 4/2015 | |
| WO | 2015066506 A2 | 5/2015 | |
| WO | 2015164783 A1 | 10/2015 | |
| WO | 2016058946 A1 | 4/2016 | |
| WO | 2016069711 A1 | 5/2016 | |
| WO | 2016069714 A1 | 5/2016 | |
| WO | 2016112163 A1 | 7/2016 | |
| WO | 2016157886 A1 | 10/2016 | |
| WO | 2018075386 A1 | 4/2018 | |

* cited by examiner

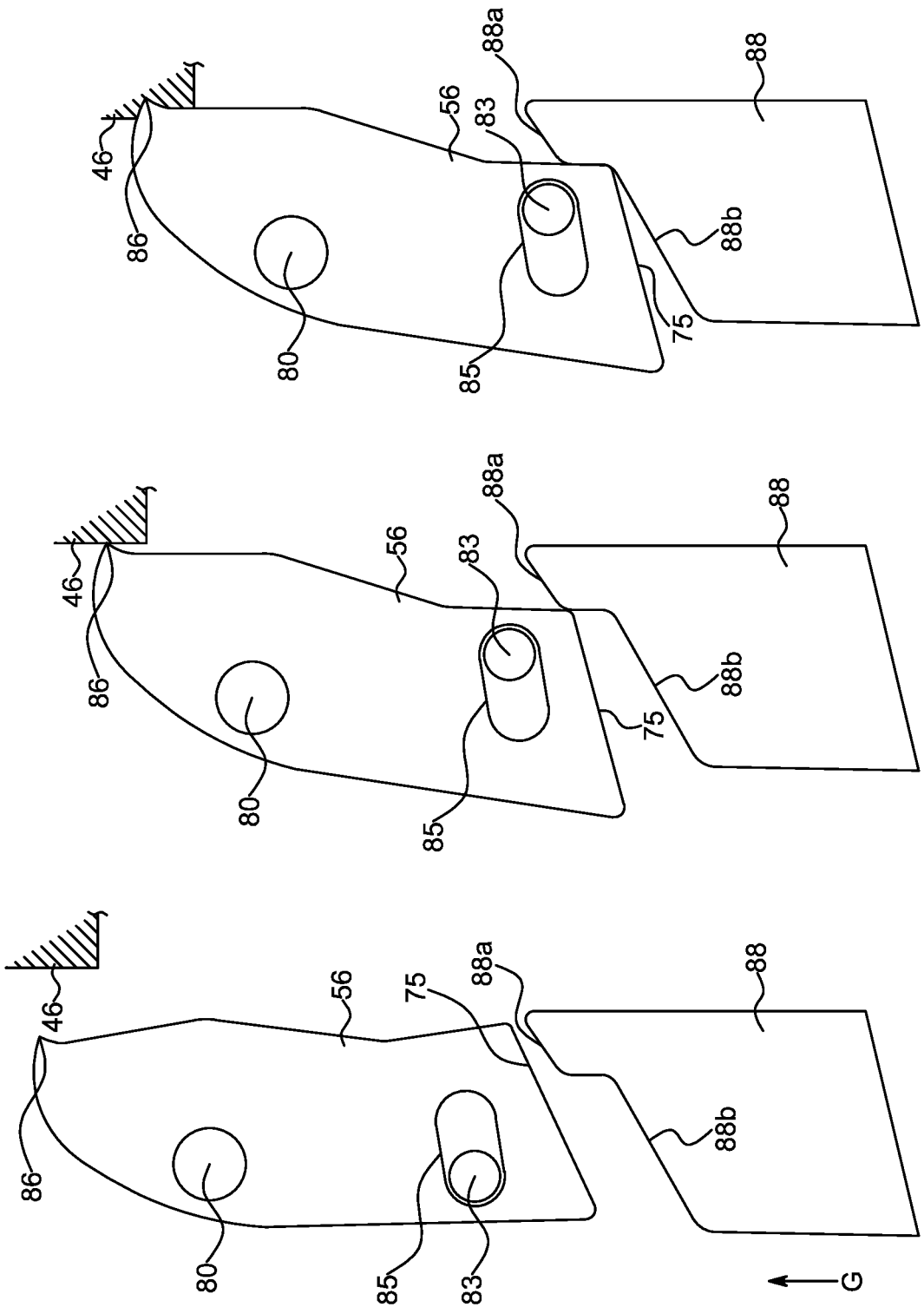

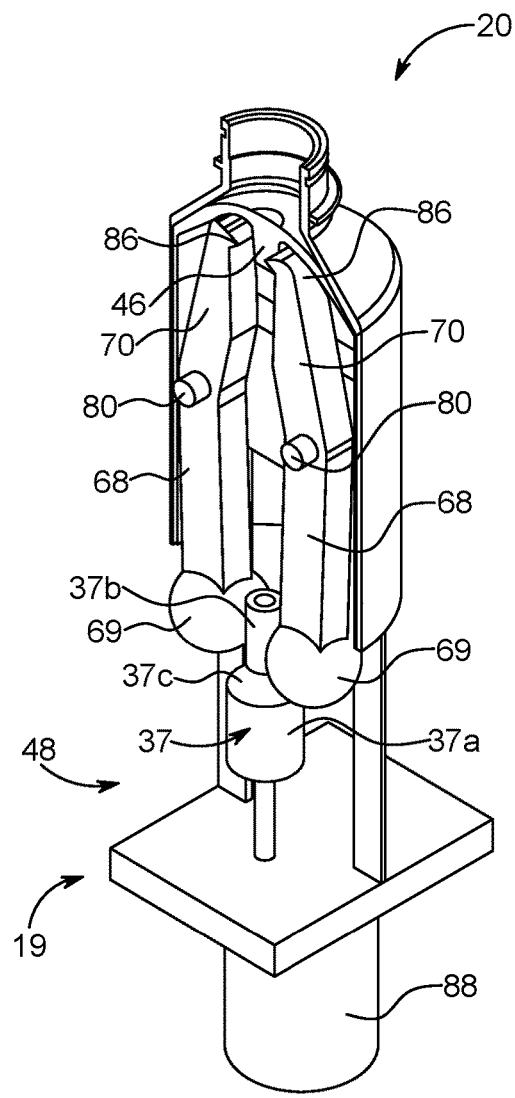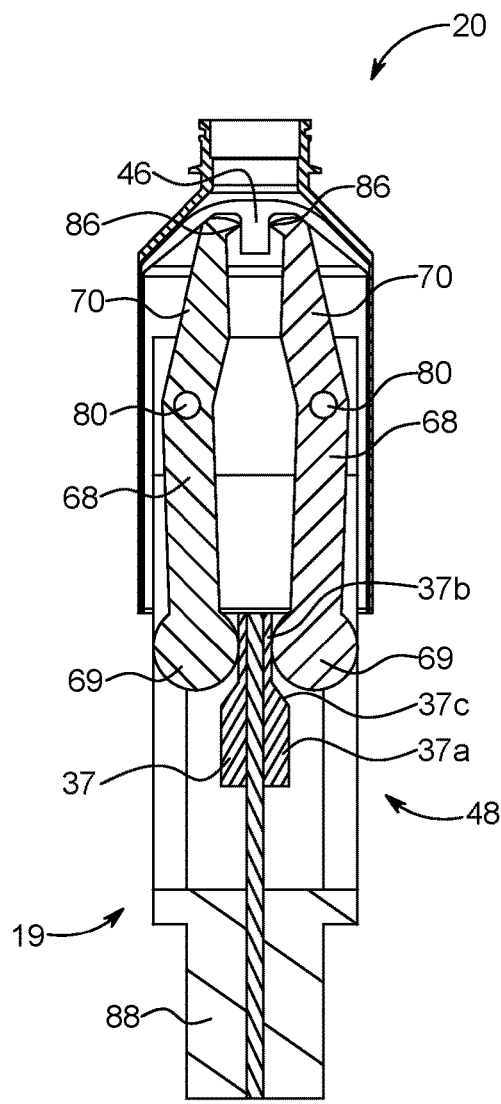
FIG. 10A
FIG. 10B

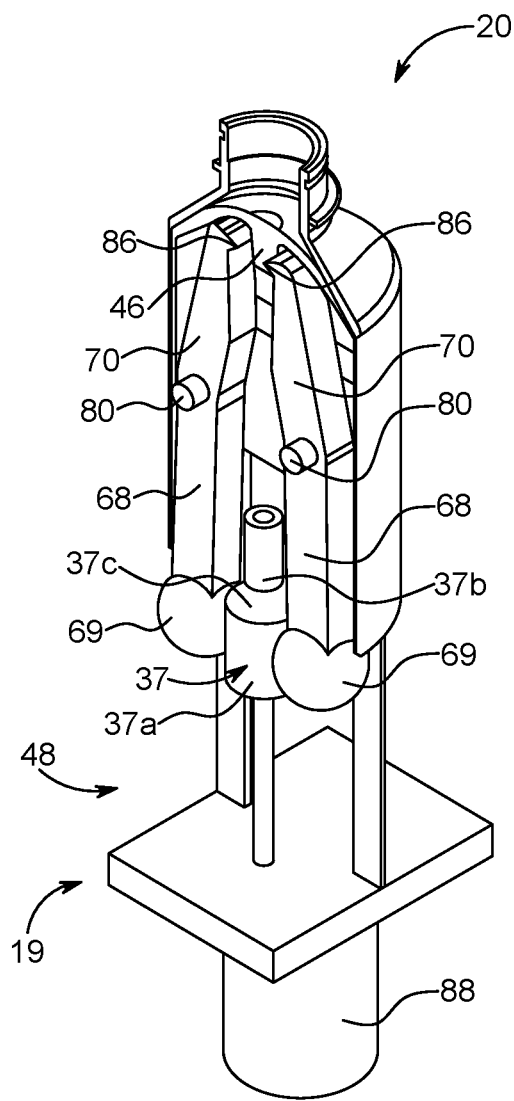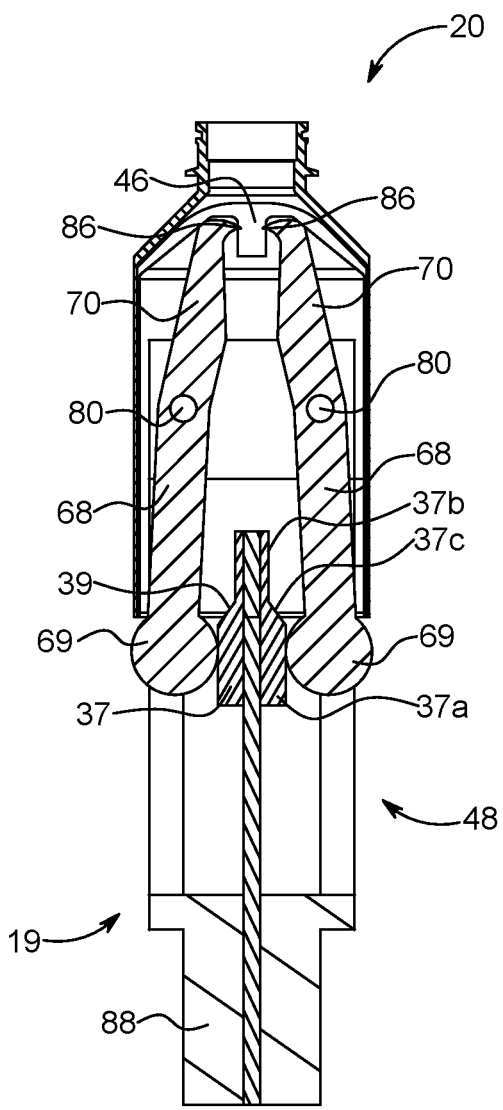
FIG. 10C
FIG. 10D

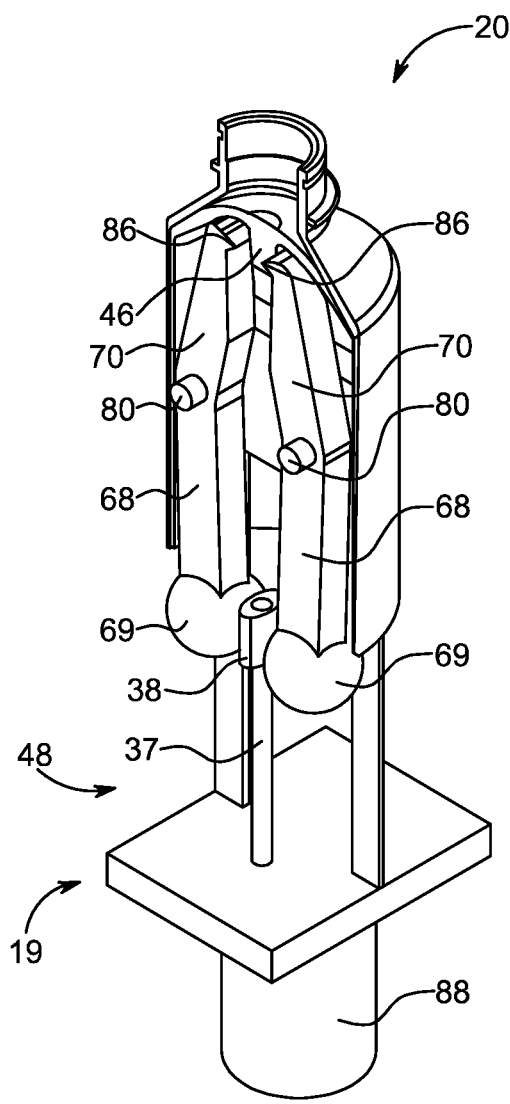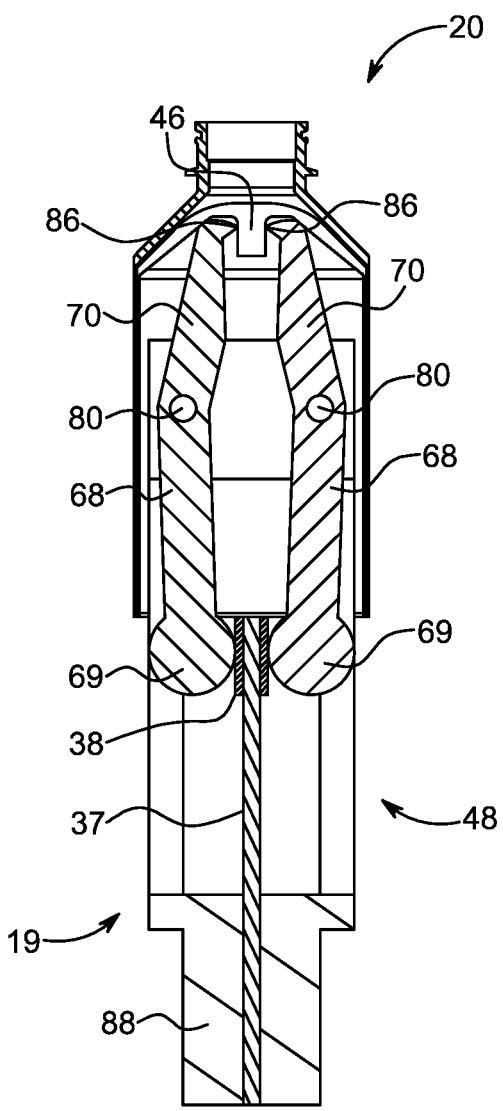
FIG. 11A
FIG. 11B

FLUID INJECTOR WITH SYRINGE ENGAGEMENT MECHANISM

CROSS-REFERENCE TO RELATED APPLICATIONS

This application is a Continuation application from U.S. Ser. No. 16/341,205, filed Apr. 11, 2019, which is a 371 national phase application of PCT International Application No. PCT/US2017/056747, filed Oct. 16, 2017, and claims priority to U.S. Provisional Application No. 62/409,039, filed Oct. 17, 2016; U.S. Provisional Application No. 62/409,044, filed Oct. 17, 2016; U.S. Provisional Application No. 62/409,032, filed Oct. 17, 2016; U.S. Provisional Application No. 62/545,693, filed Aug. 15, 2017; U.S. Provisional Application No. 62/545,728, filed Aug. 15, 2017; and U.S. Provisional Application No. 62/545,798, filed Aug. 15, 2017, the disclosures of which are incorporated by reference herein in their entirety.

BACKGROUND OF THE DISCLOSURE

Field of the Disclosure

The present disclosure is related to fluid injectors for use in the medical field and, more particularly, to fluid injectors having a syringe engagement mechanism for engaging a syringe with a flexible sidewall and a piston engagement portion on at least a portion of the flexible sidewall.

Description of Related Art

In many medical diagnostic and therapeutic procedures, a medical practitioner, such as a physician, injects a patient with one or more medical fluids. In recent years, a number of injector-actuated syringes and powered fluid injectors for pressurized injection of medical fluids, such as a contrast solution (often referred to simply as "contrast"), a flushing agent, such as saline, and other medical fluids, have been developed for use in procedures such as angiography, computed tomography (CT), ultrasound, magnetic resonance imaging (MRI), positron emission tomography (PET), and other imaging procedures. In general, these fluid injectors are designed to deliver a preset amount of medical fluid at a preset pressure and/or flow rate.

Typically, powered injectors have pistons that connect to a syringe plunger that is slidably disposed within the syringe. The syringe generally includes a rigid barrel with the syringe plunger being slidably disposed within the barrel. The piston drives the plunger in a direction of a longitudinal axis of the barrel to draw fluid into the syringe barrel with a proximal movement of the piston or deliver the fluid from the syringe barrel with a distal movement of the piston. While various connection mechanisms exist in the art for engaging the piston of the fluid injector with the syringe, it remains desirable to develop improved designs of syringes and syringe engagement mechanisms to facilitate injection procedures.

SUMMARY OF THE DISCLOSURE

The present disclosure generally relates to fluid injectors having a syringe engagement mechanism for engaging a syringe with a flexible sidewall and a piston engagement portion on at least a portion of the flexible sidewall.

In some examples of the present disclosure, an engagement mechanism may be associated with a reciprocally movable piston of a fluid injector. The engagement mechanism may be configured for releasably engaging an engagement portion at a proximal end of a rolling diaphragm syringe having a flexible sidewall configured for rolling upon itself when acted upon by the piston. The engagement mechanism may have a plurality of engagement elements reversibly and radially movable relative to the engagement portion of the syringe between a first position, where the plurality of engagement elements are disengaged from the engagement portion of the syringe, and a second position, where the plurality of engagement elements are engaged with the engagement portion of the syringe. The engagement mechanism may further have a drive mechanism for moving the plurality of engagement elements between the first position and the second position.

In other examples of the present disclosure, the drive mechanism may be operatively connected to the piston such that the plurality of engagement elements are movable from the first position to the second position with movement of the piston in a proximal direction. The plurality of engagement elements may be movable from the second positon to the first position with movement of the piston in a distal direction. The drive mechanism may move the plurality of engagement elements between the first position and the second position independently of movement of the piston in a proximal direction or a distal direction. The drive mechanism may have at least one of the following a linear electric motor or actuator, a rotary electric motor or actuator, a solenoid, a pneumatic mechanism, a hydraulic mechanism, an electromagnetic mechanism, an electroactive polymer mechanism, a nitinol wire-based mechanism, and any combination thereof. The drive mechanism may have a rod linearly or rotatably movable by a motor. Linear or rotary movement of the rod may reversibly move the plurality of engagement members between the first position and the second position.

In other examples of the present disclosure, the drive mechanism may have an outer piston sleeve fixed relative to the piston of the fluid injector and an abutment section movably received within the outer piston sleeve at a distal end of the outer piston sleeve. The abutment section may be operatively engaged with the plurality of engagement members. The drive mechanism further may have an inner piston sleeve movably received within the outer piston sleeve and connected with the abutment section such that movement of the inner piston sleeve causes movement of the abutment section. The inner piston sleeve may be movable by a piston rod movably coupled to the piston, wherein movement of the piston in a proximal direction moves the outer piston sleeve proximally relative to the abutment section, and wherein proximal movement of the outer piston sleeve relative to the abutment section may move the plurality of engagement members from the first position to the second position.

In other examples of the present disclosure, the abutment section may have an outer engagement surface configured for contacting a closed end wall of the syringe at a central opening on the outer engagement surface configured for receiving the engagement portion of the syringe. The plurality of engagement elements may be progressively movable from the first position to the second position with movement of the piston in a proximal direction to continuously increase a gripping force on the engagement portion of the syringe. Each of the plurality of engagement elements may be pivotally movable between the first position and the second position by rotation about a pivot pin. Each of the plurality of engagement elements may be movable between the first position and the second position by movement of a pin along an inclined ramp. Each of the plurality of engagement elements may be linearly movable between the first position and the second position in a radially inward or outward direction relative to a longitudinal axis of the piston. The plurality of engagement elements may be biased to one of the first position or the second position by a biasing mechanism. The biasing mechanism may be a spring.

In other examples of the present disclosure, a fluid injector may have at least one injector head comprising at least one reciprocally movable piston and an engagement mechanism associated with the at least one piston and configured for releasably engaging an engagement portion at a proximal end of a rolling diaphragm syringe having a flexible sidewall configured for rolling upon itself when acted upon by the piston. The engagement mechanism may have a plurality of engagement elements reversibly and radially movable relative to the engagement portion of the syringe between a first position, where the plurality of engagement elements are disengaged from the engagement portion of the syringe, and a second position, where the plurality of engagement elements are engaged with the engagement portion of the syringe. The fluid injector may further have a drive mechanism for moving the plurality of engagement elements between the first position and the second position.

In other examples of the present disclosure, the drive mechanism may be operatively connected to the at least one piston such that the plurality of engagement elements are movable from the first position to the second position with movement of the at least one piston in a proximal direction. The plurality of engagement elements may be movable from the second positon to the first position with movement of the at least one piston in a distal direction. The drive mechanism may move the plurality of engagement elements between the first position and the second position independently of movement of the at least one piston in a proximal direction or a distal direction. The drive mechanism may have at least one of the following a linear electric motor or actuator, a rotary electric motor or actuator, a solenoid, a pneumatic mechanism, a hydraulic mechanism, an electromagnetic mechanism, an electroactive polymer mechanism, a nitinol wire-based mechanism, and any combination thereof. The drive mechanism may have a rod linearly or rotatably movable by a motor. Linear or rotary movement of the rod may reversibly move the plurality of engagement members between the first position to the second position. Each of the plurality of engagement elements may be pivotally movable between the first position to the second position by rotation about a pivot pin. Each of the plurality of engagement elements may be linearly movable between the first position to the second position in a radially inward or outward direction relative to a longitudinal axis of the at least one piston.

Various other examples of the present disclosure are recited in one or more of the following enumerated clauses:

Clause 1: An engagement mechanism associated with a reciprocally movable piston of a fluid injector and configured for releasably engaging an engagement portion at a proximal end of a rolling diaphragm syringe having a flexible sidewall configured for rolling upon itself when acted upon by the piston, the engagement mechanism comprising: a plurality of engagement elements reversibly and radially movable relative to the engagement portion of the syringe between a first position, where the plurality of engagement elements are disengaged from the engagement portion of the syringe, and a second position, where the plurality of engagement elements are engaged with the engagement portion of the syringe; and a drive mechanism for moving the plurality of engagement elements between the first position and the second position.

Clause 2: The engagement mechanism of clause 1, wherein the drive mechanism is operatively connected to the piston such that the plurality of engagement elements are movable from the first position to the second position with movement of the piston in a proximal direction.

Clause 3: The engagement mechanism of clause 2, wherein the plurality of engagement elements are movable from the second positon to the first position with movement of the piston in a distal direction.

Clause 4: The engagement mechanism of clause 1, wherein the drive mechanism moves the plurality of engagement elements between the first position and the second position independently of movement of the piston in a proximal direction or a distal direction.

Clause 5: The engagement mechanism of any of clauses 1 to 4, wherein the drive mechanism comprises at least one of the following: a linear electric motor or actuator, a rotary electric motor or actuator, a solenoid, a pneumatic mechanism, a hydraulic mechanism, an electromagnetic mechanism, an electroactive polymer mechanism, a nitinol wire-based mechanism, and any combination thereof.

Clause 6: The engagement mechanism of any of clauses 1 to 5, wherein the drive mechanism comprises a rod linearly or rotatably movable by a motor, and wherein linear or rotary movement of the rod reversibly moves the plurality of engagement members between the first position and the second position.

Clause 7: The engagement mechanism of any of clauses 1 to 5, wherein the drive mechanism comprises: an outer piston sleeve fixed relative to the piston of the fluid injector; an abutment section movably received within the outer piston sleeve at a distal end of the outer piston sleeve, wherein the abutment section is operatively engaged with the plurality of engagement members; and an inner piston sleeve movably received within the outer piston sleeve and connected with the abutment section such that movement of the inner piston sleeve causes movement of the abutment section, wherein the inner piston sleeve is movable by a piston rod movably coupled to the piston, wherein movement of the piston in a proximal direction moves the outer piston sleeve proximally relative to the abutment section, and wherein proximal movement of the outer piston sleeve relative to the abutment section moves the plurality of engagement members from the first position to the second position.

Clause 8: The engagement mechanism of clause 7, wherein the abutment section has an outer engagement surface configured for contacting a closed end wall of the syringe at a central opening on the outer engagement surface configured for receiving the engagement portion of the syringe.

Clause 9: The engagement mechanism of any of clauses 1 to 8, wherein the plurality of engagement elements are progressively movable from the first position to the second position with movement of the piston in a proximal direction to continuously increase a gripping force on the engagement portion of the syringe.

Clause 10: The engagement mechanism of any of clauses 1 to 9, wherein each of the plurality of engagement elements is pivotally movable between the first position and the second position by rotation about a pivot pin.

Clause 11: The engagement mechanism of any of clauses 1 to 10, wherein each of the plurality of engagement elements is movable between the first position and the second position by movement of a pin along an inclined ramp.

Clause 12: The engagement mechanism of any of clauses 1 to 6, wherein each of the plurality of engagement elements is linearly movable between the first position and the second position in a radially inward or outward direction relative to a longitudinal axis of the piston.

Clause 13: The engagement mechanism of any of clauses 1 to 12, wherein the plurality of engagement elements are biased to one of the first position or the second position by a biasing mechanism.

Clause 14: The engagement mechanism of clause 13, wherein the biasing mechanism is a spring.

Clause 15: A fluid injector comprising: at least one injector head comprising at least one reciprocally movable piston; an engagement mechanism associated with the at least one piston and configured for releasably engaging an engagement portion at a proximal end of a rolling diaphragm syringe having a flexible sidewall configured for rolling upon itself when acted upon by the piston, the engagement mechanism comprising: a plurality of engagement elements reversibly and radially movable relative to the engagement portion of the syringe between a first position, where the plurality of engagement elements are disengaged from the engagement portion of the syringe, and a second position, where the plurality of engagement elements are engaged with the engagement portion of the syringe; and a drive mechanism for moving the plurality of engagement elements between the first position and the second position.

Clause 16: The fluid injector of clause 15, wherein the drive mechanism is operatively connected to the at least one piston such that the plurality of engagement elements are movable from the first position to the second position with movement of the at least one piston in a proximal direction.

Clause 17: The fluid injector of clause 16, wherein the plurality of engagement elements are movable from the second positon to the first position with movement of the at least one piston in a distal direction.

Clause 18: The fluid injector of clause 15, wherein the drive mechanism moves the plurality of engagement elements between the first position and the second position independently of movement of the at least one piston in a proximal direction or a distal direction.

Clause 19: The fluid injector of any of clauses 15 to 18, wherein the drive mechanism comprises at least one of the following a linear electric motor or actuator, a rotary electric motor or actuator, a solenoid, a pneumatic mechanism, a hydraulic mechanism, an electromagnetic mechanism, an electroactive polymer mechanism, a nitinol wire-based mechanism, and any combination thereof.

Clause 20: The fluid injector of any of clauses 15 to 19, wherein the drive mechanism comprises a rod linearly or rotatably movable by a motor, and wherein linear or rotary movement of the rod reversibly moves the plurality of engagement members between the first position to the second position.

Clause 21: The fluid injector of any of clauses 15 to 20, wherein each of the plurality of engagement elements is pivotally movable between the first position to the second position by rotation about a pivot pin.

Clause 22: The fluid injector of any of clauses 15 to 21, wherein each of the plurality of engagement elements is linearly movable between the first position to the second position in a radially inward or outward direction relative to a longitudinal axis of the at least one piston.

Further details and advantages of the various examples described in detail herein will become clear upon reviewing the following detailed description in conjunction with the accompanying drawing figures.

BRIEF DESCRIPTION OF THE DRAWINGS

FIGS. 6A-6C are side views of engagement arms of a syringe engagement mechanism in accordance with one example of the present disclosure showing a movement of the engagement arms between an open state or configuration and a closed state or configuration;

FIG. 10A is a perspective, partial cross-sectional view of a syringe and a piston having a syringe engagement mechanism in accordance with one example of the present disclosure shown in an open state or configuration;

FIG. 10B is a side cross-sectional view of the syringe and the piston with the syringe engagement mechanism shown in FIG. 10A;

FIG. 10C is a perspective, partial cross-sectional view of the syringe and the piston with the syringe engagement mechanism shown in FIG. 10A with the syringe engagement mechanism shown in a closed state or configuration;

FIG. 10D is a side cross-sectional view of the syringe and the piston with the syringe engagement mechanism shown in FIG. 10C;

FIG. 11A is a perspective, partial cross-sectional view of a syringe and a piston having a syringe engagement mechanism in accordance with one example of the present disclosure shown in an open state or configuration;

FIG. 11B is a side cross-sectional view of the syringe and the piston with the syringe engagement mechanism shown in FIG. 11A;

DETAILED DESCRIPTION

Figure 1:
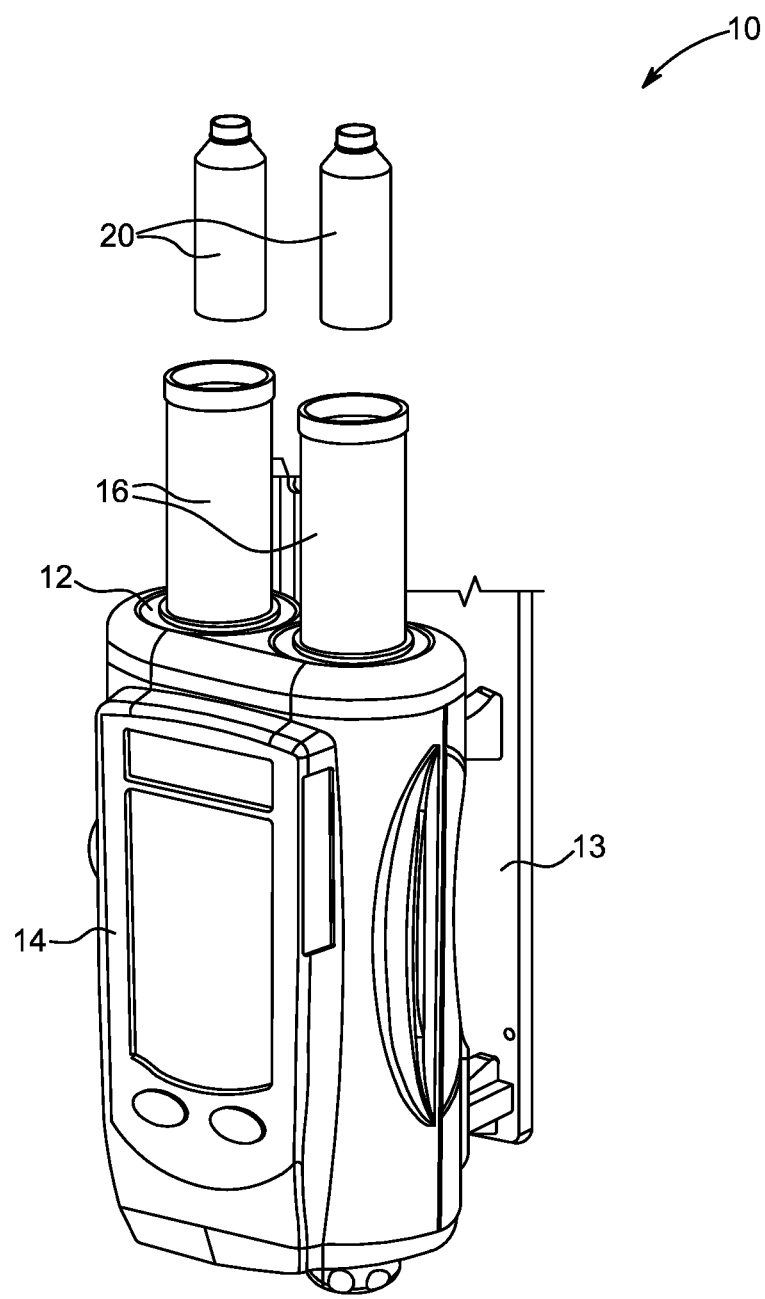
FIG. 1 is a front perspective view of a fluid injector having a pair of pressure jackets and syringes in accordance with one example of the present disclosure.

As used in the specification, the singular form of "a", "an", and "the" include plural referents unless the context clearly dictates otherwise.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures.

Spatial or directional terms, such as "left", "right", "inner", "outer", "above", "below", and the like, are not to be considered as limiting as the invention can assume various alternative orientations.

When used in relation to a syringe and/or a pressure jacket, the term "proximal" refers to a portion of a syringe and/or a pressure jacket nearest to an injector when a syringe and/or a pressure jacket is oriented for connecting to an injector.

The term "distal" refers to a portion of a syringe and/or a pressure jacket farthest away from an injector when a syringe and/or a pressure jacket is oriented for connecting to an injector.

The term "radial" refers to a direction in a cross-sectional plane normal to a longitudinal axis of a syringe and/or a pressure jacket extending between proximal and distal ends.

The term "circumferential" refers to a direction around an inner or outer surface of a sidewall of a syringe and/or a pressure jacket.

The term "axial" refers to a direction along a longitudinal axis of a syringe and/or a pressure jacket extending between the proximal and distal ends.

The term "flexible", when used in connection with a syringe, means that at least a portion of a syringe, such as a sidewall of a syringe, is capable of bending or being bent, for example up to 180°, to change a direction in which it extends.

The terms "roll over", "rolling over", and "rolls upon itself" refer to an ability of a first portion of a syringe, such as a proximal portion of a sidewall of a syringe, to bend approximately 1800 relative to a second portion of a syringe, such as a distal portion of a sidewall of a syringe, when urged by a piston of a fluid injector.

All numbers used in the specification and claims are to be understood as being modified in all instances by the term "about". The term "about" means a range of plus or minus ten percent of the stated value.

Unless otherwise indicated, all ranges or ratios disclosed herein are to be understood to encompass any and all subranges or sub-ratios subsumed therein. For example, a stated range or ratio of "1 to 10" should be considered to include any and all subranges between (and inclusive of) the minimum value of 1 and the maximum value of 10; that is, all subranges or sub-ratios beginning with a minimum value of 1 or more and ending with a maximum value of 10 or less, such as but not limited to, 1 to 6.1, 3.5 to 7.8, and 5.5 to 10.

The term "at least" means "greater than or equal to".

The term "includes" is synonymous with "comprises".

It is to be understood that the specific devices and processes illustrated in the attached drawings, and described in the following specification, are simply exemplary examples of the disclosure. Hence, specific dimensions and other physical characteristics related to the examples disclosed herein are not to be considered as limiting.

All documents, such as but not limited to issued patents and patent applications, referred to herein, and unless otherwise indicated, are to be considered to be "incorporated by reference" in their entirety.

Referring to the drawings in which like reference characters refer to like parts throughout the several views thereof, the present disclosure is generally directed to fluid injectors having a syringe engagement mechanism for engaging a syringe with a flexible sidewall and a piston engagement portion on at least a portion of the flexible sidewall. The syringe engagement mechanism has a plurality of engagement elements movable in a radial direction relative to the engagement portion of the syringe from a first position, wherein the plurality of engagement elements are disengaged from the engagement portion of the syringe, and a second position, wherein the plurality of engagement elements are engaged with the engagement portion of the syringe.

With reference to FIG. 1, a fluid injector 10 includes at least one injector head 12 and an injector housing 14. The injector 10 may be supported on a support structure 13. In some examples, such as shown in FIG. 1, the fluid injector 10 may include two injector heads 12 arranged in a side-by-side orientation. Each injector head 12 may be formed at a front end of the injector housing 14 and may be configured for receiving and retaining at least one pressure jacket 16. While FIG. 1 illustrates the fluid injector 10 with two injector heads 12, each with a corresponding pressure jacket 16, other examples of the fluid injector 10 may include a single injector head 12 and a corresponding pressure jacket 16 or more than two injector heads 12 with a corresponding number of pressure jackets 16. The pressure jacket 16 may be removably attached to the injector head 12 with one or more engagement elements, for example the one or more engagement elements described in PCT International Publications WO 2016/069714 and WO 2016/069711, the disclosures of which are incorporated herein by this reference.

Each injector head 12 includes a drive member, such as a reciprocally driven piston 19 (shown in FIGS. 3A-3B), moved by a motor, the movement of which is controlled by a controller. Each piston 19 may be configured to extend into and from the respective injector head 12 through an opening in the front end of the injector housing 14. Each piston 19 imparts a motive force to at least a portion of the syringe or to a plunger within the syringe disposed in the respective pressure jacket 16, as described herein.

With continued reference to FIG. 1, the fluid injector 10 is configured to receive a syringe 20 within each pressure jacket 16. The at least one pressure jacket 16 is typically a reusable component, while the syringe 20 is typically a single-use component. In some examples, the syringe 20 may be a multi-use component. The fluid injector 10 may have at least one bulk fluid source for filling the syringes 20 with fluid. At least one fluid path set may be fluidly connected with a discharge end of each syringe 20 for delivering fluid from the syringes 20 through tubing connected to a catheter, needle, or other fluid delivery connection (not shown) inserted into a patient at a vascular access site. Fluid flow into and from the at least one syringe 20 may be regulated by a fluid control module (not shown). The fluid control module may operate various pistons, valves, and/or flow regulating structures to regulate the delivery of the medical fluid, such as saline solution and contrast, to the patient based on user selected injection parameters, such as injection flow rate, duration, total injection volume, and/or ratio of contrast media and saline. Examples of suitable front-loading fluid injectors that may be used or modified for use with the herein-described system, including at least one pressure jacket 16 and syringe 20, are disclosed in PCT Application Publication No. WO 2015/164783 and PCT Application Publication No. WO 2016/172467, the disclosures of which are incorporated herein by reference.

Figure 2A:
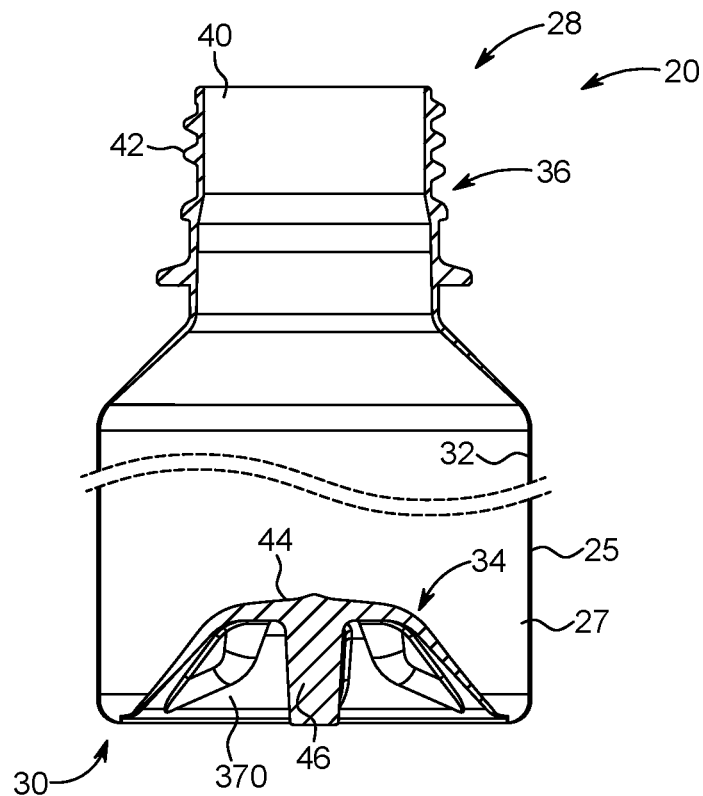
FIG. 2A is a side cross-sectional view of a syringe in accordance with one example of the present disclosure, with the syringe shown in an unrolled configuration.
Figure 2B:
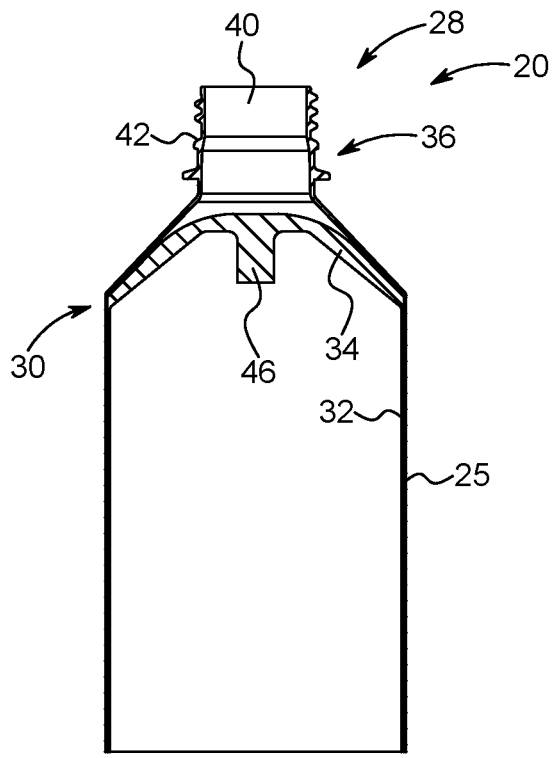
FIG. 2B is a side cross-sectional view of the syringe of FIG. 2A shown in a rolled configuration.

With reference to FIGS. 2A-2B, in certain examples, the syringe 20 generally includes a hollow body 25 defining an interior volume 27. The body 25 has a forward or distal end 28, a rearward or proximal end 30, and a flexible sidewall 32 extending therebetween. The sidewall 32 of the syringe 20 defines a soft, pliable or flexible, yet self-supporting body that is configured to roll upon itself, as a rolling diaphragm, under the action of the piston 19. In particular, the sidewall 32 is configured to roll such that its outer surface is folded and inverted in a radially inward direction as the piston 19 is moved in a distal direction (FIG. 2B) and unrolled and unfolded in the opposite manner in a radially outward direction as the piston 19 is retracted in a proximal direction (FIG. 2A). The sidewall 32 may have a smooth, substantially uniform structure, or it may have one or more ribs provided thereon to facilitate the rollover during an injection procedure. In some examples, the sidewall 32 and/or the end wall 34 may have a textured surface, or a combination of a smooth surface and a textured surface. One or more indicia (not shown) may be formed on the sidewall 32. In some examples, the sidewall 32 may have a uniform thickness along its longitudinal length. In other examples, the sidewall 32 may have a non-uniform thickness along its longitudinal length. In specific examples, the sidewall 32 at or near the distal end 28 may be substantially rigid. As will be understood by one of skill in the art in view of the present disclosure, the engagement mechanisms described herein may also be used to engage a plunger slidably disposed within the barrel of a syringe, such as described, for example in U.S. Pat. Nos. 6,652,489; 9,173,995; and 9,199,033, the disclosures of which are incorporated by reference herein. According to these embodiments, the plunger may have a piston engagement portion, such as described herein, located on a proximal end of the plunger to interact with the plurality of engagement elements of the various embodiments of the engagement mechanisms described herein.

With continued reference to FIGS. 2A-2B, the rearward or proximal portion of the sidewall 32 connects to a closed end wall 34, and a forward or distal portion of the sidewall 32 defines a discharge neck 36 opposite the closed end wall 34. The closed end wall 34 may have a concave shape to facilitate the initiation of the inversion or rolling of the sidewall 32 and/or to provide a receiving pocket to receive a distal end of piston 19. For example, the closed end wall 34 may define a receiving end pocket 370 for interfacing directly with a similarly-shaped piston 19. In particular examples, at least a portion of the piston 19 may be shaped to substantially match the shape of the closed end wall 34 or, alternatively, pressure from the piston 19 as it is moved distally may conform the end wall 34 to substantially match the shape of at least a portion of the piston 19. The closed end wall 34 may have a non-uniform thickness, for example in a radial direction extending from a central longitudinal axis of the syringe 20. In certain examples, at least a portion of the end wall 34 may be thicker near the center and thinner near the connection with the sidewall 32.

With continued reference to FIGS. 2A-2B, the body 25 of the syringe 20 is adapted to be removably received in the interior portion of the pressure jacket 16. The distal end 28 of the syringe 20 may be secured removably or permanently to a cap (not shown), removably attachable to the pressure jacket 16, or configured with a retention surface to interact with a retaining force to retain the syringe 20 within the pressure jacket 16. For example, the syringe 20 may be secured to the cap by an adhesive, solvent welding, or laser welding, or be removably secured to the cap, such as by a friction fit connection or other suitable mechanical connection. The distal end 28 may have a frusto-conical shape that gradually narrows from the sidewall 32 to the discharge neck 36. In certain examples, the discharge neck 36 may terminate in a discharge port 40 having a connection member 42 for connecting to a cap, fluid path set, or other connection element. In some examples, the connection member 42 is a threaded interface having one or more threads. In other examples, the connection member 42 may have a luer-type connection. In further examples, the side wall 32 may have one or more lips or grooves that interact with corresponding grooves or lips on the pressure jacket 16 to releasably or non-releasably retain the syringe 20 within the pressure jacket 16.

The outer diameter of the syringe 20 may be dimensioned such that the syringe 20 fits within the interior space defined by the throughbore and inner surface of the pressure jacket 16. In one example, the syringe 20 fits snuggly but removably within the pressure jacket 16 such that the outer surface of the syringe 20 abuts at least a portion of the inner surface of the walls of the pressure jacket 16. In another example, the syringe 20 fits loosely within the pressure jacket 16 such that there is a gap between at least a portion of the outer surface of the syringe 20 and the inner surface of the pressure jacket 16. The syringe 20 may be expanded under pressure during an injection procedure such that the outer surface of the syringe 20 abuts the inner surface of the pressure jacket 16. Examples of suitable pressure jacket features are described in PCT International Application No. PCT/US2017/051473, the disclosure of which is incorporated herein by this reference.

The end wall 34 may have a central portion 44 having a substantially dome-shaped structure and a piston engagement portion 46 (hereinafter referred to as "engagement portion 46") extending proximally from the central portion 44. In some examples, the engagement portion 46 may extend in a proximal direction along a longitudinal axis of the syringe 20 from an approximate midpoint of the central portion 44. In some examples, a diameter of the engagement portion 46 may be uniform, such that the engagement portion 46 has a substantially cylindrical structure. In other examples, the diameter of the engagement portion 46 may be non-uniform. For example, the diameter of the engagement portion 46 may gradually decrease or increase in the proximal direction. While the engagement portion 46 is shown in FIGS. 2A-2B as being substantially flush with the proximal end 30 of the syringe 20, in certain examples the engagement portion 46 may extend proximally beyond the proximal end 30 of the syringe 20.

The engagement portion 46 may be monolithically formed with the syringe body 25, or it may be removably or non-removably attached to the central portion 44 of the end wall 34, such as by welding, adhesion, or clip attachment, or other fastening mechanism. The engagement portion 46 is configured for interacting with an engagement mechanism on the piston 19 of the fluid injector 10, as described herein.

The syringe 20 may be made of any suitable medical-grade plastic or polymeric material, desirably a clear or substantially translucent plastic material. The material of the syringe 20 is desirably selected to meet the required tensile and planar stress requirements, water vapor transmission, and chemical/biological compatibility.

In certain embodiments, suitable syringes 20 include a rolling diaphragm-type syringe as described in WO 2015/164783 and WO 2016/172467 having a flexible thin sidewall which rolls upon itself when acted upon by the piston 19 such that an outer surface of the sidewall at a folding region is folded in a radially inward direction as the piston 19 is advanced from the proximal end to the distal end 28 and such that the outer surface of the sidewall 32 at the folding region is unfolded in a radially outward direction as the piston 19 is retracted from the distal end 28 toward the proximal end 30. Such rolling diaphragm syringes may be made from a suitable medical-grade plastic and have a sidewall thickness ranging from 0.0050 inches to 0.20 inches, or in other embodiments from 0.010 inches-0.15 inches. Upon pressurization of the syringe 20 by distal movement of the piston 19, the fluid pressure within the rolling diaphragm syringe causes the sidewall to expand radially outward. This effect is enhanced by the relative thinness of the syringe sidewall compared to conventional syringes. As the syringe sidewall expands radially outward, it contacts the interior surface of the pressure jacket 16, which limits further expansion of the syringe sidewall, thereby preventing breaking of the syringe wall.

Figure 3A:
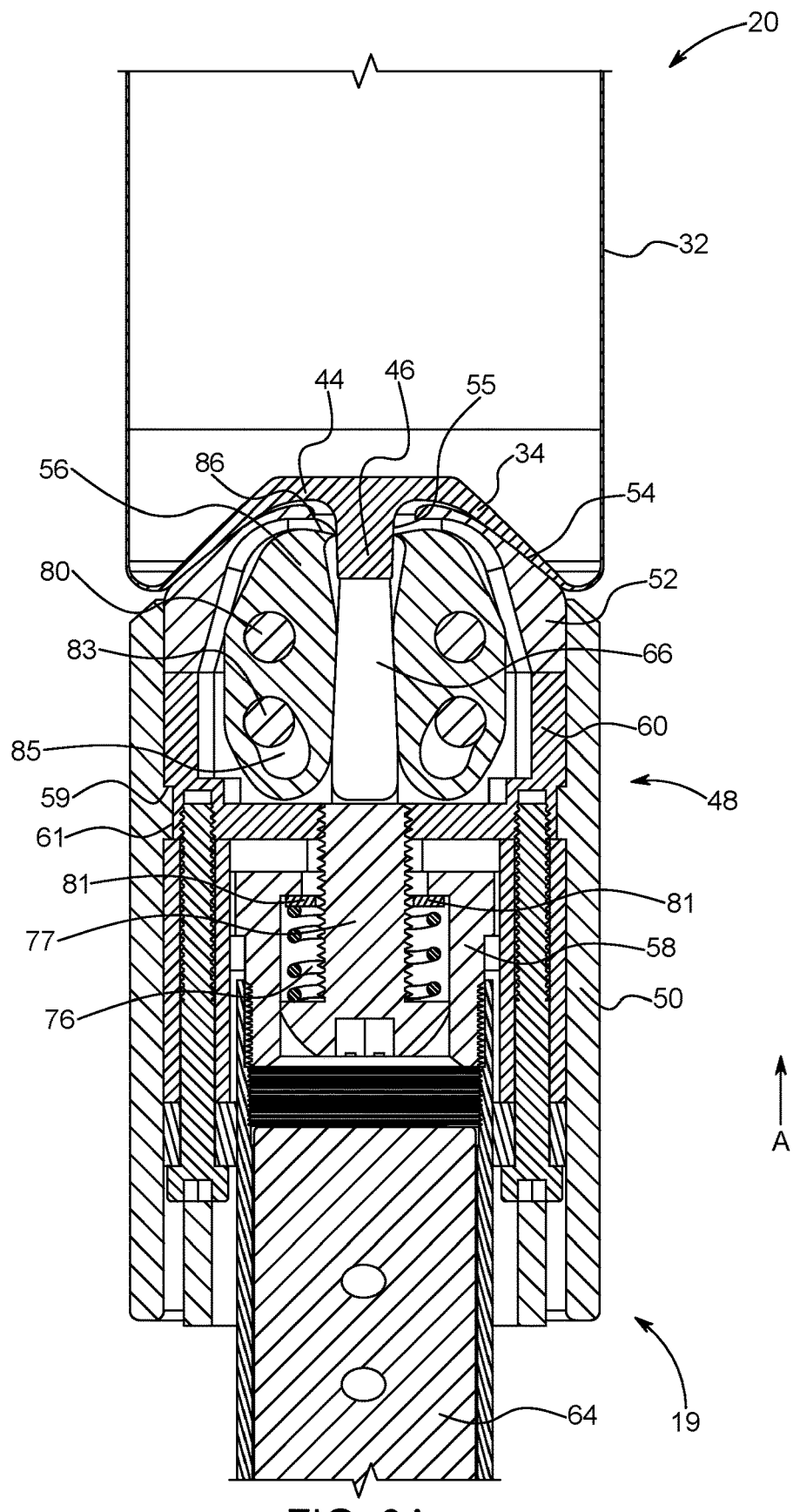
FIG. 3A is a side cross-sectional view of a syringe and a piston having a syringe engagement mechanism in accordance with one example of the present disclosure shown in an open state or configuration.
Figure 3B:
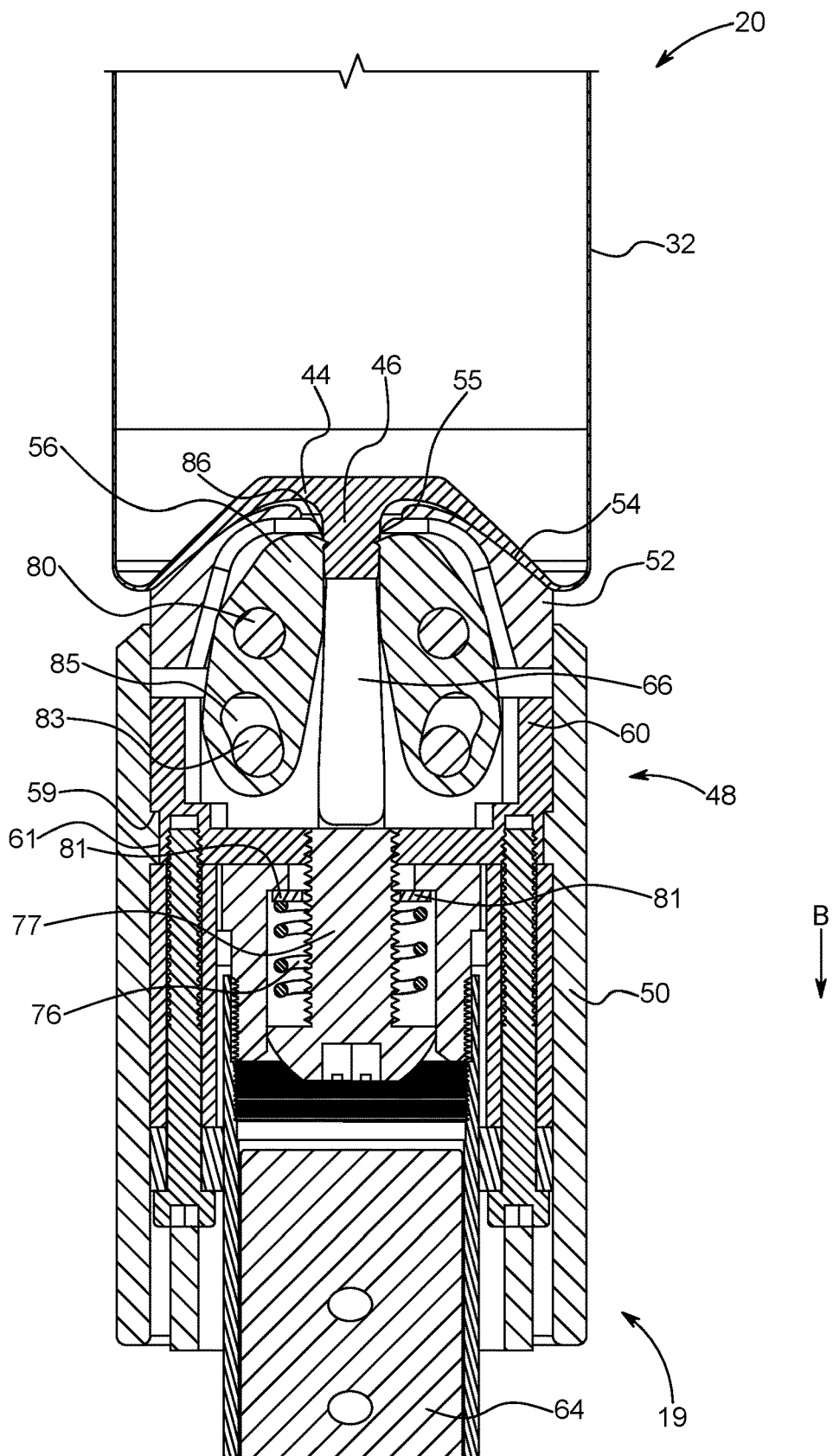
FIG. 3B is a side cross-sectional view of the syringe and the piston with the syringe engagement mechanism of FIG. 3A shown in a closed state or configuration.

FIGS. 3A-3B show the syringe 20 in combination with a syringe engagement mechanism 48 (hereinafter referred to as "engagement mechanism 48") of the piston 19 in accordance with one example of the present disclosure. The components of the syringe 20 shown in FIGS. 3A-3B are substantially similar to the components of the syringe 20 described herein with reference to FIGS. 2A-2B. The engagement portion 46 of the syringe 20 is configured for interacting with one or more engagement pins or surfaces of the engagement mechanism 48 that reversibly move radially inward and outward to engage and disengage, respectively, the engagement portion 46 of the syringe 20.

In various examples, the engagement mechanism 48 has one or more engagement elements 56, such as engagement fingers or surfaces, movable in a radial direction relative to the engagement portion 46 of the syringe 20 between a first position, where the plurality of engagement elements 56 are disengaged from the engagement portion 46 of the syringe 20, and a second position, where the plurality of engagement elements 56 are engaged with the engagement portion 46 of the syringe 20. The engagement mechanism 48 further has a drive mechanism for moving the plurality of engagement elements 56 such as fingers or surfaces between the first position and the second position.

In various examples, the inward/outward radial movement of the engagement elements 56 may be effected by a proximal/distal movement of the piston 19. The engagement elements 56 may be moved radially inward/outward via linear movement, arcuate movement, or a combination of linear and arcuate movement. In various examples, movement of the piston 19 in the proximal direction may cause the engagement elements 56 to contact and lock onto the engagement portion 46 of the syringe 20 so that the distal end 28 of the syringe 20 may be pulled by the piston 19 in a proximal direction to fill the syringe 20 with a medical fluid. Conversely, movement of the piston 19 in a distal direction may cause the engagement elements 56 to be released from contacting the engagement portion 46 of the syringe 20 such that the syringe 20 may be removed from the pressure jacket 16 and the injector 10. In various examples, the piston 19 and/or the engagement elements 56 may be movable by a motor drive, a solenoid drive, a pneumatic drive, a hydraulic drive, or due to an activation of an electro-active polymer, an electromagnetic mechanism, or a nitinol wire or other shape memory alloy-based mechanism, as discussed herein.

With continued reference to FIGS. 3A-3B, the drive mechanism of the engagement mechanism 48 is contained at least partially within the piston 19. In some examples, the drive mechanism has a plurality of parts operatively connected with the piston 19 for moving the plurality of engagement elements 56 between the first position and the second position. In some examples, the drive mechanism has an outer piston sleeve 50 and an abutment section 52 movably received within the outer piston sleeve 50 at a distal end thereof. The outer piston sleeve 50 has a substantially cylindrical structure with an open proximal end and an open distal end. The abutment section 52 has an outer engagement surface 54 at its distal end for engaging at least a portion of the distal surface of the syringe 20 when the piston 19 is advanced distally to engage with the syringe 20. In some examples, the abutment section 52 of the piston 19 may contact at least a portion of the proximal end 30 of the syringe 20, such as the distal surface of the end wall 34. The outer engagement surface 54 may be shaped to correspond to the shape of the end wall 34 such that the outer engagement surface 54 is in surface-to-surface contact with at least a portion of the end wall 34 of the syringe 20. The outer engagement surface 54 and outer piston sleeve 50 define a surface over which the sidewall 32 of the syringe 20 may roll over during a fluid filling or a fluid delivery process due to proximal or distal movement of the piston 19, respectively. An opening 55 is formed in a central portion of the abutment section 52. The opening 55 is configured to receive at least a portion of the engagement portion 46 of the syringe 20 when the abutment section 52 substantially contacts the end wall 34 of syringe 20. Desirably, an inner diameter of the opening 55 is larger than an outer diameter of the widest portion of the engagement portion 46 to allow free insertion of the engagement portion 46 into the opening 55 during distal movement of the piston 19 toward the end wall 34 of syringe 20 or proximal movement of the end wall 34 of syringe 20 toward the piston 19, for example during insertion of the syringe 20 into the pressure jacket 16.

The abutment section 52 is axially movable relative to the outer piston sleeve 50, which is held in a substantially fixed position, for example due to friction between the outer piston sleeve 50 and the piston. The abutment section 52 is movable or slidable in an axial direction relative to the outer piston sleeve 50 to control the state or position of one or more engagement elements 56, such as one or more engagement elements, as described herein. The movement of the abutment section 52 relative to the outer piston sleeve 50 is configured to allow engagement or disengagement of the one or more engagement elements 56 with the engagement portion 46 of the syringe 20.

The piston 19 also has an inner piston sleeve 58 that is axially movable relative to the outer piston sleeve 50. The inner piston sleeve 58 is connected to the abutment section 52 such that movement of the abutment section 52 results in a corresponding movement of the inner piston sleeve 58, and vice versa. A collar 60 is fixedly mounted within the outer piston sleeve 50. In some examples, the collar 60 may have a circumferential recess 59 that is configured to engage a projection 61 protruding from an inner surface of the outer piston sleeve 50. The collar 60 has a longitudinal opening 66 configured to receive at least a portion of the engagement portion 46 of the syringe 20. An inner diameter of the longitudinal opening 66 may be larger than an outer diameter of the widest portion of the engagement portion 46 to allow free insertion of the engagement portion 46 into the longitudinal opening 66.

Figure 4A:
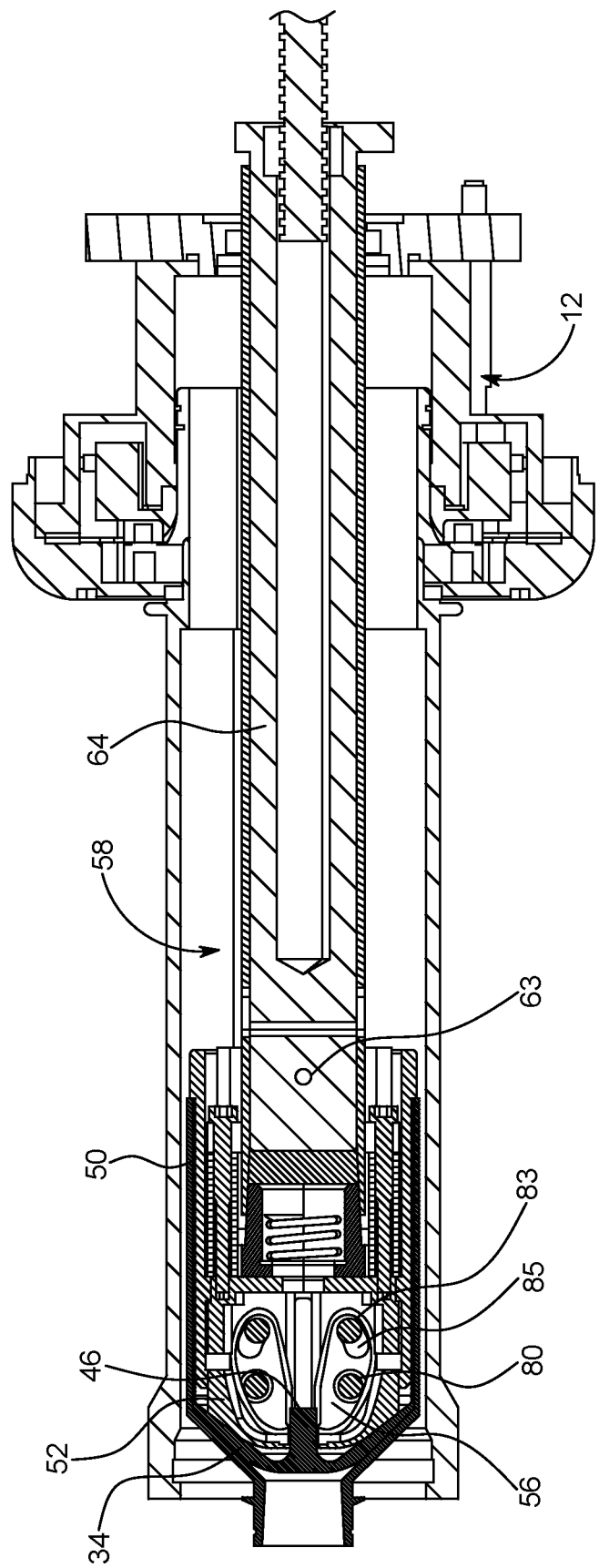
FIG. 4A is a side cross-sectional view of a syringe and a piston having a syringe engagement mechanism in accordance with one example of the present disclosure.
Figure 4B:
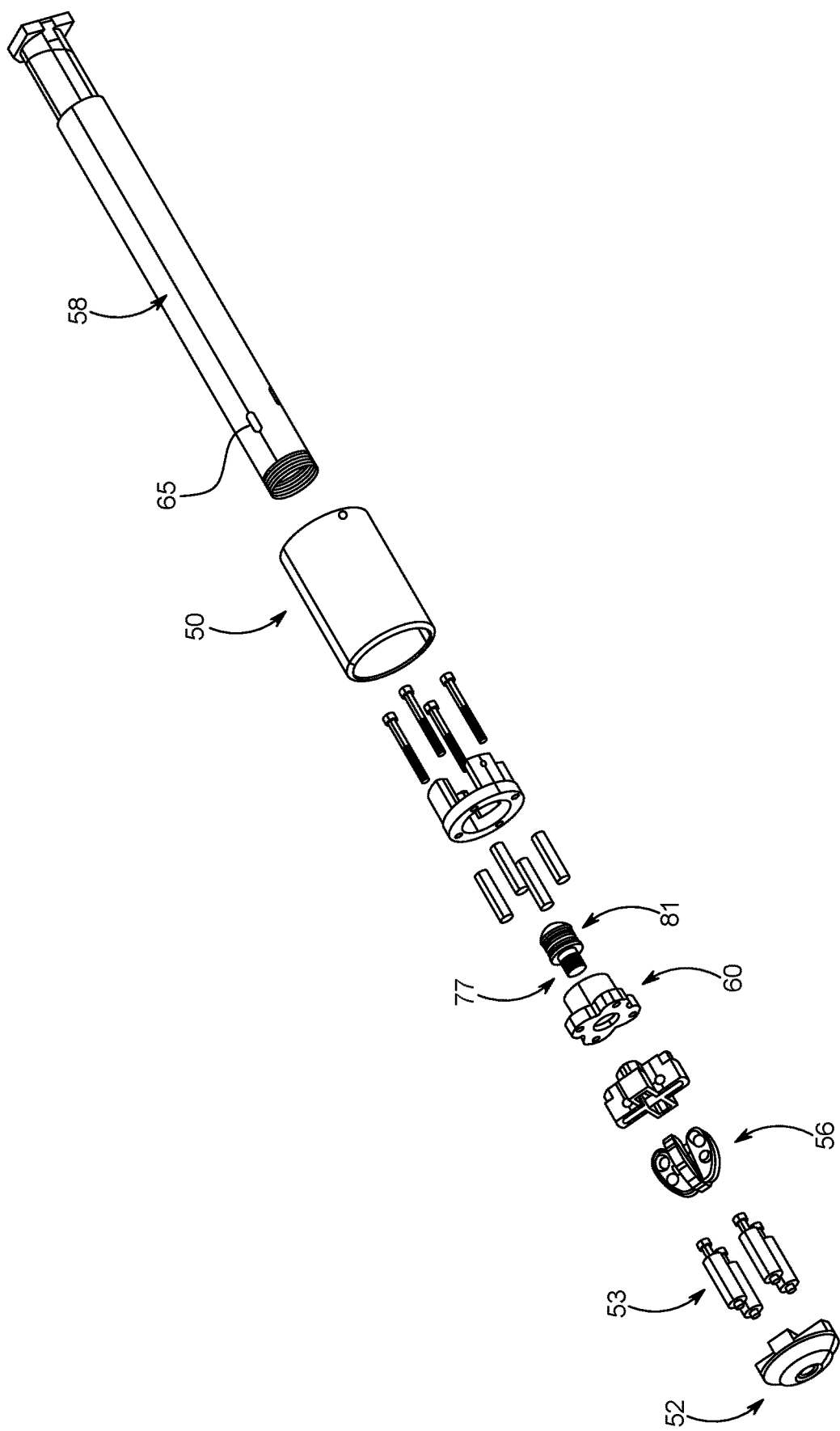
FIG. 4B is an exploded view of the piston and the syringe with the engagement mechanism shown in FIG. 4A.

With continued reference to FIGS. 3A-3B, the abutment section 52 is connected to the inner piston sleeve 58, such as by one or more fasteners 53 (shown in FIG. 4B). In this manner, axial movement of the inner piston sleeve 58 results in a corresponding axial movement of the abutment section 52, and vice versa.

The inner piston sleeve 58 and the abutment section 52 are movable or slidable in an axial direction relative to the outer piston sleeve 50 and the collar 60 with movement of the piston rod 64. For example, the inner piston sleeve 58 and the abutment section 52 may be movable between a first position (FIG. 3A), where the one or more engagement elements 56 are disengaged from the engagement portion 46 of the syringe 20 and a second position (FIG. 3B), wherein the one or more engagement elements 56 are engaged with the engagement portion 46. In some examples, the inner piston sleeve 58 and the abutment section 52 may be biased to the second position by a biasing mechanism, such as a spring 76. A biasing force of the spring 76 may be adjustable by moving the adjustment element 77 in a distal direction (to increase the biasing force) or in a proximal direction (to reduce the biasing force) or vice versa. The adjustment element 77 may be a screw that is threadably engaged with the collar 60 such that the spring 76 is disposed between the head of the screw and the proximal surface of the inner piston sleeve 58 or a washer 81 abutting the proximal surface of the inner piston sleeve 58. The adjustment element 77 desirably extends through an opening in the inner piston sleeve 58. In some examples, inner piston sleeve 58 and the abutment section 52 may be movable or slidable in an axial direction relative to the outer piston sleeve 50 and the collar 60 by way of an electrical, pneumatic, electromagnetic, electroactive polymer-based, shape memory alloy-based or hydraulic actuation mechanism that is operable independent of the direction of movement of the piston 19.

The motion of the abutment section 52 relative to the outer piston sleeve 50 and the collar 60 is limited to allow engagement or disengagement of the one or more engagement elements 56 with the engagement portion 46 of the syringe 20. For example, with reference to FIG. 4A, such relative motion can be limited using a metal rod, polymer rod, or dowel 63 fixed to the piston rod 64, where the dowel 63 passes through and seats within a slot 65 (shown in FIG. 4B) formed in the inner piston sleeve 58 that is directly connected to the collar 60 and the abutment section 52. In some examples, the abutment section 52 may be movable by about 0.100 to 0.150 inches, for example 0.125 inches, with the movement of the inner piston sleeve 58 before the outer piston sleeve 50 and the abutment section 52 move at the same time. In some examples, the inner piston sleeve 58 may be in frictional contact with an inner sidewall of the injector head (not shown). This frictional contact may be used to restrain the inner piston sleeve 58 while allowing the piston rod 64 to move, thereby moving the dowel 63 within the slot 65. Once the dowel 63 engages the proximal or distal end of the slot 65, the frictional force holding the inner piston sleeve 58 is overcome, and the piston rod 64 and the inner piston sleeve 58 may be moved together.

Using this range of movement of the abutment section 52, the collar 60, and the inner piston sleeve 58 relative to the piston rod 64 and the outer piston sleeve 50 (delimited by the longitudinal length of the slot 65), the one or more engagement elements 56 can be moved between the first (open) position (FIG. 3A) and a second (closed) position (FIG. 3B). For example, initial movement of the piston rod 64 in the distal direction may cause the outer piston sleeve 50 to move distally relative to the abutment section 52, which is restrained due to the frictional engagement of the inner piston sleeve 58 with the injector head. Such relative movement of the abutment section 52 and the outer piston sleeve 50 may cause the one or more engagement elements 56 to be retracted in a radially outward direction to allow the syringe 20 to be removed from (on installed on) the injector 10. Conversely, movement of the piston rod 64 in the proximal direction may cause the outer piston sleeve 50 to move proximally relative to the abutment section 52, which is restrained due to the frictional engagement of the inner piston sleeve 58 with the injector head 12. Such relative movement of the abutment section 52 and the outer piston sleeve 50 may cause the one or more engagement elements 56 to be extended in a radially inward direction to engage the engagement portion 46 of the syringe 20 to allow for retraction of the end wall 34 and filling of the syringe 20.

With continued reference to FIGS. 3A-3B, the engagement elements 56 may be at least one, and optionally, a plurality of engagement elements 56 spaced apart circumferentially around a cavity 78 of the inner piston sleeve 58. In some examples, a single engagement element 56 may be configured to contact the engagement portion 46 of the syringe 20. The engagement elements 56 may be spaced apart at equal or unequal angular intervals from one another. The engagement elements 56 may be movable between a first position (FIG. 3A), where the engagement elements 56 do not contact the engagement portion 46 of the syringe 20, and a second position (FIG. 3B), wherein the engagement elements 56 contact the outer surface of the engagement portion 46 of the syringe 20. In some examples, the engagement elements 56 may have a pointed terminal end 86 or tooth configured for at least partially embedding into the material of the engagement portion 46 of the syringe 20 when the engagement elements 56 are positioned in the second position (FIG. 3B). In some examples, the engagement elements 56 may be configured to move from the first position to the second position immediately upon proximal movement of the piston 19. In other examples, the engagement elements 56 may be configured to gradually and progressively move from the first position toward the second position with proximal movement of the piston 19 to continuously increase the gripping force between the engagement element 56 and the engagement portion 46 of the syringe 20. For example, the pointed terminal end 86 may be under a continually increasing force to increase the "bite" with the engagement portion 46 as the piston is moved in a proximal direction.

In some examples, the engagement elements 56 may be pivotable about a pivot pin 80 on the inner piston sleeve 58 to move the engagement element 56 between the first position and the second position. Movement of the engagement elements 56 may be constrained by a pin 83 on the collar 60 that is received within a track 85 on each of the engagement elements 56. The track 85 may be offset from the pivot pin 80 and may be shaped such that it directs the movement of the engagement elements 56 between the first and the second position in an arcuate motion about the pivot pin 80. The engagement elements 56 may also be biased by a biasing mechanism (not shown) to one of the first position and the second position. To move the engagement elements 56 from the second position to the first position, at least a portion of each engagement element 56 may be engaged by the outer engagement surface 54 of the abutment section 52. Because the engagement elements 56 are retained on the collar 60, movement of the abutment section 52 relative to the collar 60 causes the outer engagement surface 54 of the abutment section 52 to contact a distal surface of the engagement elements 56. Continued movement of the abutment section 52 relative to the collar 60 causes the engagement elements 56 to be deflected in a radially outward direction to the first position. In this manner, the engagement elements 56 can be disengaged from contacting the engagement portion 46 of the syringe 20.

Fluid can be delivered from the interior volume 27 of the syringe 20 by driving the piston 19 in the distal direction. If the interior volume 27 of the syringe 20 is fully or partially filled, fluid can be delivered from the syringe 20 by rolling over the sidewall 32 upon itself with the distal movement of the piston 19. During movement of the piston 19 in the distal direction, such as shown by arrow A in FIG. 3A, the abutment section 52 contacts the proximal surface of the end wall 34 of the syringe 20. The abutment section 52 is moved to the first position without rolling over the sidewall 32 of the syringe 20 because the piston rod 64 is moved only to allow the dowel 63 to contact the distal end of the slot 65, thereby moving the engagement elements 56 to the first position. In particular, initial distal movement of the piston 19 urges the outer engagement surface 54 of the abutment section 52 in contact with at least a portion of each engagement element 56 and causes the engagement elements 56 to be deflected in a radially outward direction, thereby opening a clearance space between the engagement elements 56 to allow insertion or removal of the engagement portion 46 of the syringe 20 in the space between the engagement elements 56.

To fill the syringe 20 with fluid, the piston 19 is moved in a proximal direction in the direction of arrow B in FIG. 3B. During movement of the piston 19 in the proximal direction, such as shown by arrow B in FIG. 3B, the abutment section 52 moves relative to the outer piston sleeve 50. During such movement, the engagement elements 56 are moved to the second position toward the engagement portion 46 of the syringe 20 in a radially inward direction by pivoting about the pivot pin 80. The pointed terminal end 86 digs into the outer surface of the engagement portion 46 of the syringe 20 as described herein, to provide a grabbing force between the engagement elements 56 and the engagement portion 46.

FIGS. 5A-5E show the proximal end 30 of the syringe 20 in combination with an engagement mechanism 48 of the piston 19 in accordance with various aspects of the present disclosure. The components of the syringe 20 shown in FIGS. 5A-5E are substantially similar to the components of the syringe 20 described herein with reference to FIGS. 2A-2B. The engagement portion 46 of the syringe 20 is configured for interacting with one or more engagement elements 56, such as one or more engagement elements 56 of the engagement mechanism 48. The engagement elements 56 are configured to move between the first position and the second position by moving radially inward and outward to engage and disengage, respectively, the engagement portion 46 of the syringe 20 in a manner similar to the engagement of the engagement elements 56 of the engagement mechanism 48 with the engagement portion 46 of the syringe 20 described herein with reference to FIGS. 3A-3B.

The engagement mechanism 48 has a drive mechanism 88 for moving the plurality of engagement elements 56 between a first position, wherein the plurality of engagement elements 56 are disengaged from the engagement portion 46 of the syringe 20, and a second position, wherein the plurality of engagement elements 56 are engaged with the engagement portion 46 of the syringe 20. The drive mechanism 88 has an outer piston sleeve 50 and an abutment section 52 fixed relative to the outer piston sleeve 50 at a distal end thereof. The outer piston sleeve 50 has a substantially cylindrical structure with an open proximal end and an open distal end. The abutment section 52 has an outer engagement surface 54 for contacting at least a portion of the proximal end 30 of the syringe 20, such as the end wall 34. An opening 55 is formed in a central portion of the abutment section 52 and is configured to receive at least a portion of the engagement portion 46 of the syringe 20 when the abutment section 52 contacts the proximal end 30 of the syringe 20.

Figure 5B:
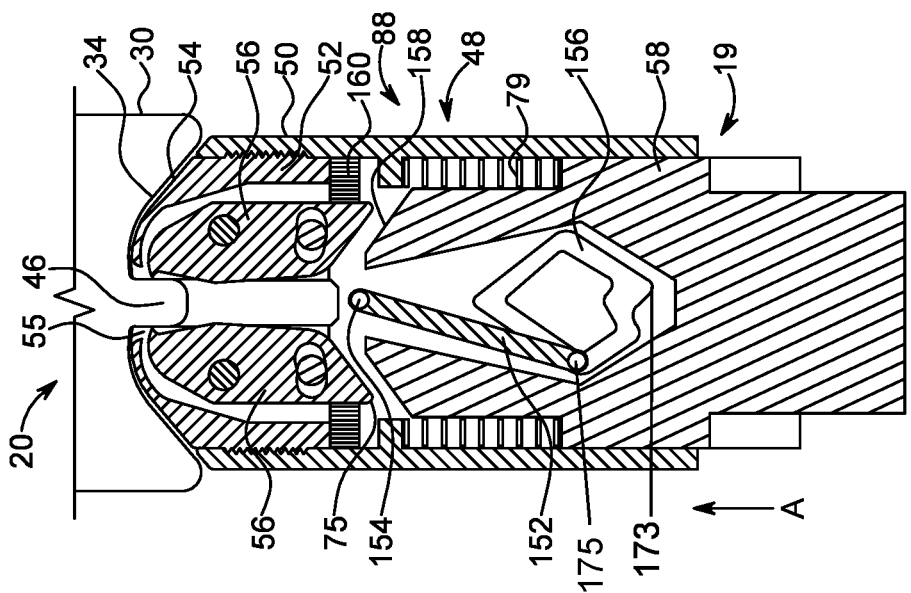
FIGS. 5B-5C are side cross-sectional views of the syringe and the piston with the syringe engagement mechanism of FIG. 5A showing movement of the syringe engagement mechanism from the open state or configuration to a closed state or configuration.
Figure 5A:
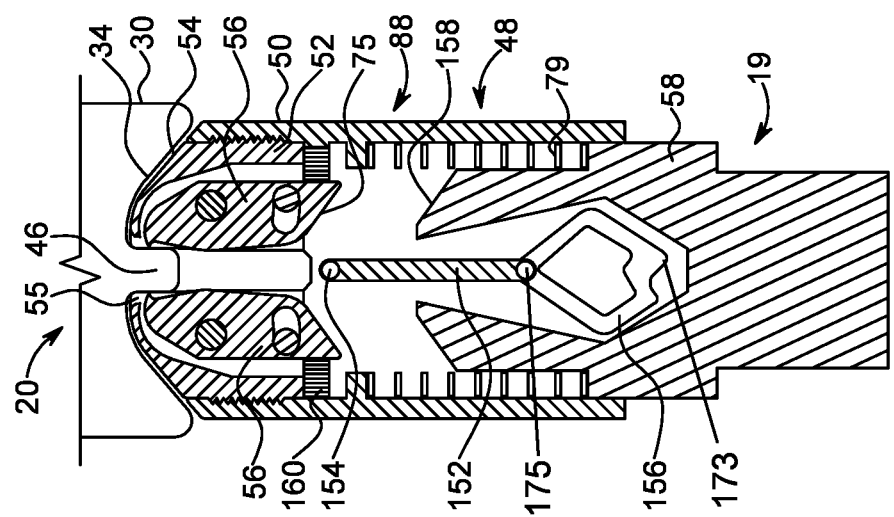
FIG. 5A is a side cross-sectional view of a syringe and a piston having a syringe engagement mechanism in accordance with one example of the present disclosure shown in an open state or configuration.

The drive mechanism 88 further has an inner piston sleeve 58 that is axially movable relative to the outer piston sleeve 50. The inner piston sleeve 58 may be biased to the first position (shown in FIG. 5A) or the second position (not shown) by a biasing mechanism, such as a spring 79. Movement of the inner piston sleeve 58 in a distal direction and toward the outer piston sleeve 50 in a direction of arrow A in FIG. 5B compresses the spring 79 from a first state (FIG. 5A) to a second state (FIG. 5B).

Figure 5E:
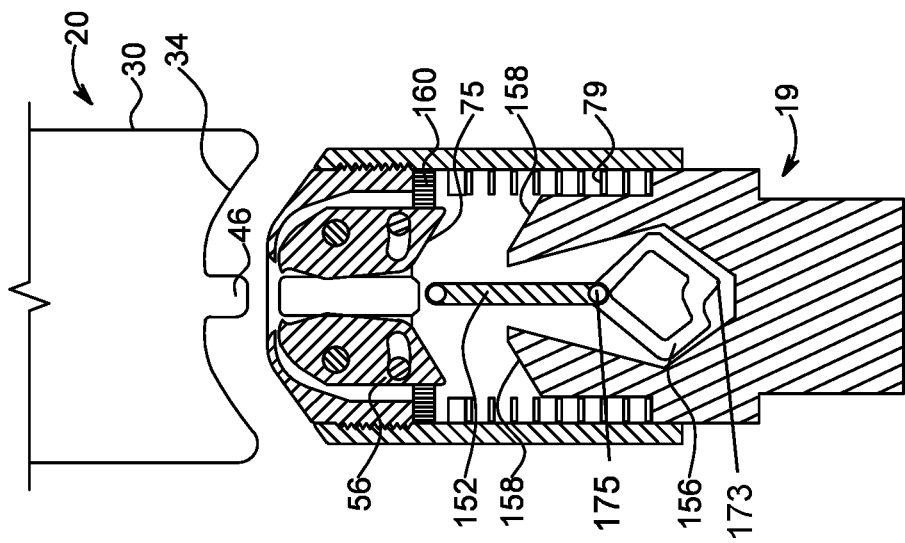
FIGS. 5D-5E are side cross-sectional views of the syringe and the piston with the syringe engagement mechanism of FIG. 5A showing movement of the syringe engagement mechanism from the closed state or configuration to the open state or configuration.
Figure 5D:
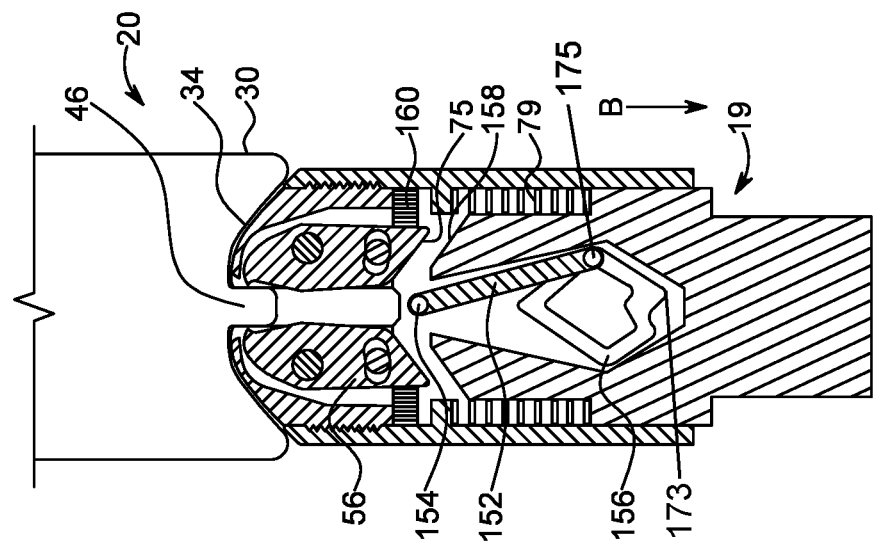
Figure 5C:
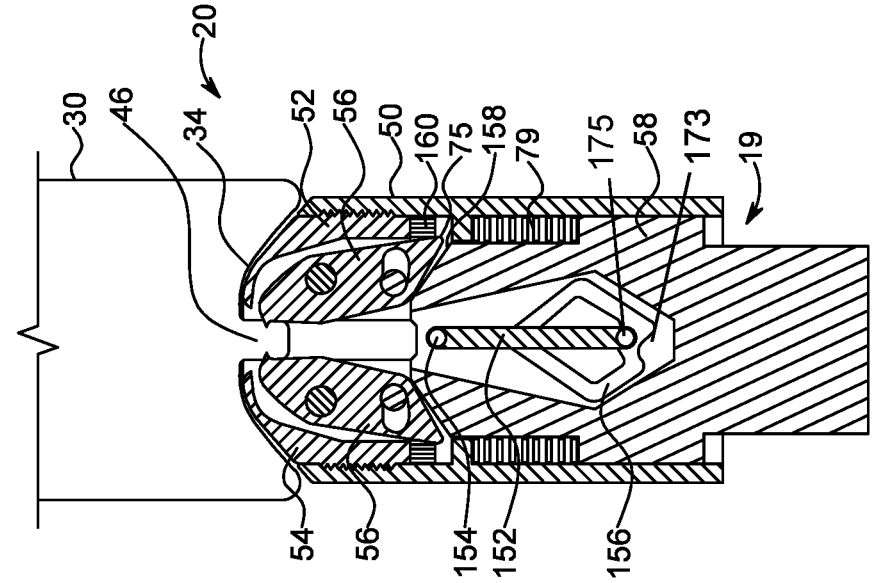

The inner piston sleeve 58 has a bar or a link 152 with a distal end pivotally movable about a pivot point 154 fixed relative to the outer piston sleeve 50 and a second end received within a slot 156. Movement of the inner piston sleeve 58 in the distal direction and toward the outer piston sleeve 50 moves the second end of the link 152 from a distal end toward a proximal end of the slot 156 (FIG. 5B). Continued movement of the inner piston sleeve 58 in the distal direction and toward the outer piston sleeve 50 further moves the link 152 proximally within the slot 156 such that a distal end 158 of the inner piston sleeve 58 contacts a proximal end 75 of the engagement elements 56. The contact between the distal end 158 of the inner piston sleeve 58 with the proximal end 75 of the engagement elements 56 urges the engagement elements 56 in a radially inward direction due to the angled shape of the distal end 158 of the inner piston sleeve 58 (FIG. 5C). As the engagement elements 56 are urged in a radially inward direction, the engagement elements 56 engage the engagement portion 46 of the syringe 20 to allow the end wall 34 of the syringe 20 to be moved in a proximal direction during filling of the syringe 20. As shown in FIG. 5C, the proximal second end of link 152 is secured in the inverted proximal vee 173 of slot 156, reversibly locking the engagement mechanism in the second engaged positon with the engagement elements 56 engaged with the engagement portion 46 of syringe 20, for example by where the pointed terminal ends 86 of the engagement elements 56 having dug into the surface of engagement portion 46. Movement of the engagement elements 56 from the first position (FIG. 5A) to the second position (FIG. 5C) may bias an engagement element biasing mechanism, such as a spring 160, from a first position to a second position. In this position (FIG. 5C), the piston 19 may be retracted in the proximal direction with concomitant unrolling and filling of the syringe 20 with a medical fluid With reference to FIG. 5D, after retraction of the piston 19 to fill syringe 20 with the fluid, delivery of the fluid by distal movement of the piston 19 also disengages the proximal second end 175 of link 152 from the inverted proximal vee 173 of slot 156, at this point movement of the inner piston sleeve 58 in a proximal direction of arrow B after fluid delivery moves the second end of the link 152 from the proximal end toward the distal end of the slot 156, thereby disengaging the distal end 158 of the inner piston sleeve 58 from contacting the proximal end 75 of the engagement elements 56. The engagement elements 56 can then be retracted to the first position (FIG. 5E) due to the restoring force of the spring 160. Movement of the engagement elements 56 from the second position (FIG. 5C) to the first position (FIG. 5D) disengages the engagement elements 56 from the engagement portion 46 of the syringe 20 to allow removal of the syringe 20 (FIG. 5E).

With reference to FIGS. 6A-6C, each engagement element 56 may be movable between the first position, where the engagement element 56 is disengaged from the engagement portion 46 of the syringe 20 (not shown), and a second position, where the engagement element 56 is engaged with the engagement portion 46 of the syringe with axial movement of a drive mechanism 88. The engagement element 56 shown in FIGS. 6A-6C may have the same structure as the engagement elements 56 shown in FIGS. 3A-3B including pointed terminal ends 86 or teeth for digging into the surface of engagement portion 46 to provide a secure connection between the engagement element 56 and engagement portion 46. The engagement element 56 may be pivotable about a pivot pin 80. Movement of the engagement element 56 may be constrained by a pin 83 that is received within a track 85. The track 85 is offset from the pivot pin 80 and may be shaped such that it directs the movement of the engagement elements 56 from the first to the second position in an arcuate motion about the pivot pin 80. The drive mechanism 88 may be operated by distal and proximal movement of the piston or may be an activatable drive mechanism, for example a mechanism that is activated by one or more of a linear electric motor or actuator, a rotary electric motor or actuator, a solenoid, a pneumatic mechanism, a hydraulic mechanism, an electromagnetic mechanism, an electroactive polymer mechanism, a shape-memory alloy (such as nitinol wire)-based mechanism, and any combination thereof.

With continued reference to FIGS. 6A-6C, according the various aspects, the drive mechanism 88 may be formed on or within the piston 19 (not shown). According to certain aspects, the drive mechanism 88 may have a first sloped surface 88a and a second sloped surface 88b axially offset from the first sloped surface 88a. The first and second sloped surfaces 88a, 88b are angled in a direction pointing radially and proximally away from the engagement portion 46. The drive mechanism 88 is movable from a first position (shown in FIG. 6A) to a second position (shown in FIG. 6B) via axial movement in a direction of arrow G in FIG. 6A and from the second position to the first position by axial movement in a direction opposite of arrow G. In the first position, the first sloped surface 88a is axially offset from a proximal end 75 of the engagement element 56. With distal movement of the drive mechanism 88, the first sloped surface 88a contacts the proximal end 75 of the engagement element 56, forcing the proximal end 75 to slide along the first sloped surface 88a. Such sliding movement of the proximal end 75 of the engagement element 56 causes the engagement element 56 to pivot about the pivot pin 80 and the pin 83 to move from a first end to a second end of the track 85. The pivoting movement of the engagement element 56 results in the pointed terminal end 86 moving radially inward such that it contacts the engagement portion 46 of the syringe (FIG. 6B). Continued distal movement of the drive mechanism 88 engages the proximal end 75 of the engagement element 56 with the second sloped surface 88b (FIG. 6C). Such engagement between the proximal end 75 of the engagement element 56 and the second sloped surface 88b further forces the pointed terminal end 86 to move radially inward such that the pointed terminal end 86 digs into and becomes embedded into the material of the engagement portion 46 of the syringe. With such engagement, the piston (not shown), can be moved proximally and retract the engagement portion 46 and distal end 28 of syringe 20 (see FIGS. 2A-2B), to fill the syringe with fluid, as described herein with reference to FIGS. 3A-3B.

Figure 7A:
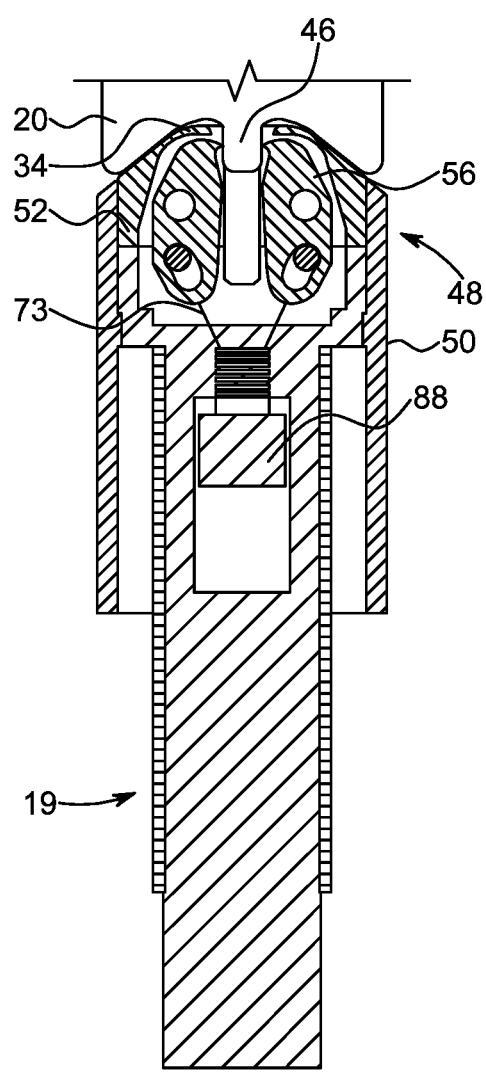
FIG. 7A is a side cross-sectional view of a syringe and a piston having a syringe engagement mechanism in accordance with one example of the present disclosure shown in an open state or configuration.
Figure 7B:
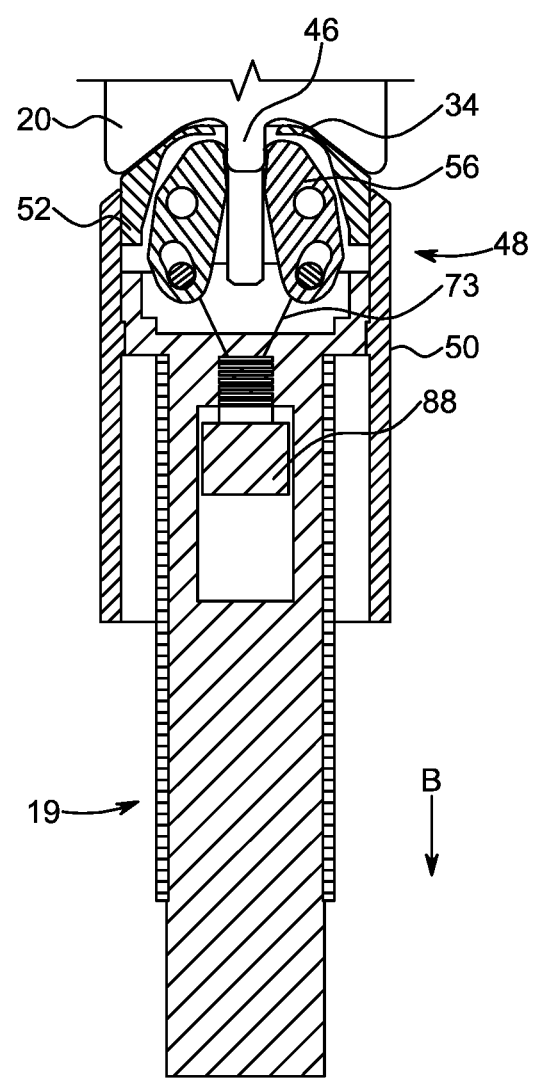
FIG. 7B is a side cross-sectional view of the syringe and the piston with the syringe engagement mechanism of FIG. 7A shown in a closed state or configuration.

FIGS. 7A-7B show the proximal end 30 of the syringe 20 in combination with an engagement mechanism 48 of the piston 19 in accordance with various examples of the present disclosure. The components of the syringe 20 shown in FIGS. 7A-7B are substantially similar to the components of the syringe 20 described herein with reference to FIGS. 2A-2B. The engagement portion 46 of the syringe 20 is configured for interacting with one or more engagement elements, such as one or more engagement elements 56 of the engagement mechanism 48. The engagement elements 56 are configured to move radially inward and outward to engage and disengage, respectively, the engagement portion 46 of the syringe 20 in a manner similar to the engagement of the engagement elements 56 of the engagement mechanism 48 with the engagement portion 46 of the syringe 20 described herein with reference to FIGS. 3A-3B. According to various embodiments, the inward/outward movement of the engagement elements 56 in FIGS. 7A-7B may occur independently of the proximal/distal movement of the piston 19 due to operation of a drive mechanism 88.

With continued reference to FIGS. 7A-7B, the drive mechanism 88 is configured for controlling the movement of the engagement elements 56 between a first, or disengaged position (FIG. 7A) and a second, engaged position (FIG. 7B). The drive mechanism 88 is disposed within the outer piston sleeve 50. Similar to the piston 19 shown in FIGS. 3A-3B, the piston 19 in FIGS. 7A-7B has the abutment section 52 at a distal end thereof for engaging with the end wall 34 of the syringe 20. Activation of the drive mechanism 88 moves the abutment section 52 relative to the outer piston sleeve 50, such as by advancing the abutment section 52 in a distal direction. Such movement of the abutment section 52 moves the engagement elements 56 in a radially inward direction to engage the engagement portion 46 of the syringe 20. The engagement elements 56 may be movable between a first position (FIG. 7A), where the engagement elements 56 do not contact the engagement portion 46 of the syringe 20, and a second position (FIG. 7B), wherein the engagement elements 56 contact the outer surface of the engagement portion 46 of the syringe 20 and the pointed terminal end 86 digs into and becomes embedded into the material of the engagement portion 46. In some examples, radial movement of the engagement elements 56 may further be a function of proximal movement of the piston 19 in a direction of arrow B shown in FIG. 7B. That is, as the piston 19 is moved further in the proximal direction, the force of the "bite" or radially inward force between the engagement elements 56 and the pointed terminal ends 86 with the engagement portion 46 increases so that any proximal slipping of the pointed terminal ends 86 through the material of the engagement portion 46 is counteracted. For example, during initial movement of the piston 19 in the proximal direction, the engagement elements 56 may be advanced radially inward to an initial contact position where the engagement elements 56 contact the outer surface of the engagement portion 46 of the syringe 20. With continued proximal movement of the piston 19, the engagement elements 56 may continue to move in a radially inward direction from the initial contact position such that the engagement elements 56 and pointed terminal ends 86 dig into or become embedded within the material of the engagement portion 46 of the syringe 20 to increase the holding force on the syringe 20. The engagement elements 56 may move to a final contact position having a maximum radial displacement from the initial contact position at a final proximal position of the piston 19. In other examples, radial movement of the engagement elements 56 may be controlled independent of the proximal or distal movement of the piston 19. A linkage mechanism 73 connects the drive mechanism 88 with the engagement elements 56 to effect the movement of the engagement elements 56 with actuation of the drive mechanism 88.

Various embodiments of the drive mechanism 88 may be mechanically, electrically, pneumatically, and/or hydraulically operated. For example, the drive mechanism 88 may have an electric or electromechanical mechanism, such as a linear or rotary electric motor, or a solenoid. In other examples, the drive mechanism 88 may be activated/deactivated by an electromagnetic mechanism, an electroactive polymer mechanism, or a shape-memory alloy (such as nitinol wire)-based mechanism. Various combinations of these mechanisms is also contemplated at being within the scope of the present disclosure. In some examples, the drive mechanism 88 may be selectively energized, such as during proximal or distal movement of the piston 19. In other examples, the drive mechanism 88 may be constantly energized, regardless of whether the piston 19 is stationary, or moving in the proximal or distal direction.

In certain embodiments, movement of the drive mechanism 88 relative to the outer piston sleeve 50 is configured to allow engagement or disengagement of the engagement elements 56 with the engagement portion 46 of the syringe 20. In some examples, movement of the abutment section 52 in a proximal direction relative to the outer piston sleeve 50 and away the syringe 20 may result in the drive mechanism 88 retracting the engagement elements 56 in a radially outward direction to allow the syringe 20 to be removed from the injector 10. Conversely, movement of the abutment section 52 in a distal direction relative to the outer piston sleeve 50 and toward the syringe 20 may result in the drive mechanism 88 extending the engagement elements 56 in a radially inward direction to engage the engagement portion 46 of the syringe 20. In other examples, operation or activation of the drive mechanism 88 may be independent of the movement of the abutment section 52, the outer piston sleeve 50, and/or the piston 19, such that the engagement elements 56 can be selectively moved between the first position and the second position based upon operation of the drive mechanism 88 only.

Figure 8C:
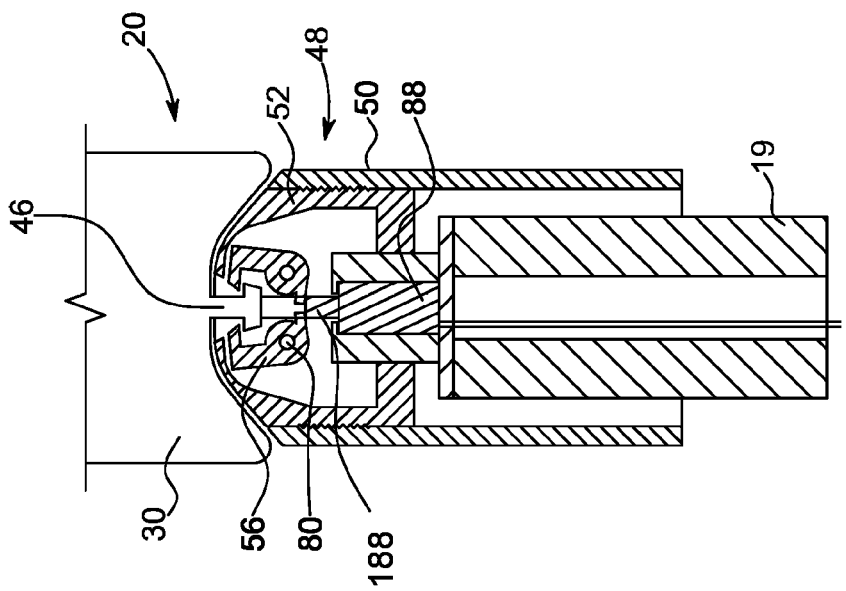
FIG. 8C is a side cross-sectional view of the syringe and the piston with the syringe engagement mechanism of FIG. 8A shown in the open state or configuration.
Figure 8B:
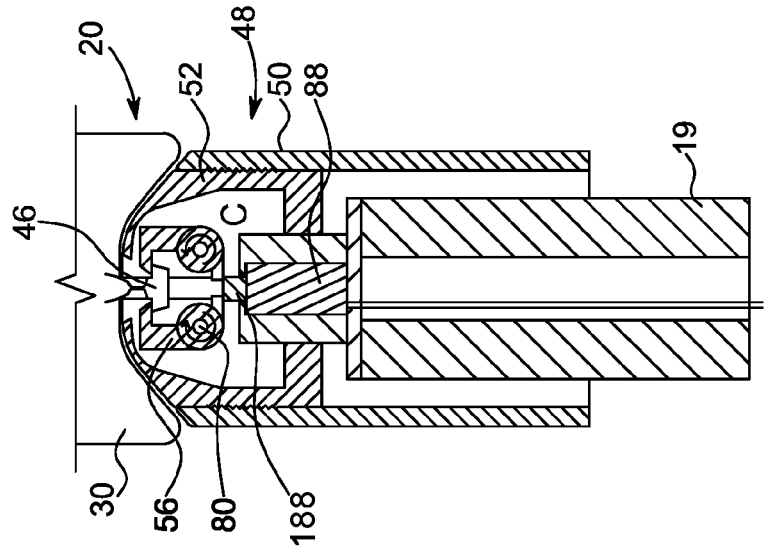
FIG. 8B is a side cross-sectional view of the syringe and the piston with the syringe engagement mechanism of FIG. 8A shown in a closed state or configuration.
Figure 8A:
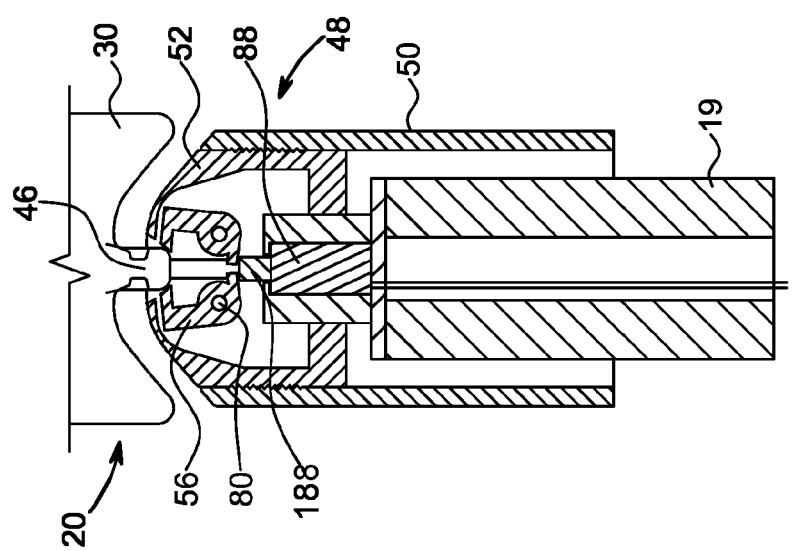
FIG. 8A is a side cross-sectional view of a syringe and a piston having a syringe engagement mechanism in accordance with one example of the present disclosure shown in an open state or configuration.

FIGS. 8A-8C show the proximal end 30 of the syringe 20 in combination with an engagement mechanism 48 of the piston 19 in accordance with various examples of the present disclosure. The components of the syringe 20 shown in FIGS. 8A-8C are substantially similar to the components of the syringe 20 described herein with reference to FIGS. 2A-2B. The engagement portion 46 of the syringe 20 is configured for interacting with one or more engagement elements, such as one or more engagement elements 56 of the engagement mechanism 48. The engagement elements 56 are configured to move radially inward and outward to engage and disengage, respectively, the engagement portion 46 of the syringe 20 in a manner similar to the movement of the engagement elements 56 relative to the engagement portion 46 of the syringe 20 described herein with reference to FIGS. 3A-3B.

Radial movement of the engagement elements 56 may be controlled independently of the proximal or distal movement of the piston 19. For example, after the piston 19 is advanced in a distal direction such that the abutment section 52 contacts the proximal end 30 of the syringe 20, the engagement elements 56 may be advanced radially inward with actuation of the drive mechanism 88, such as a solenoid operated piston 188. In some examples, the drive mechanism 88 may rotate each of the engagement elements 56 about the pivot pin 80 in a direction of arrows C in FIG. 8B to engage (FIG. 8A) or disengage (FIG. 8C) the engagement elements 56 from the engagement portion 46. The engagement elements 56 may be biased to move in a radially inward direction from their initial position to a final position due to a biasing mechanism such as a spring. Movement of the engagement elements 56 radially inwardly may cause the material of the engagement portion 46 of the syringe 20 is at least partially deformed. For example, the engagement elements 56 may be at least partially embedded into the material of the engagement portion 46 such that the post of the engagement portion 46 is deformed from its initial configuration (FIG. 8A) to a final configuration (FIGS. 8B-8C) due to the force applied by the biasing mechanism. In some examples, the deformed engagement portion 46 may have an inverted "T" shape, wherein the engagement elements 56 engage at least a portion of the deformed engagement portion 46. Activation of the solenoid operated piston 188 moves the solenoid operated piston 188 in a distal direction, causing the engagement elements to move against the biasing force of the biasing mechanism and actively engage or disengage from the engagement portion 46.

FIGS. 9A-9D show the proximal end 30 of the syringe 20 in combination with an engagement mechanism 48 of the piston 19 in accordance with other examples of the present disclosure. The components of the syringe 20 shown in FIGS. 9A-9D are substantially similar to the components of the syringe 20 described herein with reference to FIGS. 2A-2B. The engagement portion 46 of the syringe 20 is configured for interacting with one or more engagement elements, such as one or more engagement elements 56, of the engagement mechanism 48. The engagement elements 56 are configured to move radially inward and outward to engage and disengage, respectively, the engagement portion 46 of the syringe 20 in a manner similar to the movement of the engagement elements 56 relative to the engagement portion 46 of the syringe 20 described herein with reference to FIGS. 3A-3B.

With continued reference to FIGS. 9A-9D, the engagement mechanism 48 has a drive mechanism 88 for moving the plurality of engagement elements 56 between a first position, wherein the plurality of engagement elements 56 are disengaged from the engagement portion 46 of the syringe 20, and a second position, wherein the plurality of engagement elements 56 are engaged with the engagement portion 46 of the syringe 20. The engagement mechanism 48 has an outer piston sleeve 50 and an abutment section 52 fixed relative to the outer piston sleeve 50 at a distal end thereof. The outer piston sleeve 50 has a substantially cylindrical structure with an open proximal end and an open distal end. The abutment section 52 has an outer engagement surface 54 for contacting at least a portion of the proximal end 30 of the syringe 20, such as the end wall 34. An opening 55 is formed in a central portion of the abutment section 52 and is configured to receive at least a portion of the engagement portion 46 of the syringe 20 when the abutment section 52 contacts the syringe 20.

Figure 9A:
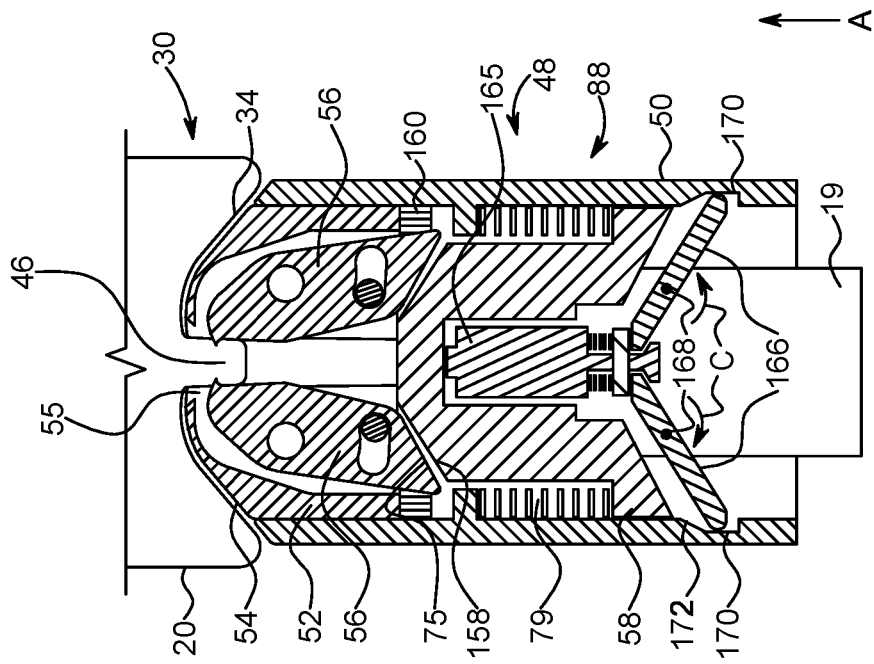
FIG. 9A is a side cross-sectional view of a syringe and a piston having a syringe engagement mechanism in accordance with one example of the present disclosure shown in an open state or configuration.
Figure 9B:
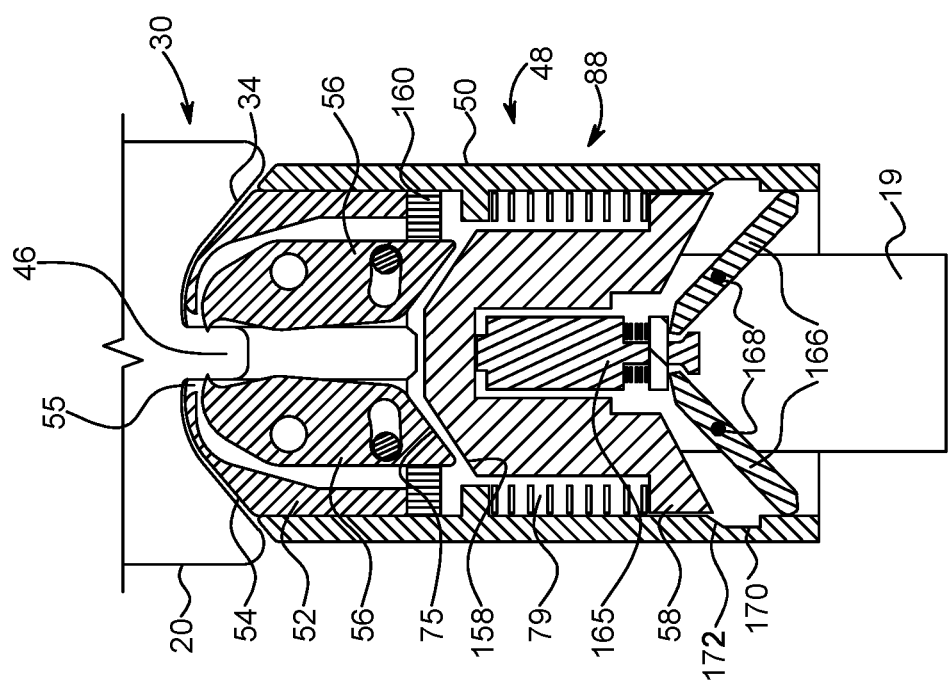
FIG. 9B is a side cross-sectional view of the syringe and the piston with the syringe engagement mechanism of FIG. 9A shown in a closed state or configuration.

The engagement mechanism 48 further has an inner piston sleeve 58 that is axially movable relative to the outer piston sleeve 50. The inner piston sleeve 58 may be biased to a first position (shown in FIG. 9A) by a biasing mechanism, such as a spring 79. Movement of the inner piston sleeve 58 in a distal direction and relative to the outer piston sleeve 50 in a direction of arrow A in FIG. 9B compresses the spring 79 from a first state (FIG. 9A) to a second state (FIG. 9B).

Figure 9D:
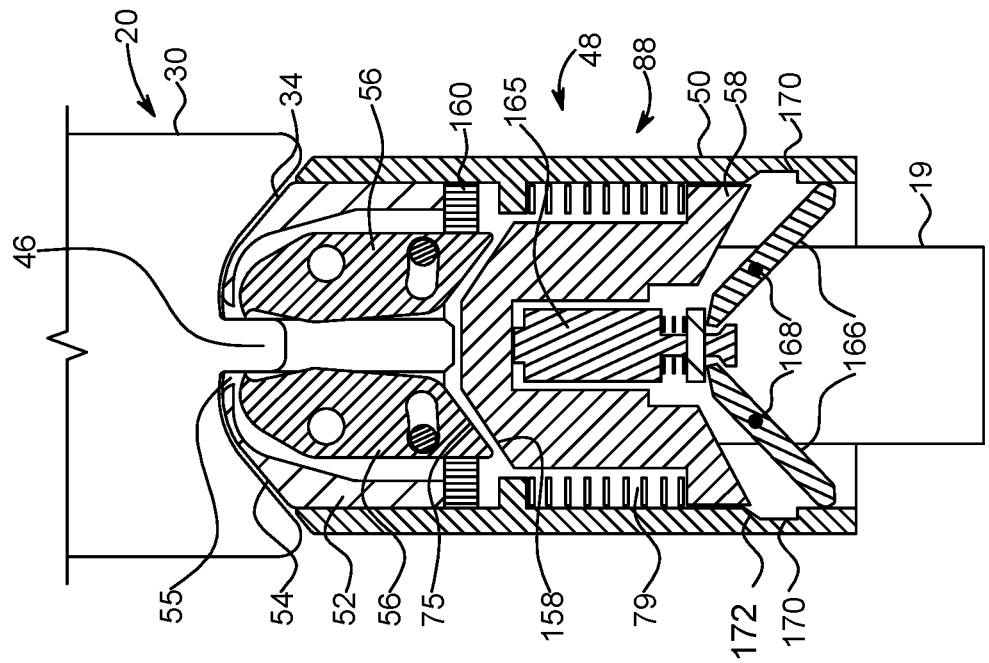
FIGS. 9C-9D are side cross-sectional views of the syringe and the piston with the syringe engagement mechanism of FIG. 9A showing movement of the syringe engagement mechanism from the closed state or configuration to the open state or configuration.
Figure 9C:
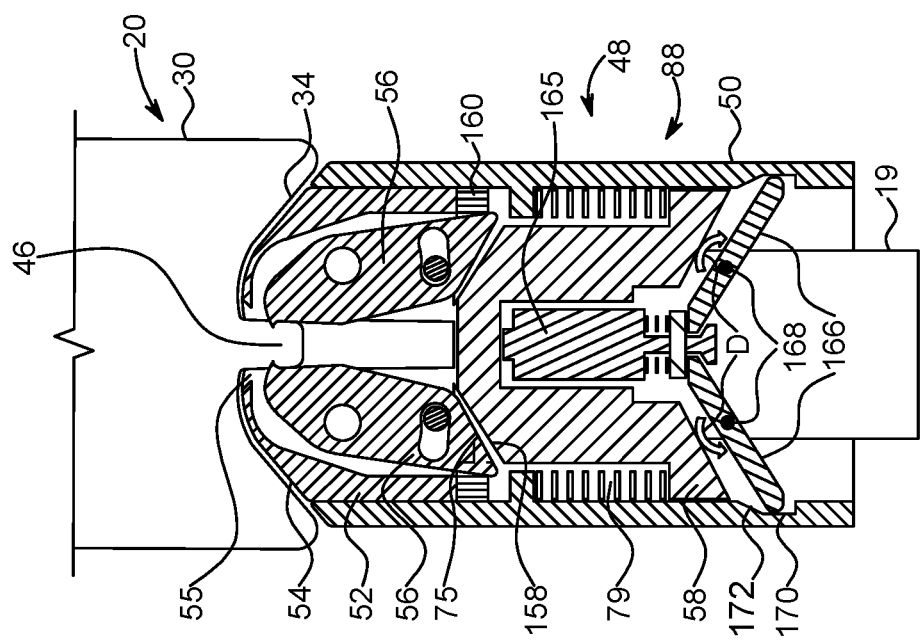

With continued reference to FIGS. 9A-9D, the drive mechanism 88 has a solenoid 165 having a two or more locking levers 166 at a proximal end of the solenoid 165. Each locking lever 166 is rotatably mounted on a pivot pin 168 such that each locking lever 166 is rotatable about the pivot pin 168. In some examples, the locking levers 166 may be biased in a radially outward direction by a biasing mechanism (not shown). Proximal ends of the locking levers 166 are configured for being received within a groove 170 on an inside surface of the outer piston sleeve 50. Movement of the inner piston sleeve 58 in the distal direction relative to the outer piston sleeve 50, such as due to movement of the piston 19, moves the locking levers 166 to a position where the locking levers 166 can be expanded radially outward by rotating in a direction of arrow C in FIG. 9B when the locking levers 166 are axially aligned within the groove 170. Movement of the locking levers 166 in a radially outward direction into the groove 170 locks the locking levers 166, and thereby the inner piston sleeve 58 from moving proximally relative to the outer piston sleeve 50. Distal movement of the inner piston sleeve 58 relative to the outer piston sleeve 50 is permitted due to an angled surface 172 of the groove 170 deflecting the proximal ends of the locking levers 166 in a radially inward direction (FIG. 9C).

Concurrent with movement of the inner piston sleeve 58 in the distal direction relative to the outer piston sleeve 50, the inner piston sleeve 58 urges a distal end 158 of the inner piston sleeve 58 to contact a proximal end 75 of the engagement elements 56. Contact between the distal end 158 of the inner piston sleeve 58 with the proximal end 75 of the engagement elements 56 urges distal ends of the engagement elements 56 and the pointed terminal ends 86 in a radially inward direction due to the angled shape of the distal end 158 of the inner piston sleeve 58 with the proximal end 75 of the engagement elements 56 (FIG. 9C). As the engagement elements 56 are urged in a radially inward direction, the engagement elements 56 engage the engagement portion 46 of the syringe 20 to allow the end wall 34 of the syringe 20 to be moved in a proximal direction during filling of the syringe 20 and in a distal direction during a fluid delivery from syringe 20. Movement of the engagement elements 56 from the first position (FIG. 9A) to the second position (FIG. 9C) may bias an engagement element biasing mechanism, such as a spring 160, from a first position to a second position.

With reference to FIG. 9D, when the solenoid 165 is energized, the locking levers 166 are rotated about the pivot pins 168 radially inward in a direction of arrow D, thereby disengaging the proximal ends of the locking levers 166 from the grooves 170. This allows the inner piston sleeve 58 to be moved proximally relative to the outer piston sleeve 50, thereby disengaging the distal end 158 of the inner piston sleeve 58 from contacting the proximal end 75 of the engagement elements 56. The engagement elements 56 are subsequently retracted to the first position (FIG. 9D), for example due to the restoring force of the spring 160. Movement of the engagement elements 56 from the second position (FIG. 9C) to the first position (FIG. 9D) disengages the engagement elements 56 from the engagement portion 46 of the syringe 20 to allow removal of the syringe 20.

FIGS. 10A-10D show the proximal end 30 of the syringe 20 in combination with an engagement mechanism 48 of the piston 19 in accordance with various aspects of the present disclosure. The components of the syringe 20 shown in FIGS. 10A-10D are substantially similar or identical to the components of the syringe 20 described herein with reference to FIGS. 2A-2B. The engagement portion 46 of the syringe 20 is configured for interacting with one or more surfaces of the engagement mechanism 48 that engage and disengage the engagement portion 46 of the syringe 20 with movement of a central rod 37. For example, the engagement portion 46 of the syringe 20 is configured for interacting with one or more engagement elements 56, such as one or more engagement arms 68, of the engagement mechanism 48 that move radially inward and outward to engage and disengage, respectively, the engagement portion 46 of the syringe 20.

In various examples, the engagement mechanism 48 has the one or more engagement elements 56, such as the one or more engagement arms 68, movable in a radial direction relative to the engagement portion of the syringe 20 between a first position, where the engagement arms 68 are disengaged from the engagement portion 46 of the syringe 20, and a second position, where the engagement arms 68 are engaged with the engagement portion 46 of the syringe 20. The engagement mechanism 48 further has a drive mechanism 88 for moving the engagement arms 68 between the first position and the second position.

The engagement arms 68 each include a proximal end 69 configured for interacting with a central rod 37 operably connected to the piston 19. A distal end 70 of the engagement arms 68 is configured for engagement with the engagement portion 46 of the syringe 20. Each arm 68 is pivotable about a pivot pin 80 between a first position, where the engagement portion 46 of the syringe 20 can be freely inserted into and removed from the space between the arms 68, a second position, such as an opening 55 in an outer engagement surface 54 of the piston 19, wherein the distal end 70 of the arms 68 engages at least a portion of the engagement portion 46 of the syringe 20, for example by digging one or more pointed terminal ends 86 into a surface of the engagement portion 46. In the example shown in FIGS. 10A-10D, the central rod 37 is configured to move relative to the piston 19 in the proximal/distal direction. FIGS. 10A-10B show the central rod 37 in a proximally retracted position, such that the engagement arms 68 are disengaged from the engagement portion 46 of the syringe 20. FIGS. 10C-10D show the central rod 37 in a distally extended position, such that a widened portion of the central rod 37 abuts the proximal ends 69 of the engagement arms 68, causing the engagement arms 68 to rotate about respective pivot pins 80 to engage the distal end 70 of the engagement arms 68 with the engagement portion 46 of the syringe 20. In various examples, proximal/distal movement of the central rod 37 may be effected by and/or dependent upon proximal/distal movement of the piston 19. In other examples, proximal/distal movement of the central rod 37 may be independent of the proximal/distal movement of the piston 19, such as by a drive mechanism 88 substantially similar or identical to the drive mechanism 88, such as any of the drive mechanisms described herein.

With reference to FIG. 10B, the central rod 37 has a proximal portion 37a having a first diameter that is larger than a space between the engagement arms 68 and a distal portion 37b having a second diameter that is smaller or equal to the space between the engagement arms 68, when the engagement arms 68 are in the first position. The proximal and distal portions 37a, 37b may be connected by a ramp 37c. The engagement arms 68 are positioned in the first position away from the engagement portion 46 of the syringe 20 when the distal portion 37b of the central rod 37 is positioned between the proximal ends 69 of the engagement arms 68. With a distal movement of the central rod 37, such as due to actuation of the drive mechanism 88, the ramp 37c engages the proximal ends 69 of the engagement arms 68 to spread the proximal ends 69 radially apart from each other to allow the proximal portion 37a of the central rod 37 to be inserted therebetween. Spreading of the proximal ends 69 of the engagement arms 68 moves the distal ends 70 thereof radially closer together and into engagement with the engagement portion 46 of the syringe 20 into the second positon. Proximal retraction of the central rod 37 reverses the process and disengages the distal ends 70 from the engagement portion 46 of the syringe 20 to allow removal of the syringe 20 from the injector. In some examples, a biasing mechanism, such as a spring, may be provided to bias the engagement arms to the first (open) position or the second (closed) position.

Figure 10E:
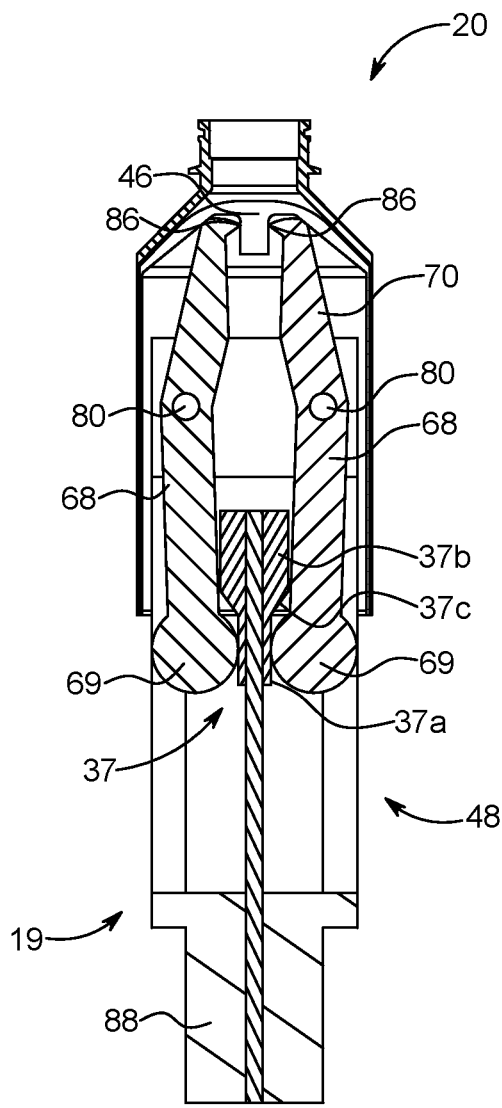
FIG. 10E is a side cross-sectional view of a syringe and a piston having a syringe engagement mechanism in accordance with one example of the present disclosure shown in an open state or configuration.
Figure 10F:
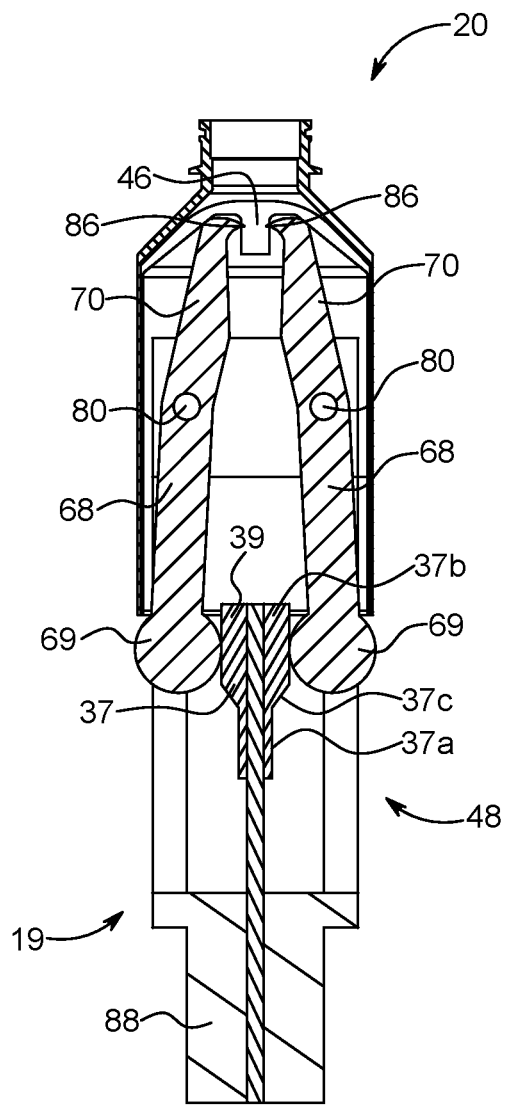
FIG. 10F is a side cross-sectional view of the syringe and the piston with the syringe engagement mechanism shown in FIG. 10E with the syringe engagement mechanism shown in a closed state or configuration.

According to other aspects, such as shown in FIGS. 10E-10F, the central rod 37 has a proximal portion 37a having a first diameter that is smaller than a space between the engagement arms 68 and a distal portion 37b having a second diameter that is larger or equal to the space between the engagement arms 68. The proximal and distal portions 37a, 37b may be connected by the ramp 37c. The engagement arms 68 are positioned away from the engagement portion 46 of the syringe 20 when the proximal portion 37a of the central rod 37 is positioned between the proximal ends 69 of the engagement arms 68. With a proximal movement of the central rod 37, such as due to actuation of the drive mechanism 88, the ramp 37c engages the proximal ends 69 of the engagement arms 68 to spread the proximal ends 69 apart from each other to allow the distal portion 37b of the central rod 37 to be inserted therebetween. Spreading of the proximal ends 69 of the engagement arms 68 moves the distal ends 70 thereof closer together and into engagement with the engagement portion 46 of the syringe 20. Distal extension of the central rod 37 reverses the process and disengages the distal ends 70 from the engagement portion 46 of the syringe 20 to allow removal of the syringe 20 from the injector.

In further examples, the central rod 37 may have a conical shape without a distinct ramp 37c between the proximal and distal portions 37a, 37b, respectively. The central rod 37 may be movable in a proximal direction with actuation of the drive mechanism 88 to engage the engagement arms 68 with the engagement portion 46 of the syringe 20. In other examples, the central rod 37 may be movable in a distal direction with actuation of the drive mechanism 88 to engage the engagement arms 68 with the engagement portion 46 of the syringe 20.

Figure 10G:
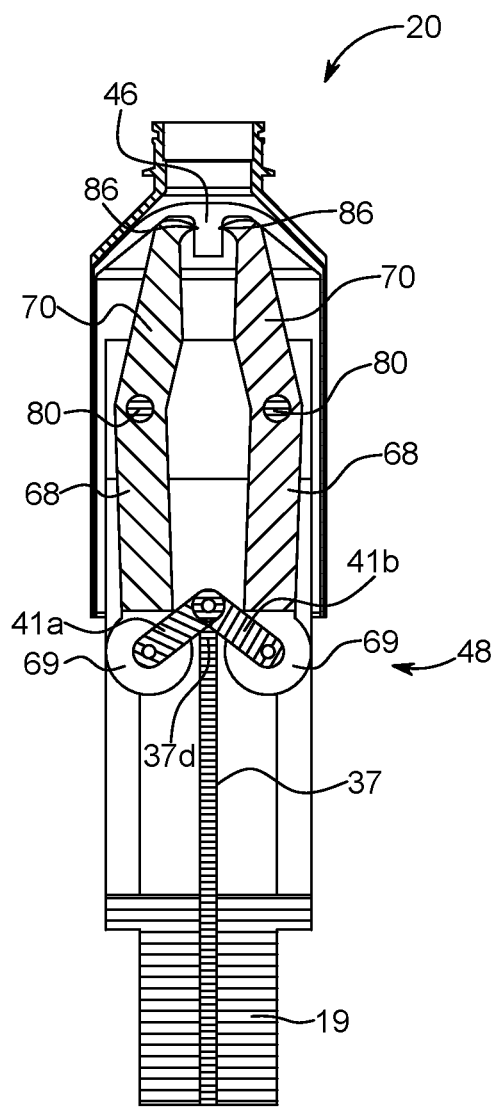
FIG. 10G is a side cross-sectional view of a syringe and a piston having a syringe engagement mechanism in accordance with one example of the present disclosure shown in an open state or configuration.
Figure 10H:
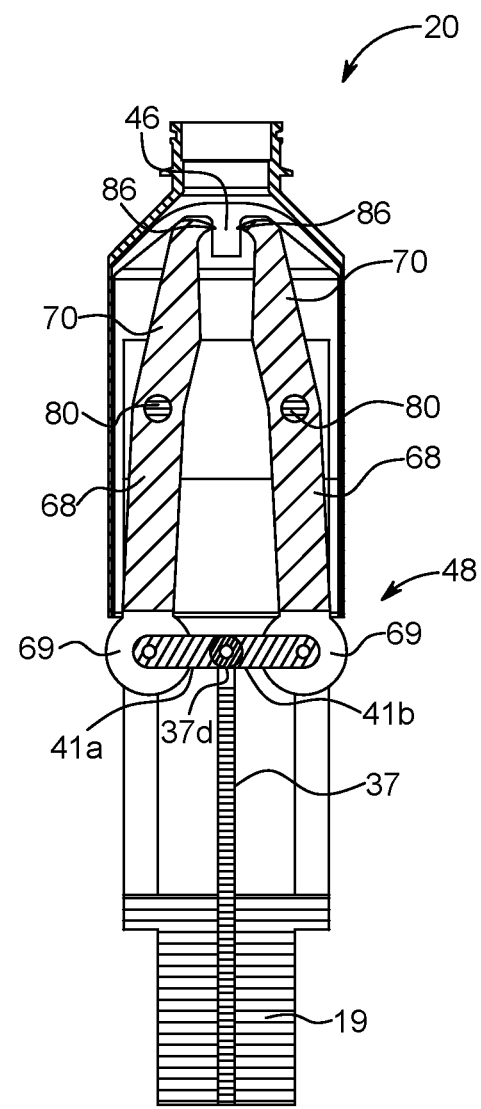
FIG. 10H is a side cross-sectional view of the syringe and the piston with the syringe engagement mechanism shown in FIG. 10G with the syringe engagement mechanism shown in a closed state or configuration.
Figure 11C:
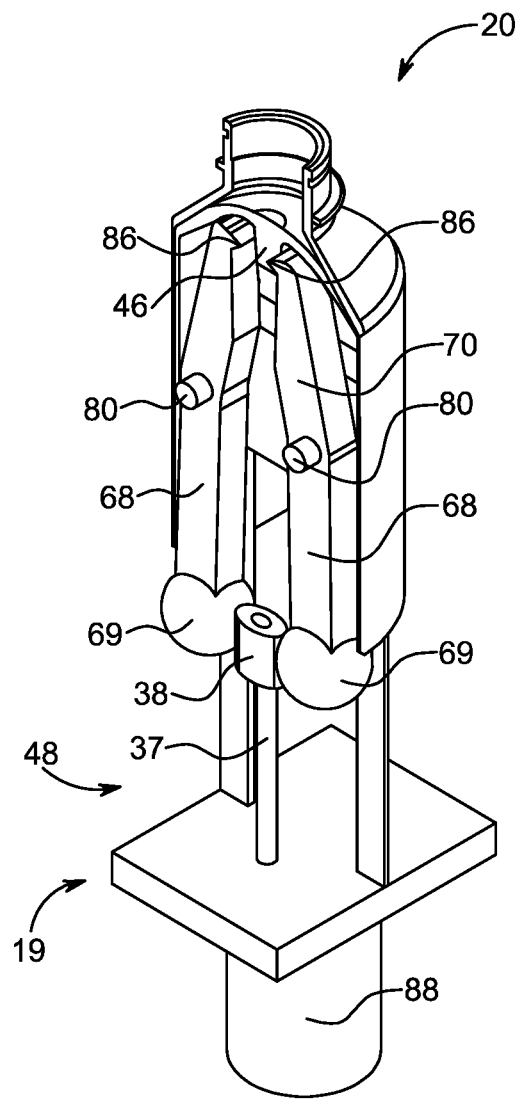
FIG. 11C is a perspective, partial cross-sectional view of the syringe and piston with the syringe engagement mechanism shown in FIG. 11A with the syringe engagement mechanism shown in a closed state or configuration.
Figure 11D:
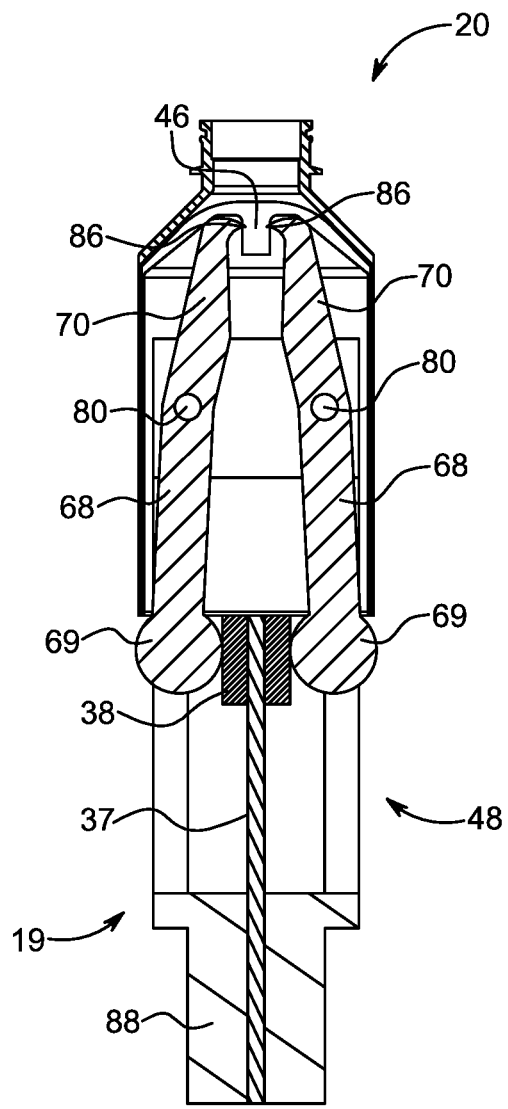
FIG. 11D is a side cross-sectional view of the syringe and the piston with the syringe engagement mechanism shown in FIG. 11C.

In some examples, such as shown in FIGS. 10G-10H, the central rod 37 may have two or more links 41a, 41b pivotally connected at their first end to a distal end 37d of the central rod 37. A second end of each link 41a, 41b is pivotally connected to a proximal end 69 of one of the engagement arms 68. In this manner, movement of the central rod 37 in a proximal/distal direction causes the links 41a, 41b to pivot about their pivot points on the distal end 37d of the central rod 37 and the proximal ends 69 of the engagement arms 68. In certain embodiments, the length of each of the two links 41a, 41b may be selected such that when the links 41a, 41b are oriented substantially perpendicular to a longitudinal axis of the central rod 37, the distal ends 70 of the engagement arms 68 are engaged with the engagement portion 46 of the syringe 20 (FIG. 10H). With movement of the central rod 37 in a proximal direction or distal direction from the position shown in FIG. 10H, the links 41a, 41b are pivoted to a second position, wherein distal ends 70 of the engagement arms 68 are disengaged from the engagement portion 46 of the syringe 20. In other embodiments, the length of each of the two links 41a, 41b may be selected such that the links 41a, 41b remain angled relative to a longitudinal axis of the central rod 37 when the distal ends 70 of the engagement arms 68 are engaged with the engagement portion 46 of the syringe 20 (not shown). According to these embodiments, further proximal retraction of the piston may also cause retraction of the central rod 37 relative to the links 41a, 41b, causing links 41a, 41b to apply a further radially extending force to the proximal ends 69 of the engagement arms 68 and creating a greater engagement or "biting" force between the distal ends 70 of the engagement arms 68 with the engagement portion 46 of the syringe 20.

According to other examples, as shown in FIGS. 11A-11D, the central rod 37 may have an elliptical, oval, or rectangular cam 38 positioned between the proximal ends 69 of the engagement arms 68. The cam 38 has a minor axis and a major axis, wherein the minor axis is shorter than the major axis. The central rod 37 may be rotatable about its longitudinal axis between a disengaged, first position shown in FIGS. 11A-11B and an engaged, second position shown in FIGS. 11C-11D. In the disengaged, first position, the central rod 37 is positioned such that the proximal ends 69 of the engagement arms 68 are substantially aligned parallel with a minor axis of the cam 38. In the engaged, second position, the central rod 37 is rotated about the longitudinal axis such that the proximal ends 69 of the engagement arms 68 are substantially aligned parallel with the major axis of the cam 38, causing the proximal ends 69 to move radially outward with respect to the central rod 37. Spreading of the proximal ends 69 of the engagement arms 68 moves the distal ends 70 thereof closer together and into engagement with the engagement portion 46 of the syringe 20, resulting in digging one or more pointed terminal ends 86 into a surface of the engagement portion 46. Rotation of the central rod 37 between the major and minor axes being in alignment with the proximal ends 69 of the engagement arms 68 selectively moves the mechanism between the first, disengaged position and the second, engaged position. Rotation of the central rod 37 may be effected by a drive mechanism 88, such as by a drive mechanism 88 substantially similar or identical to the drive mechanism 88, such as any of the drive mechanisms described herein.

In other examples similar to that depicted in FIGS. 11A-11D, the cam 38 may be substituted with a disc having slots each corresponding to and interacting with the proximal end 69 of one of the engagement arms 68. In particular, each slot defines a track for the proximal ends 69, such that as the disc is rotated by the drive mechanism 88, the proximal ends 69 of the engagement arms 68 are caused to move radially outward and inward with respect to the central rod 37. Consequently, the engagement arms 68 are forced to rotate about respective pivot pins 80 to engage the engagement portion 46 of the syringe 20.

Figure 12:
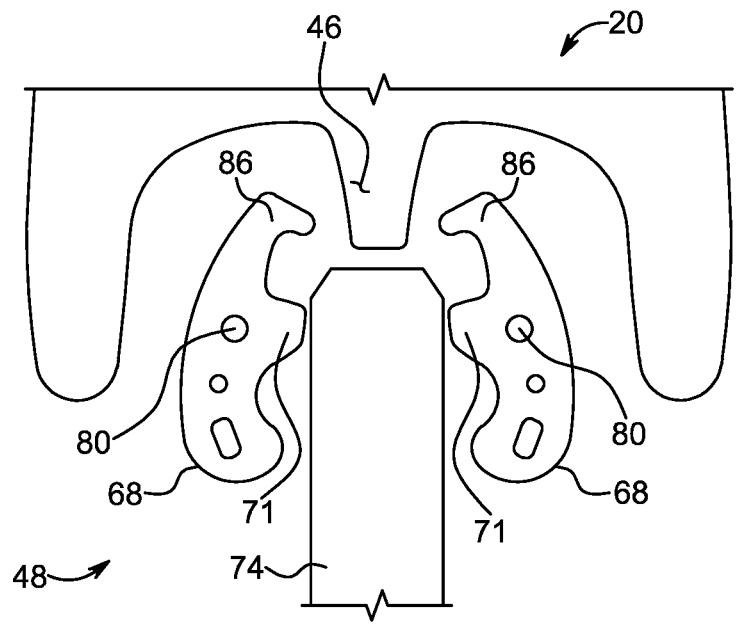
FIG. 12 is a side cross-sectional view of a syringe and a piston having a syringe engagement mechanism in accordance with one example of the present disclosure.

Referring now to FIG. 12, an engagement mechanism 48 in accordance with other aspects of the present disclosure is shown in combination with the proximal end 30 of a syringe 20. The components of the syringe 20 shown in FIG. 12 are substantially similar or identical to the components of the syringe 20 described herein with reference to FIGS. 2A-2B. The engagement mechanism 48 includes one or more engagement arms 68 rotatable around respective pivot pins 80, substantially similar to the engagement arms 68 and pivot pins 80 described herein with reference to FIGS. 1A-11D. The engagement arms 68 differ from those of FIGS. 10A-11D in that the each engagement arm 68 further includes a lobe 71 between the proximal and distal ends of the engagement arm 68. The lobe 71 of each engagement arm 68 is configured to interact with a deactivating pin 74 moveable in the proximal/distal direction. In an unlocked state shown in FIG. 12, the deactivating pin 74 is extended in the distal direction such that the lobe 71 of each engagement arm 68 abuts the deactivating pin 74, thereby preventing the distal ends 70 of the respective engagement arms 68 from engaging the engagement portion 46 of the syringe 20.

The deactivating pin 74 may be retracted in the proximal direction to achieve a locked position in which the lobes 71 are disengaged from the deactivating pin 74 and the pointed terminal ends 86 of the engagement arms 68 are permitted to engage the engagement portion 46 of the syringe 20 by rotation around pivot pins 80.

Proximal/distal movement of the deactivating pin 74 may be controlled by a drive mechanism, substantially similar or identical to the drive mechanism 88 described herein with reference to FIGS. 7A-7B. In some embodiments, the engagement arms 68 may be biased toward the locked position (i.e., normally closed) such that additional mechanisms are not required to maintain engagement between the engagement arms 68 and the engagement portion 46 of the syringe 20. In other embodiments, the engagement arms 68 may be biased toward the unlocked position (i.e., normally open) such that actuation of the deactivating pin 74 or another actuation mechanism is required to engage the engagement arms 68 with the engagement portion 46 of the syringe 20.

Figure 13:
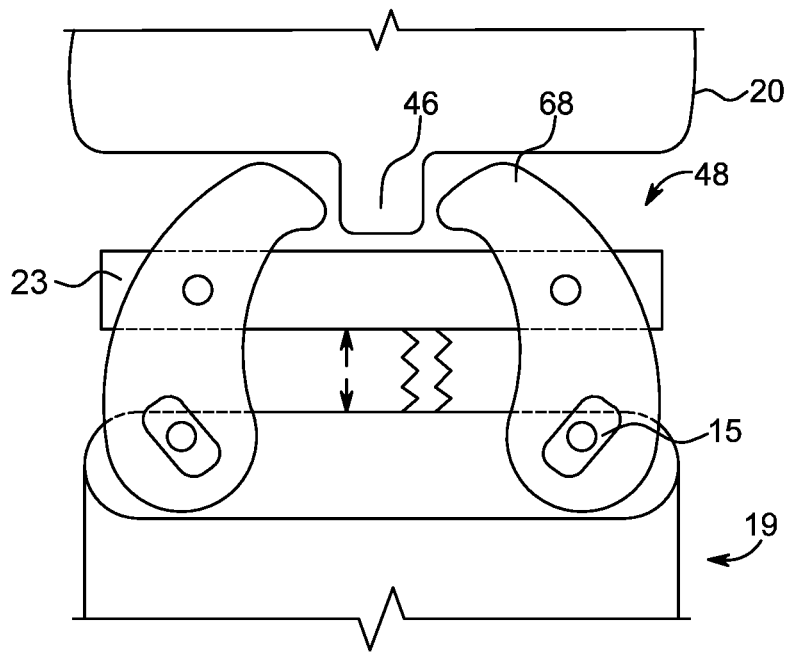
FIG. 13 is a side cross-sectional view of a syringe and a piston having a syringe engagement mechanism in accordance with one example of the present disclosure.

With reference to FIG. 13, an engagement mechanism 48 of a piston 19 is shown in accordance with other examples of the present disclosure. The engagement mechanism 48 includes at least a pair of engagement arms 68 that are pivotally connected to the piston 19 via a cam member 15. In one example, the engagement arms 68 are configured to move between an open first position and a closed second position to grip the engagement portion 46 of the syringe 20. A band 23, may be configured as an electro-active polymer is positioned on each of the engagement arms 68. In some examples, the band 23 may be a nitinol wire or other shape-memory alloy. To move the engagement arms 68 from the open position to the closed position, an electrical charge may be applied or directed to the band 23 to cause the band 23 to contract, thereby reducing the diameter of the band 23. As the band 23 is contracted, the engagement arms 68 are brought towards one another to clamp on the engagement portion 46 of the syringe 20.

Figure 14A:
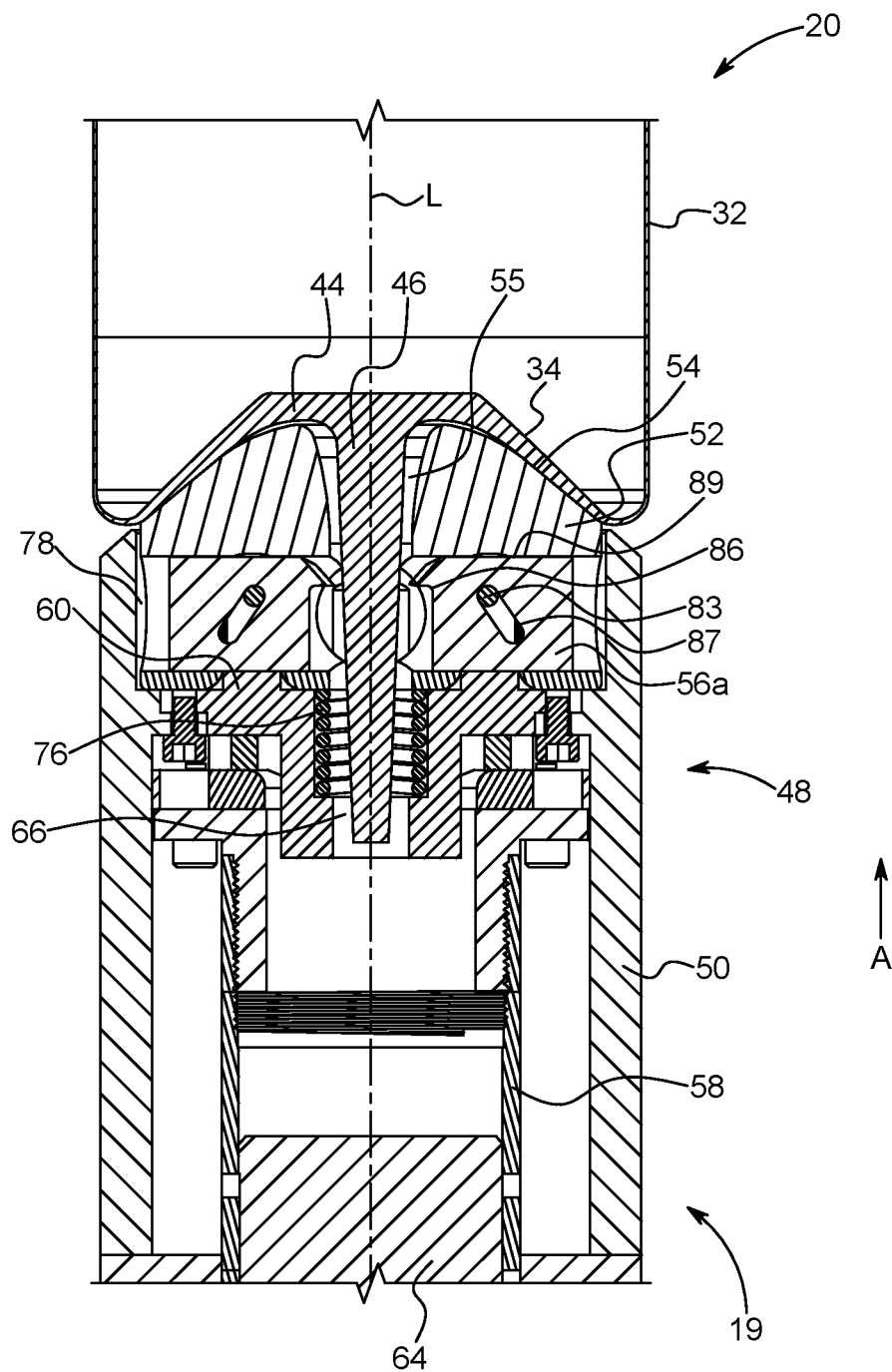
FIG. 14A is a side cross-sectional view of a syringe and a piston having a syringe engagement mechanism in accordance with one example of the present disclosure shown in an open state or configuration.
Figure 14B:
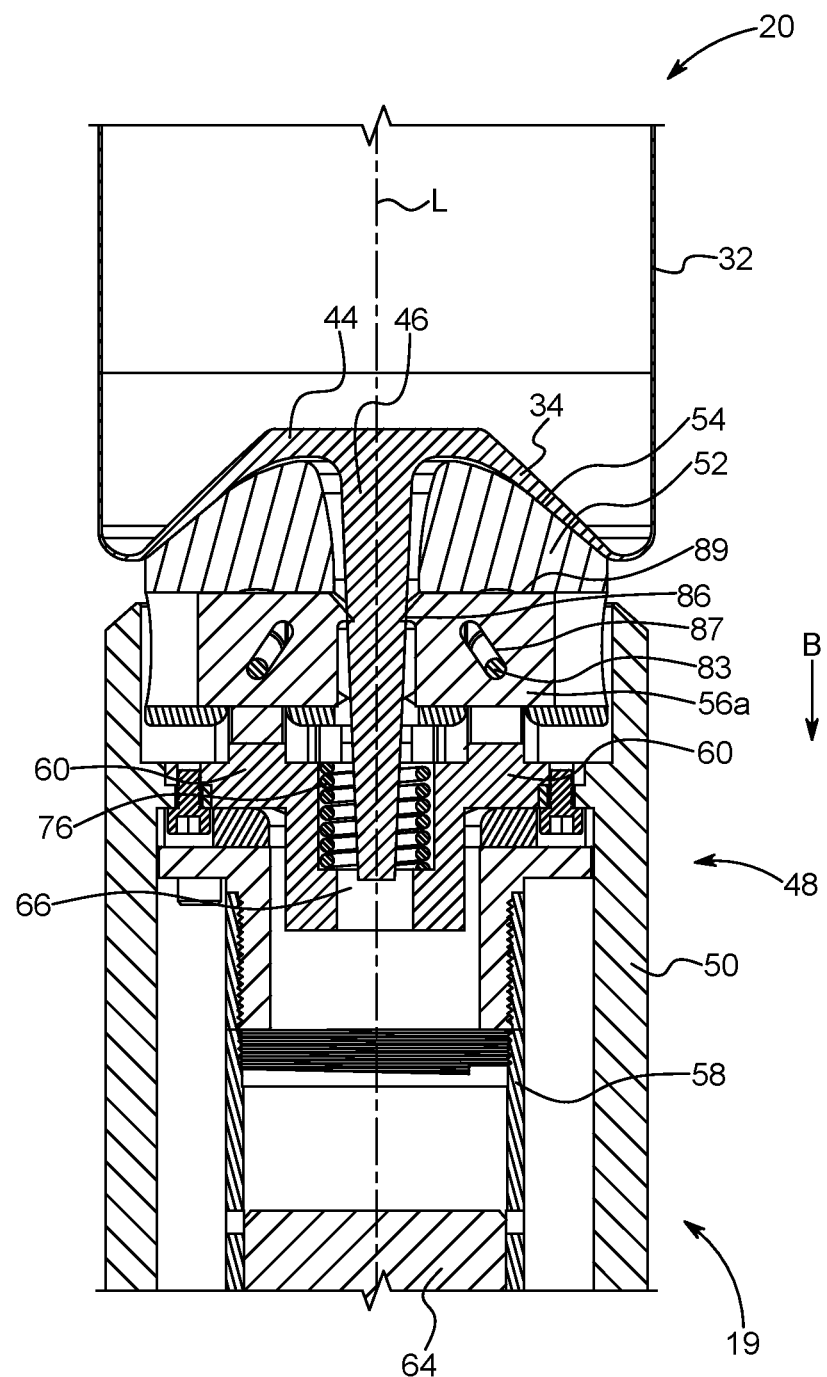
FIG. 14B is a side cross-sectional view of the syringe and the piston with the syringe engagement mechanism of FIG. 14A shown in a closed state or configuration.
Figure 15A:
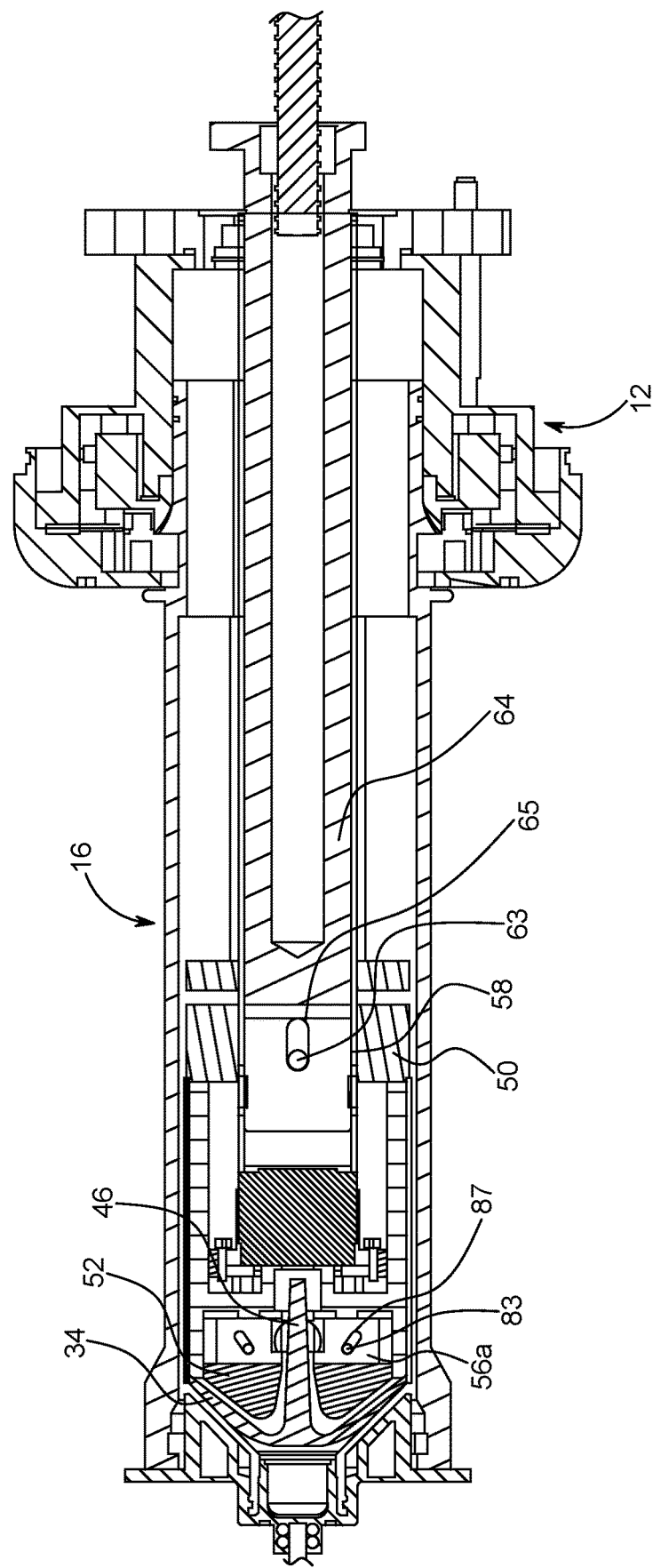
FIG. 15A is a side cross-sectional view of a syringe and a piston having a syringe engagement mechanism in accordance with one example of the present disclosure.
Figure 15B:
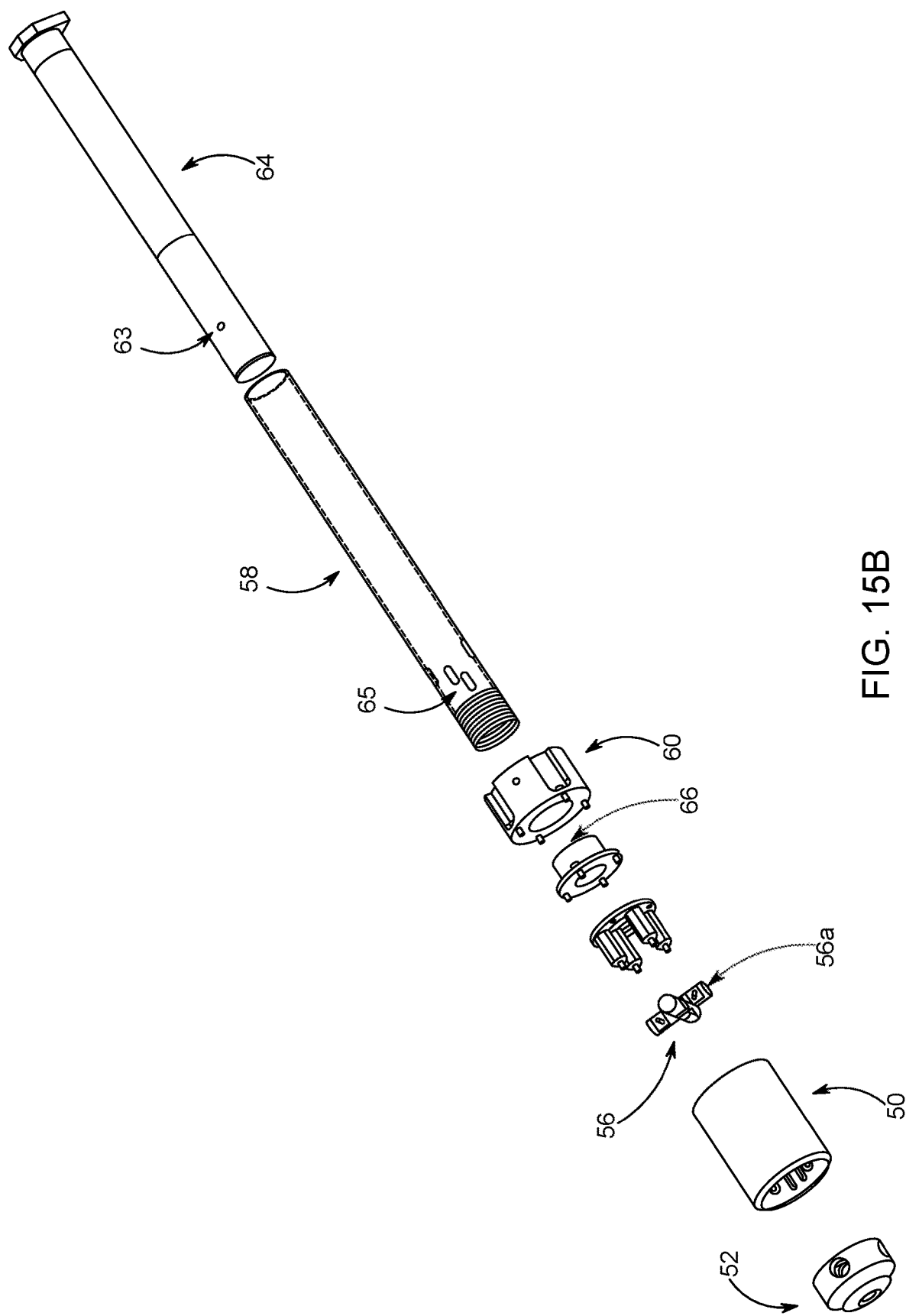
FIG. 15B is an exploded view of the piston and the syringe with the engagement mechanism shown in FIG. 15A.

With reference to FIGS. 14A-15B, an engagement mechanism 48 of a piston 19 is shown in accordance with another example of the present disclosure. FIGS. 14A-14B show the engagement mechanism 48 of the piston 19 in combination with a proximal end 30 of a syringe 20 having an engagement portion 46 configured for engagement with the engagement mechanism 48. FIG. 15B shows an exploded view of the components of the engagement mechanism 48. The components of the syringe 20 shown in FIGS. 14A-15B are substantially similar to the components of the syringe 20 described herein with reference to FIGS. 2A-2B. The engagement portion 46 of the syringe 20 is configured for interacting with one or more engagement pins or surfaces of the engagement mechanism 48 that move radially inward and outward to engage and disengage, respectively, the engagement portion 46 of the syringe 20. In various examples, the inward/outward movement of the engagement pins or surfaces may be effected by a proximal/distal movement of the piston 19. In various examples, movement of the piston 19 in the proximal direction may cause the engagement elements or surfaces to contact the engagement portion 46 of the syringe 20. Conversely, movement of the piston 19 in a distal direction may cause the engagement elements or surfaces to be released from contacting the engagement portion 46 of the syringe 20 such that the syringe 20 may be removed from the pressure jacket 16 and the injector 10.

With continued reference to FIGS. 14A-14B, the piston 19 includes an outer piston sleeve 50 and an abutment section 52 associated therewith substantially identical to the outer piston sleeve 50 and the abutment section 52 discussed herein with reference to FIGS. 3A-3B. The abutment section 52 has an outer engagement surface 54 for engaging at least a portion of the syringe 20. An inner piston sleeve 58 and the abutment section 52 are movable or slidable in an axial direction relative to the outer piston sleeve 50 and a collar 60 with movement of the piston rod 64. For example, the inner piston sleeve 58 and the abutment section 52 may be movable between a first position (FIG. 14A), where radially-extendable engagement elements 56a are disengaged from the engagement portion 46 of the syringe 20 and a second position (FIG. 14B), wherein the engagement elements 56a are engaged with the engagement portion 46. In some examples, the inner piston sleeve 58 and the abutment section 52 may be biased to the second position by a biasing mechanism, such as a spring 76.

The motion of the abutment section 52 and the collar 60 relative to the outer piston sleeve 50 is limited to allow engagement or disengagement of the engagement elements 56 with the engagement portion 46 of the syringe 20. For example, with reference to FIG. 15A, such relative motion can be limited using a dowel 63 fixed to the piston rod 64, where the dowel 63 passes through and seats within a slot 65 formed in the inner piston sleeve 58 that is directly connected to the collar 60 and the abutment section 52. In some examples, the abutment section 52 may be movable by about 0.100 to 0.150 inches, for example 0.125 inches, with the movement of the inner piston sleeve 58 before the outer piston sleeve 50 is moved together with the abutment section 52. In some examples, the inner piston sleeve 58 may be in frictional contact with an inner sidewall of the injector head (not shown). This frictional contact may be used to restrain the inner piston sleeve 58 while allowing the piston rod 64 to move, thereby moving the dowel 63 within the slot 65. Once the dowel 63 engages the proximal or distal end of the slot 65, the frictional force holding the inner piston sleeve 58 is overcome, and the piston rod 64 and the inner piston sleeve 58 may be moved together.

Using this range of movement of the abutment section 52, the collar 60, and the inner piston sleeve 58 relative to the piston rod 64 and the outer piston sleeve 50 (delimited by the longitudinal length of the slot 65), the engagement elements 56a can be moved between the first (open) position (FIG. 14A) and a second (closed) position (FIG. 14B). For example, initial movement of the piston rod 64 in the distal direction may cause the outer piston sleeve 50 to move distally relative to the abutment section 52, which is restrained due to the frictional engagement of the inner piston sleeve 58 with the injector head. Such relative movement of the abutment section 52 and the outer piston sleeve 50 may cause the engagement elements 56a to be retracted in a radially outward direction to allow the syringe 20 to be removed from the injector 10. Conversely, movement of the piston rod 64 in the proximal direction may cause the outer piston sleeve 50 to move proximally relative to the abutment section 52, which is restrained due to the frictional engagement of the inner piston sleeve 58 with the injector head 12. Such relative movement of the abutment section 52 and the outer piston sleeve 50 may cause the engagement elements 56a to be extended in a radially inward direction to engage the engagement portion 46.

With continued reference to FIGS. 14A-14B, the engagement elements 56a may be at least one and optionally a plurality of engagement elements 56a spaced apart circumferentially around a cavity 78 of the outer piston sleeve 50. In some examples, a single engagement element 56a may be configured to contact the engagement portion 46 of the syringe 20. The engagement elements 56a may be spaced apart at equal or unequal angular intervals from one another. In some examples, the engagement elements 56a may have a pointed terminal end 86 for embedding at least a portion of the engagement elements 56a into the material of the engagement portion 46 of the syringe 20 when the engagement elements 56a are positioned in the second position (FIG. 14B).

In some examples, the engagement elements 56a may have a pocket 87 configured to receive a pin 88a extending from the collar 60. The pocket 87 may be angled relative to a longitudinal axis L of the syringe 20. Movement of the engagement elements 56a is constrained by the shape of the pocket 87. The pocket 87 may be shaped such that it directs the movement of the engagement elements 56a from the first to the second position in a linear motion. Due to the angled orientation of the pocket 87, each engagement element 56a may move in two axes of travel—vertically and horizontally relative to the collar 60, as oriented in FIGS. 14A-14B. The engagement elements 56a may also be biased by a biasing mechanism (not shown) to the second, closed position.

To move the engagement elements 56a from the second, closed position to the first, open position, at least a portion of each engagement element 56a may be engaged by a proximal surface 89 the abutment section 52. Because the engagement elements 56a are retained by the pins 88 on the collar 60, movement of the abutment section 52 relative to the collar causes the proximal surface 89 of the abutment section 52 to contact a distal surface of the engagement elements 56a. Continued movement of the abutment section 52 relative to the collar 60 causes the engagement elements 56a to be deflected in a radially outward direction. In this manner, the engagement elements 56a can be disengaged from contacting the engagement portion 46 of the syringe 20.

During movement of the piston 19 in the distal direction, such as shown by arrow A in FIG. 14A, the abutment section 52 contacts the proximal surface of the end wall 34 of the syringe 20. A proximal surface 89 of the abutment section 52 contacts the distal surface of the engagement elements 56a, thereby forcing the engagement elements 56a to move within the pocket 87 in the proximal direction. Proximal movement of the engagement elements 56a within the pocket 87 also moves the engagement elements 56a in a radially outward direction, thereby opening a clearance space between the engagement elements 56a to allow insertion of the engagement portion 46 of the syringe 20 in the space between the engagement elements 56a.

During movement of the piston 19 in the proximal direction, such as shown in arrow B in FIG. 14B, the abutment section 52 moves relative to the outer piston sleeve 50, thereby urging the engagement elements 56a to move within the pocket 87 in a distal and radially inward direction. The radially-inward movement of the engagement elements 56a toward the engagement portion 46 of the syringe 20 causes the pointed terminal end 86 to dig into the material of the engagement portion 46 and become at least partially embedded therein. With continued proximal movement of the piston 19, the end wall 34 of the syringe 20 is also moved in the proximal direction due to connection between the engagement elements 56a and the engagement portion 46 of the syringe 20. In some examples, the engagement elements 56a may be configured to move from the first position to the second position immediately upon proximal movement of the piston 19. In other examples, the engagement elements 56a may be configured to gradually and progressively move from the first position toward the second position with proximal movement of the piston 19 to continuously increase the gripping force on the engagement portion 46 of the syringe 20.

Figure 16A:
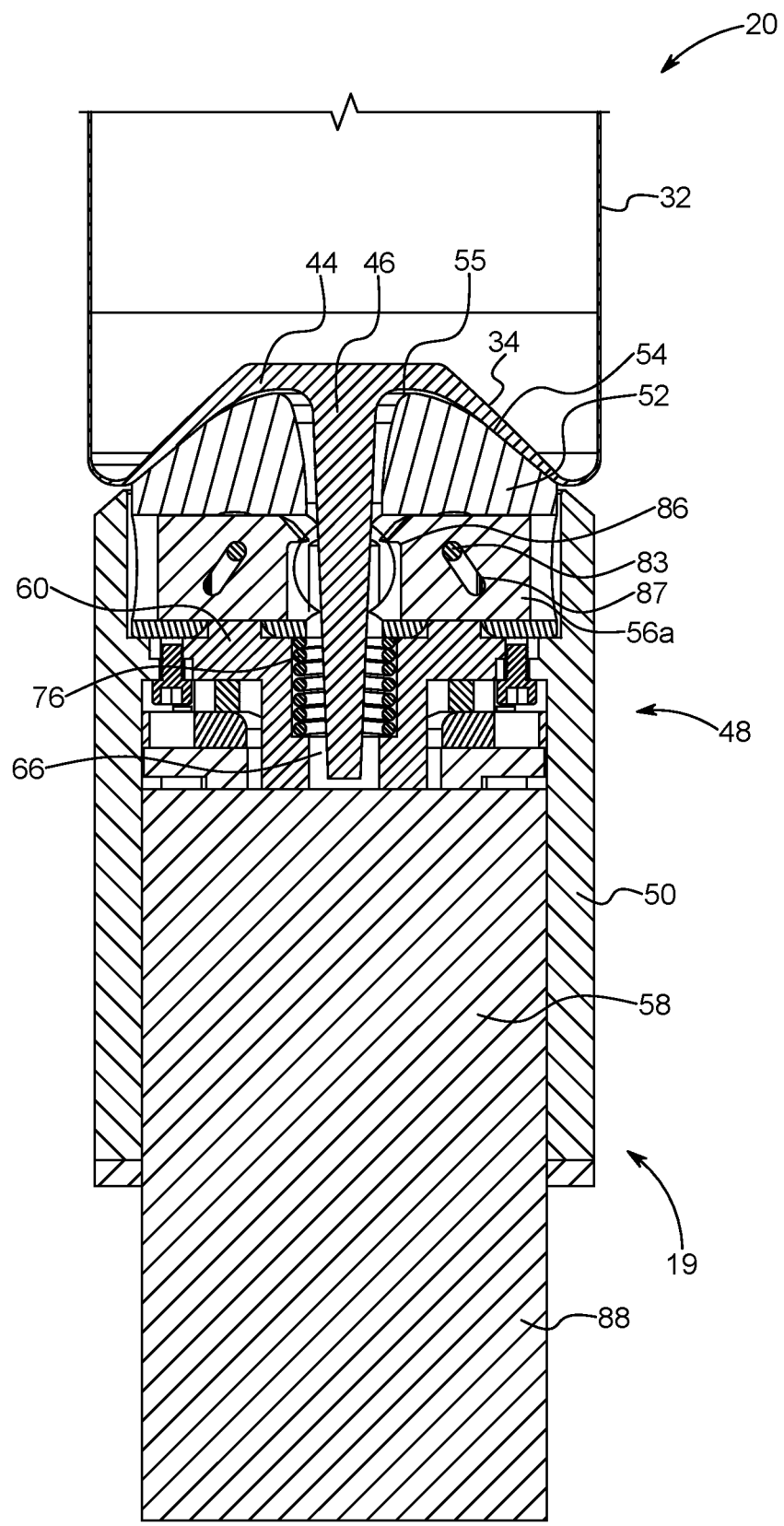
FIG. 16A is a side cross-sectional view of a syringe and a piston having a syringe engagement mechanism in accordance with one example of the present disclosure shown in an open state or configuration.
Figure 16B:
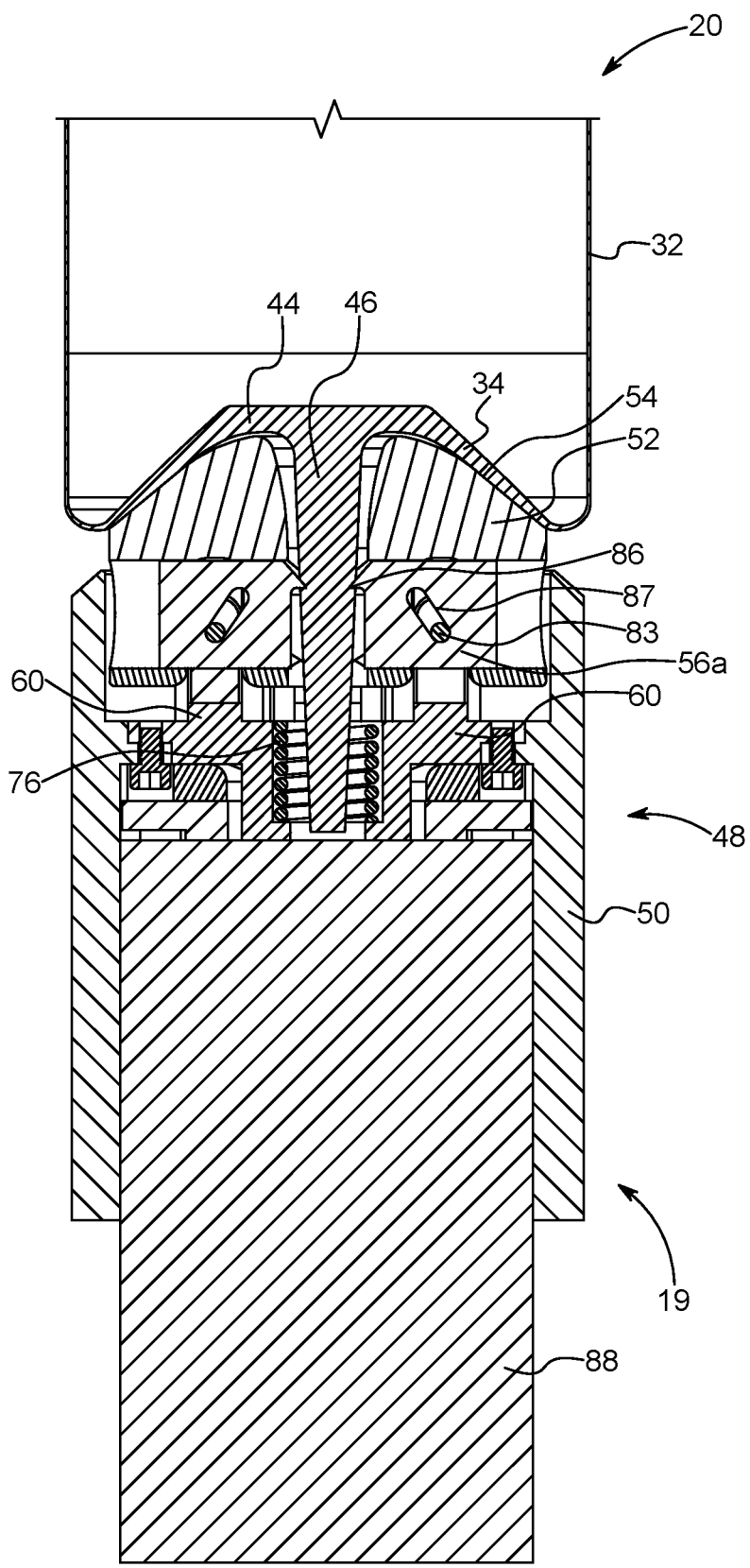
FIG. 16B is a side cross-sectional view of the syringe and the piston with the syringe engagement mechanism of FIG. 16A shown in a closed state or configuration.

FIGS. 16A-16B show the proximal end of the syringe 20 in combination with an engagement mechanism 48 of the piston 19 in accordance with another example of the present disclosure. The components of the syringe 20 shown in FIGS. 16A-16B are substantially similar to the components of the syringe 20 described herein with reference to FIGS. 2A-2B. Similarly, components of the engagement mechanism 48 shown in FIGS. 16A-16B are substantially similar to the components of the piston 19 described herein with reference to FIGS. 14A-15B, with the exception of the drive mechanism 88, as described herein. In various examples, the inward/outward movement of the engagement elements 56 or surfaces may be effected independently of a proximal/distal movement of the piston 19.

The piston 19 has the drive mechanism 88 for controlling the movement of the engagement elements 56a between a first, or disengaged position (FIG. 16A) and a second, engaged position (FIG. 16B). The drive mechanism 88 may be electrically, pneumatically, and/or hydraulically operated. For example, the drive mechanism 88 may have an electric or electromechanical mechanism, such as a linear or rotary electric motor, or a solenoid. In some examples, the drive mechanism 88 may be selectively energized, such as during proximal or distal movement of the piston 19. In other examples, the drive mechanism 88 may be constantly energized, regardless of whether the piston 19 is stationary, or moving in the proximal or distal direction.

Movement of the drive mechanism 88 relative to the outer piston sleeve 50 is configured to allow engagement or disengagement of the engagement elements 56a with the engagement portion 46 of the syringe 20. In some examples, movement of the outer piston sleeve 50 in a distal direction toward the syringe 20 may result in the drive mechanism 88 retracting the engagement elements 56 in a radially outward direction to allow the syringe 20 to be removed from the injector 10. Conversely, movement of the outer piston sleeve 50 in the proximal direction may result in the drive mechanism 88 extending the engagement elements 56a in a radially inward direction to engage the engagement portion 46 of the syringe 20. In other examples, operation of the drive mechanism 88 may be independent of the movement of the outer piston sleeve 50 such that the engagement elements 56a can be extended or retracted based upon operation of the drive mechanism 88 only.

Figure 17A:
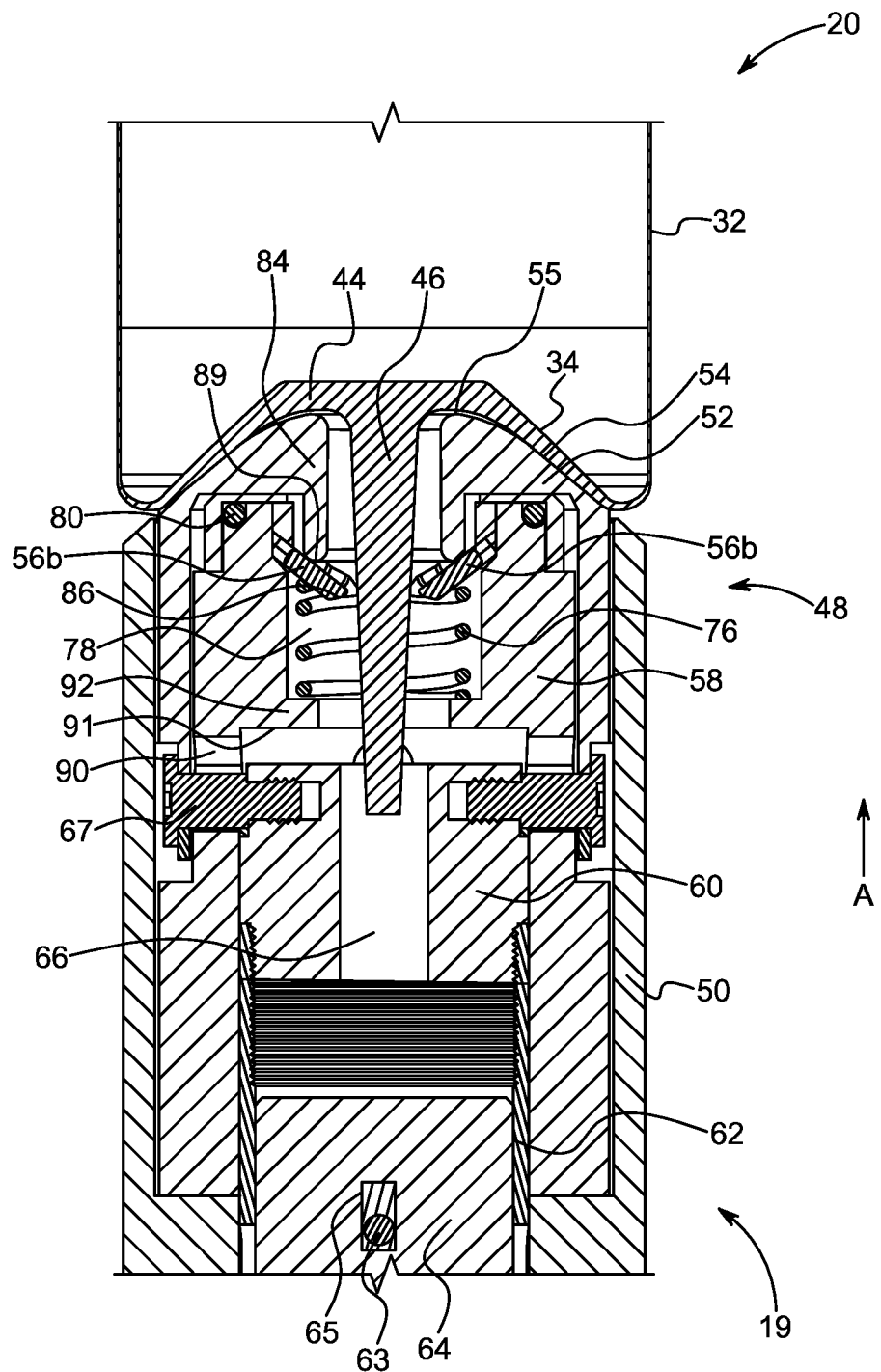
FIG. 17A is a side cross-sectional view of a syringe and a piston having a syringe engagement mechanism in accordance with one example of the present disclosure shown in an open state or configuration.
Figure 17B:
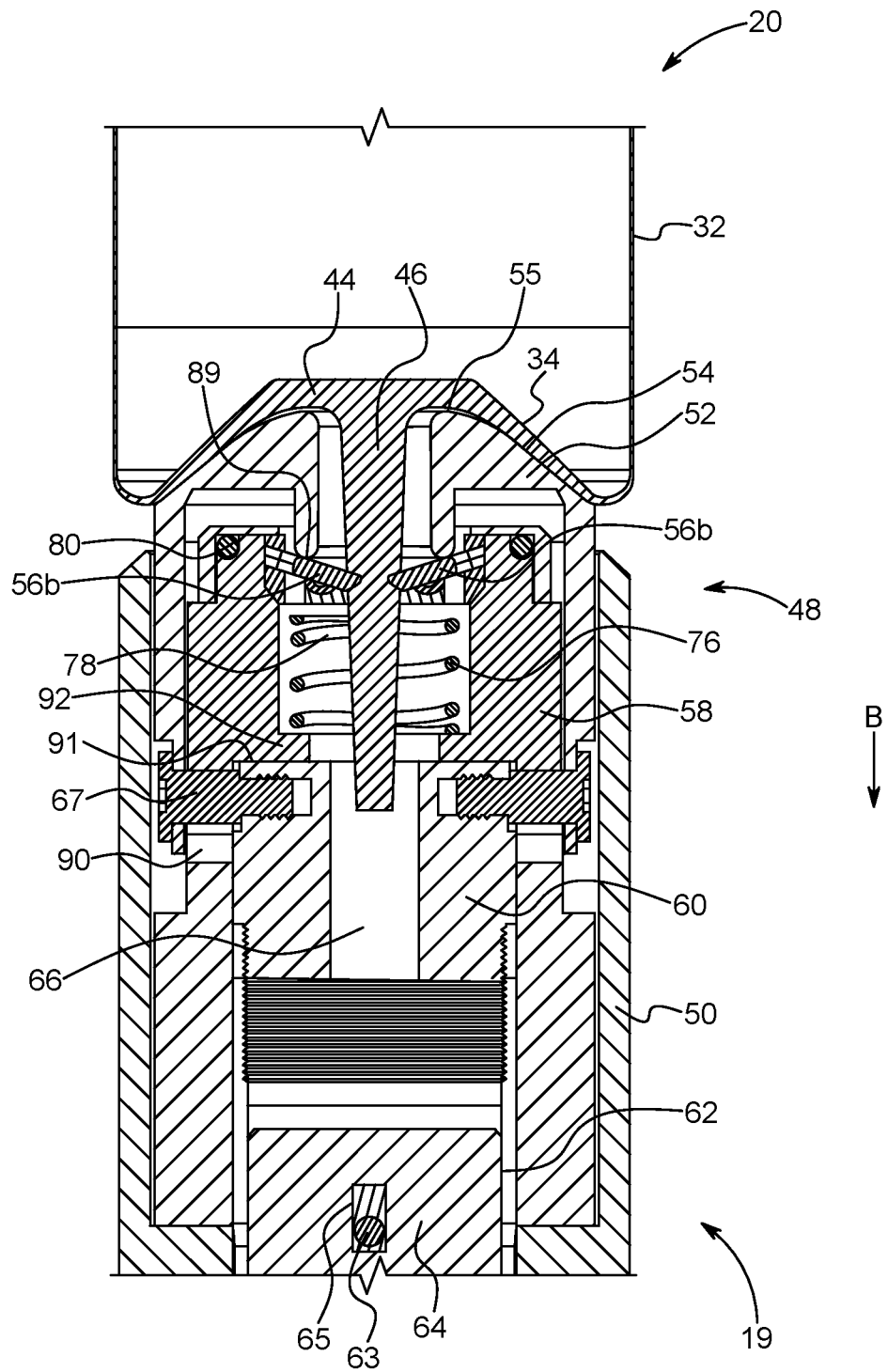
FIG. 17B is a side cross-sectional view of the syringe and the piston with the syringe engagement mechanism of FIG. 17A shown in a closed state or configuration.

FIGS. 17A-17B show the proximal end 30 of the syringe 20 in combination with an engagement mechanism 48 of the piston 19 in accordance with one example of the present disclosure. The components of the syringe 20 shown in FIGS. 17A-17B are substantially similar to the components of the syringe 20 described herein with reference to FIGS. 2A-2B. The engagement portion 46 of the syringe 20 is configured for interacting with one or more engagement pins or surfaces of the engagement mechanism 48 that move radially inward and outward to engage and disengage, respectively, the engagement portion 46 of the syringe 20. In various examples, the inward/outward movement of the engagement pins or surfaces may be effected by a proximal/distal movement of the piston 19. For example, movement of the piston 19 in the proximal direction may cause the engagement pins or surfaces to contact the engagement portion 46 of the syringe 20. Conversely, movement of the piston 19 in a distal direction may cause the engagement pins or surfaces to be released from contacting the engagement portion 46 of the syringe 20 such that the syringe 20 may be removed from the pressure jacket 16 and the injector 10.

With continued reference to FIGS. 17A-17B, the piston 19 includes an outer piston sleeve 50 and an abutment section 52 attached thereto substantially identical to the outer piston sleeve 50 and the abutment section 52 discussed herein with reference to FIGS. 3A-3B. The abutment section 52 has an outer engagement surface 54 for engaging at least a portion of the syringe 20. An inner piston sleeve 58 and the abutment section 52 are movable or slidable in an axial direction relative to the outer piston sleeve 50 and a collar 60 with movement of the piston rod 64. For example, the inner piston sleeve 58 and the abutment section 52 may be movable between a first position (FIG. 17A), where radially-extendable pins 56b are disengaged from the engagement portion 46 of the syringe 20 and a second position (FIG. 17B), wherein the pins 56b are engaged with the engagement portion 46. In some examples, the inner piston sleeve 58 and the abutment section 52 may be biased to the second position by a biasing mechanism, such as a spring 76.

The piston 19 also has an inner piston sleeve 58 that is fixed relative to the outer piston sleeve 50. The inner piston sleeve 58 extends into at least a portion of the abutment section 52 such that the abutment section 52 is positioned between the outer piston sleeve 50 and the inner piston sleeve 58. A collar 60 is movably mounted within the inner piston sleeve 58. In some examples, the collar 60 may be mounted to a piston rod sleeve 62 movable by a piston rod 64, such as by a threaded connection. The collar 60 has a longitudinal opening 66 configured to receive at least a portion of the engagement portion 46 of the syringe 20. Desirably, an inner diameter of the longitudinal opening 66 is larger than an outer diameter of the widest portion of the engagement portion 46 to allow free insertion of the engagement portion 46 into the longitudinal opening 66.

With continued reference to FIGS. 17A-17B, the abutment section 52 is connected to the collar 60, such as by one or more fasteners 67. In this manner, movement of the collar 60 results in a corresponding movement of the abutment section 52. A pocket 90 in the inner piston sleeve 58 provides clearance for movement of the abutment section 52 and the collar 60. Proximal and distal ends of the pocket 90 delimit the range of movement of the abutment section 52 and the collar 60 relative to the inner piston sleeve 58. Alternatively, or in addition, a proximal surface 91 of a lip 92 extending radially inward into the cavity 78 of the inner piston sleeve 58 may define a stop surface to delimit the movement of the collar 60 in the distal direction.

The collar 60 and the abutment section 52 are movable or slidable in an axial direction relative to the outer piston sleeve 50 and the inner piston sleeve 58 with movement of the piston rod 64 and the piston rod sleeve 62. For example, the collar 60 and the abutment section 52 may be movable between a first position (FIG. 17A), where the pins 56b are disengaged from the engagement portion 46 of the syringe 20 and a second position (FIG. 17B), wherein the pins 56b are engaged with the engagement portion 46. In some examples, the pins 56b may be biased to the second position by a biasing mechanism, such as a spring 76 that deflects the pins 56b to pivot about a pivot pin 80 in a radially inward direction to contact the engagement portion 46 of the syringe 20.

The motion of the abutment section 52 and the collar 60 relative to the outer piston sleeve 50 is limited to allow engagement or disengagement of the pins 56b with the engagement portion 46 of the syringe 20. For example, with reference to FIG. 17A, such relative motion can be limited using a dowel 63 fixed to the piston rod 64, where the dowel 63 passes through and seats within a slot 65 formed in the piston rod sleeve 62 that is directly connected to the collar 60 and the abutment section 52. In some examples, the abutment section 52 may be movable by about 0.100 to 0.150 inches, for example 0.125 inches, with the movement of the piston rod sleeve 62 before the outer piston sleeve 50 is moved together with the abutment section 52. In some examples, the piston rod sleeve 62 may be in frictional contact with an inner sidewall of the injector head (not shown). This frictional contact may be used to restrain the piston rod sleeve 62 while allowing the piston rod 64 to move, thereby moving the dowel 63 within the slot 65. Once the dowel 63 engages the proximal or distal end of the slot 65, the frictional force holding the piston rod sleeve 62 is overcome, and the piston rod 64 and the piston rod sleeve 62 may be moved together.

Using this range of movement of the abutment section 52, the collar 60, and the piston rod sleeve 62 relative to the piston rod 64, the inner piston sleeve 58, and the outer piston sleeve 50 (delimited by the longitudinal length of the slot 65), the pins 56b can be moved between the first (open) position (FIG. 17A) and a second (closed) position (FIG. 17B). For example, initial movement of the piston rod 64 in the distal direction may cause the outer piston sleeve 50 to move distally relative to the abutment section 52, which is restrained due to the frictional engagement of the piston rod sleeve 62 with the injector head. Such relative movement of the abutment section 52 and the outer piston sleeve 50 may cause the pins 56b to be retracted in a radially outward direction to allow the syringe 20 to be removed from the injector 10. Conversely, movement of the piston rod 64 in the proximal direction may cause the outer piston sleeve 50 to move proximally relative to the abutment section 52, which is restrained due to the frictional engagement of the piston rod sleeve 62 with the injector head. Such relative movement of the abutment section 52 and the outer piston sleeve 50 may cause the pins 56b to be extended in a radially inward direction to engage the engagement portion 46 of the syringe 20.

With continued reference to FIGS. 17A-17B, the pins 56b may be at least one and optionally a plurality of pins 56b spaced apart circumferentially around a cavity 78 of the inner piston sleeve 58. In some examples, a single pin 56b may be configured to contact the engagement portion 46 of the syringe 20 and force the engagement portion 46 in contact with a surface of the abutment section 52. The pins 56b may be spaced apart at equal or unequal angular intervals from one another. The pins 56b may be movable between a first position (FIG. 17A), where the pins 56b do not contact the engagement portion 46 of the syringe 20, and a second position (FIG. 17B), wherein the pins 56b contact the outer surface of the engagement portion 46 of the syringe 20. In some examples, the pins 56b may have a pointed terminal end 86 for embedding at least a portion of the pins 56b into the material of the engagement portion 46 of the syringe 20 when the pins 56b are positioned in the second position (FIG. 17B).

In some examples, the pins 56b may be pivotable about a pivot pin 80 provided on the inner piston sleeve 58. As noted previously, the pins 56b may be biased by the biasing mechanism 76, such as a spring, to the second position. To move the pins 56b from the second position to the first position, at least a portion of each pin 56b may be engaged by at least a portion of the abutment section 52, such as a proximal surface 89 of an annular skirt 84 defining the opening 55 of the abutment section 52. Because the pins 56b are retained on the inner piston sleeve 58, movement of the abutment section 52 relative to the inner piston sleeve 58 causes the proximal surface 89 of the annular skirt 84 to contact a distal surface of the pins 56b. Continued movement of the abutment section 52 relative to the inner piston sleeve 58 causes the pins 56b to be deflected in a radially outward direction. In this manner, the pins 56b can be disengaged from contacting the engagement portion 46 of the syringe 20.

During movement of the piston 19 in the distal direction, such as shown by arrow A in FIG. 17A, the abutment section 52 contacts the proximal surface of the end wall 34 of the syringe 20. Because the abutment section 52 is movable relative to the outer and inner sleeves 50, 58, the abutment section 52 is moved axially in the proximal direction relative to the outer and inner sleeves 50, 58. The one or more pins 56b contact proximal surface 89 of the annular skirt 84 of the abutment section 52 as the abutment section 52 is moved relative to the outer and inner sleeves 50, 58. The contact between the pins 56b and the proximal surface 89 of the annular skirt 84 causes the pins 56b to be deflected away from the engagement portion 46 of the syringe 20 in a radially outward direction about the pivot pin 80 thereby opening a clearance space between the pins 56b to allow insertion of the engagement portion 46 of the syringe 20 in the space between the pins 56b.

During movement of the piston 19 in the proximal direction, such as shown by arrow B in FIG. 17B, the abutment section 52 moves relative to the outer piston sleeve 50. During such movement, the pins 56b are deflected toward the engagement portion 46 of the syringe 20 in a radially inward direction about the pivot pin 80 due to a restoring force of the biasing mechanism 76, such as a spring. The pins 56b may be angled relative to a longitudinal axis of the syringe 20 such that continued proximal movement of the piston 19 causes the pins 56b, specifically the pointed terminal end 86, to increase contact with the outer surface of the engagement portion 46 of the syringe 20. In some examples, the pointed terminal end 86 may dig into the outer surface of the engagement portion 46 of the syringe 20.

Figure 18A:
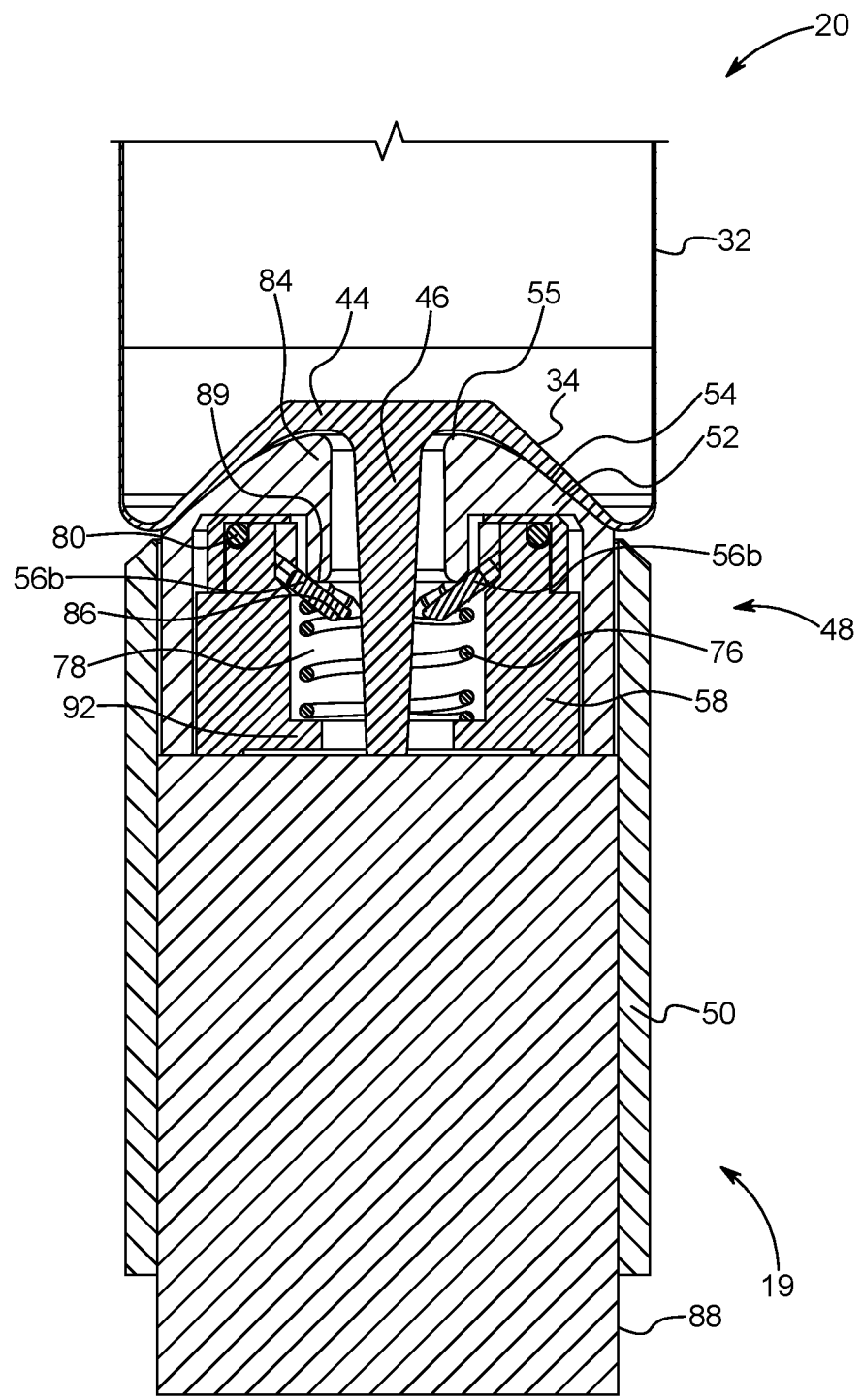
FIG. 18A is a side cross-sectional view of a syringe and a piston having a syringe engagement mechanism in accordance with one example of the present disclosure shown in an open state or configuration.
Figure 18B:
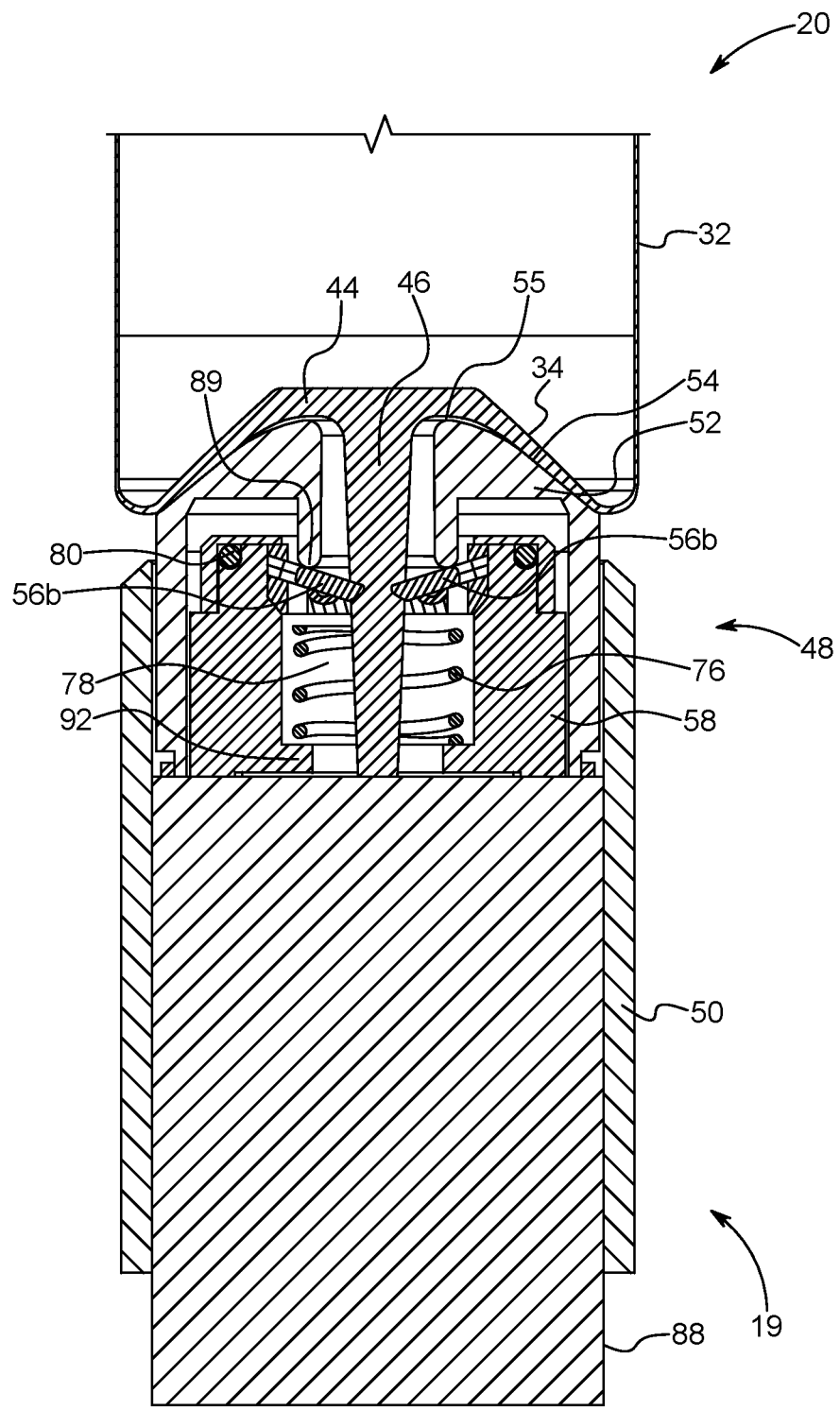
FIG. 18B is a side cross-sectional view of the syringe and the piston with the syringe engagement mechanism of FIG. 18A shown in a closed state or configuration.

FIGS. 18A-18B show the proximal end of the syringe 20 in combination with an engagement mechanism 48 of the piston 19 in accordance with another example of the present disclosure. The components of the syringe 20 shown in FIGS. 18A-18B are substantially similar to the components of the syringe 20 described herein with reference to FIGS. 2A-2B. Similarly, components of the engagement mechanism 48 shown in FIGS. 18A-18B are substantially similar to the components of the piston 19 described herein with reference to FIGS. 4A-4B, with the exception of the drive mechanism 88, as described herein. In various examples, the inward/outward movement of the engagement elements or surfaces may be effected independently of a proximal/distal movement of the piston 19.

The piston 19 has the drive mechanism 88 for controlling the movement of the pins 56b between a first, or disengaged position (FIG. 18A) and a second, engaged position (FIG. 18B). The drive mechanism 88 may be electrically, pneumatically, and/or hydraulically operated. For example, the drive mechanism 88 may have an electric or electromechanical mechanism, such as a linear or rotary electric motor, or a solenoid. In some examples, the drive mechanism 88 may be selectively energized, such as during proximal or distal movement of the piston 19. In other examples, the drive mechanism 88 may be constantly energized, regardless of whether the piston 19 is stationary, or moving in the proximal or distal direction.

Movement of the drive mechanism 88 relative to the outer piston sleeve 50 is configured to allow engagement or disengagement of the pins 56*b* with the engagement portion 46 of the syringe 20. In some examples, movement of the outer piston sleeve 50 in a distal direction toward the syringe 20 may result in the drive mechanism 88 retracting the pins 56*b* in a radially outward direction to allow the syringe 20 to be removed from the injector 10. Conversely, movement of the outer piston sleeve 50 in the proximal direction may result in the drive mechanism 88 extending the pins 56*b* in a radially inward direction to engage the engagement portion 46 of the syringe 20. In other examples, operation of the drive mechanism 88 may be independent of the movement of the outer piston sleeve 50 such that the pins 56*b* can be extended or retracted based upon operation of the drive mechanism 88 only.

FIGS. 19A-19E show the proximal end 30 of the syringe 20 in combination with an engagement mechanism 48 of the piston 19 in accordance with another example of the present disclosure. An engagement portion 46 of the syringe 20 is configured for interacting with one or more surfaces of the engagement mechanism 48 that engage and disengage the engagement portion 46 of the syringe 20 with movement of the piston 19.

Figure 19A:
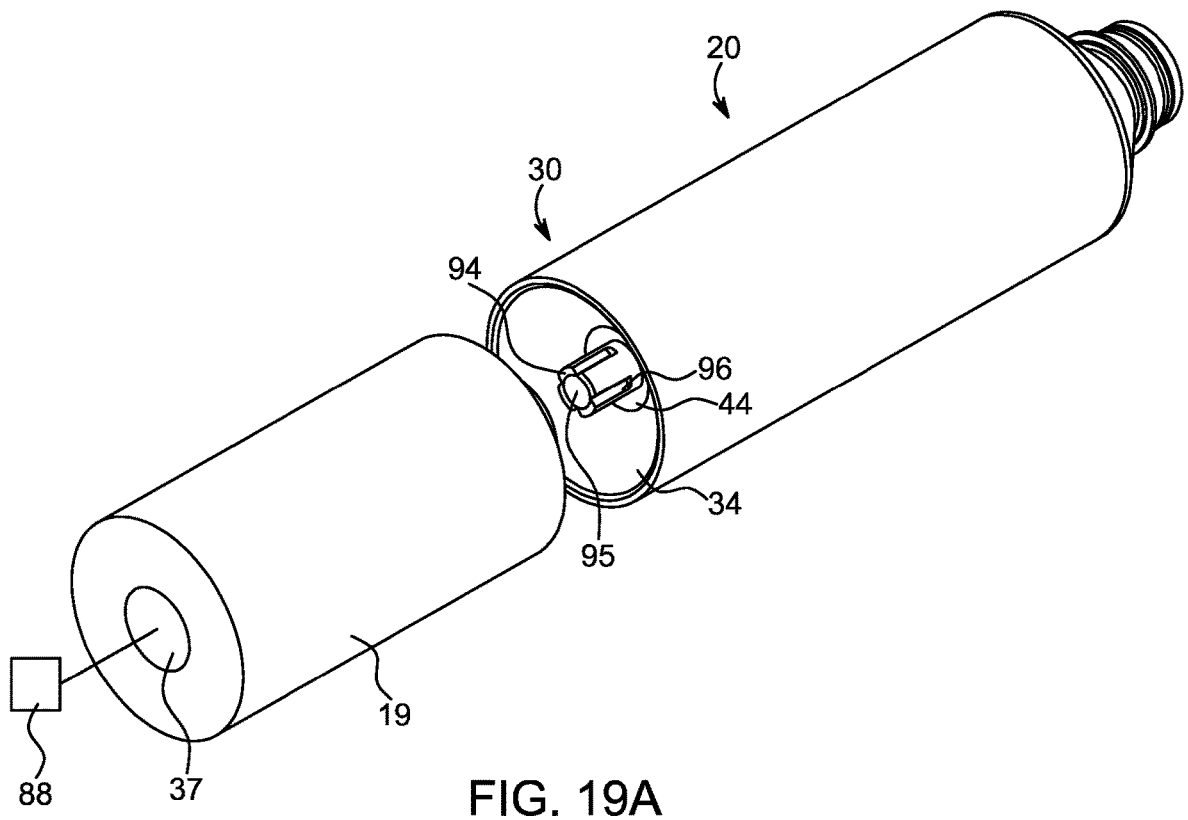
FIG. 19A is an exploded perspective view of a syringe and a piston having a syringe engagement mechanism in accordance with one example of the present disclosure.
Figure 19B:
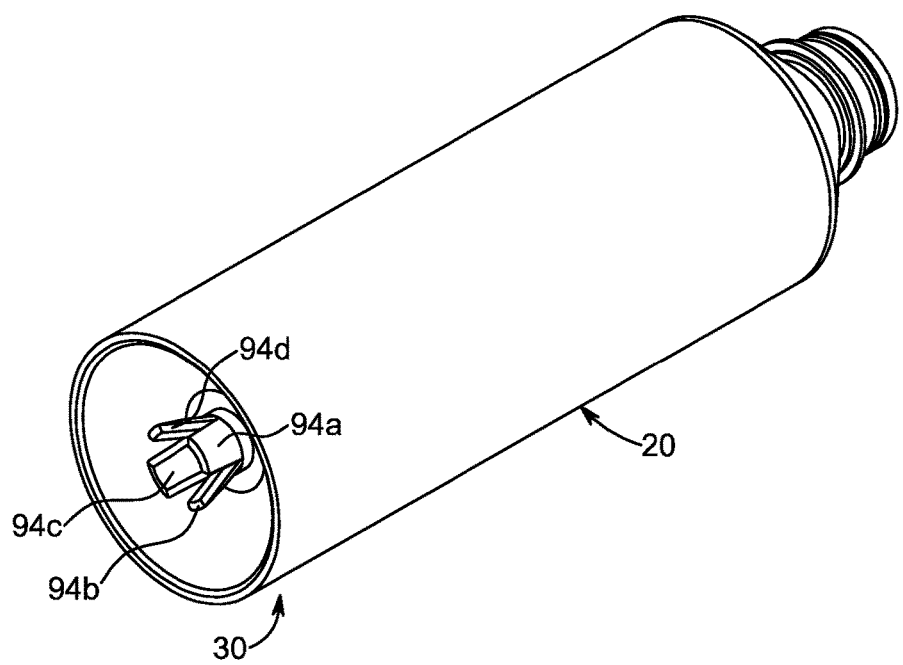
FIG. 19B is a rear perspective view of the syringe shown in FIG. 19A shown after engagement with the syringe engagement mechanism.

With specific reference to FIG. 19A, the end wall 34 of the syringe 20 may have a central portion 44 having a substantially dome-shaped structure and an annular piston engagement portion 46 extending proximally from the central portion 44. In some examples, the engagement portion 46 may extend in a proximal direction along a longitudinal axis of the syringe 20 from an approximate midpoint of the central portion 44. The engagement portion 46 has an annular shape with a sidewall 94 defining a central opening 95 configured to receive a central rod 37 of the piston. The sidewall 94 may be expandable between a first configuration shown in FIG. 19A and a second configuration shown in FIG. 19B. For example, the sidewall 94 may be a frangible sidewall that separates from a single, circumferential sidewall 94 shown in FIG. 19A, to a plurality of sidewall segments 94*a*-94*d* shown in FIG. 19B. In some examples, the sidewall 94 may separate into a plurality of sidewall segments 94*a*-94*d* due to interaction with the central rod 37. The sidewall 94 may have one or more grooves 96 extending in a direction along a longitudinal axis of the syringe 20 over at least a portion of the longitudinal length of the engagement portion 46. The one or more grooves 96 may have a smaller thickness than the sidewall 94. The one or more grooves 96 define weakened areas of the sidewall 94 such that the sidewall 94 may split into the plurality of sidewall segments 94*a*-94*d* along the one or more grooves 96.

The engagement portion 46 may be substantially flush with the proximal end of the syringe 20, or it may extend proximally beyond the proximal end of the syringe 20 or be recessed distally into the dome-shaped proximal end. The engagement portion 46 may be monolithically formed with the syringe body, or it may be removably or non-removably attached to the central portion 44 of the end wall 34, such as by welding, adhesion, or clip attachment, or other fastening mechanism. In some examples, the sidewall 94 of the engagement portion 46 may have a substantially circular cross-section. In other examples, the sidewall 94 may have a star-shaped cross-section, or cross-section having any regular or irregular geometric shape or may include a post with a proximal flange, nub, or gripping element having a greater diameter than the post.

The engagement portion 46 is configured for interacting with the central rod 37 of the piston 19 of the fluid injector 10, as described herein. In various examples, the proximal/distal movement of the central rod 37 may be effected by a proximal/distal movement of the piston 19. In some examples, the proximal/distal movement of the central rod 37 may be independent of the proximal/distal movement of the piston 19, such as by a drive mechanism 88 (shown in FIGS. 19C-19E). The drive mechanism 88 may be electrically, pneumatically, and/or hydraulically operated. For example, the drive mechanism 88 may have an electric or electromechanical mechanism, such as a linear or rotary electric motor, or a solenoid. In some examples, the drive mechanism 88 may be selectively energized, such as during proximal or distal movement of the central rod 37. In other examples, the drive mechanism 88 may be constantly energized, regardless of whether the central rod 37 is stationary, or moving in the proximal or distal direction. The drive mechanism 88 may have a locking mechanism (not shown) for locking the central rod 37 in a desired position.

Figure 19C:
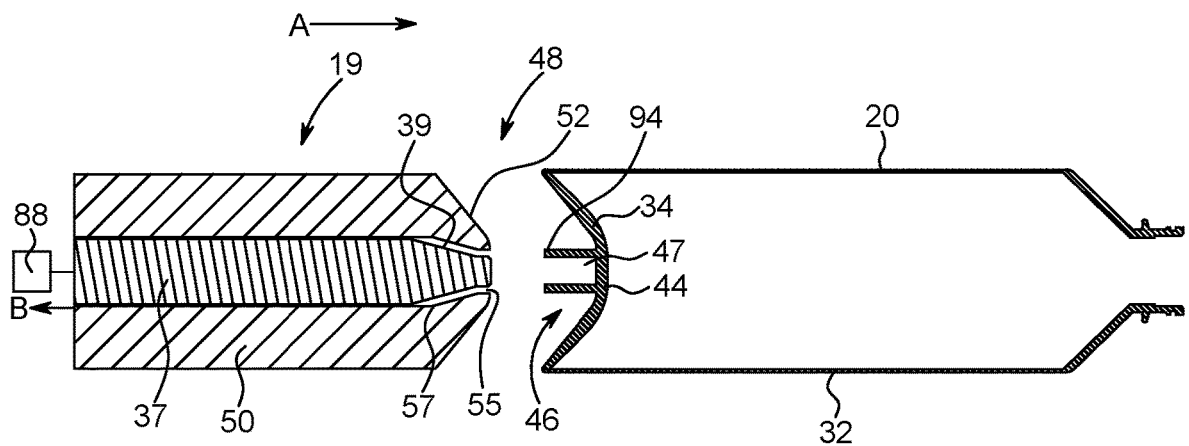
FIG. 19C is a side cross-sectional view of the syringe and the syringe engagement mechanism in a first position.
Figure 19D:
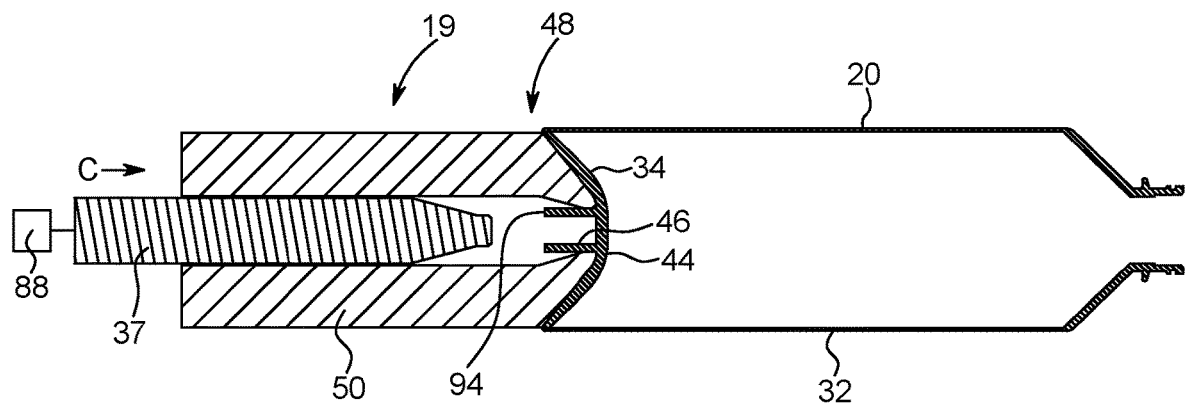
FIG. 19D is a side cross-sectional view of the syringe and the syringe engagement mechanism in a second position.
Figure 19E:
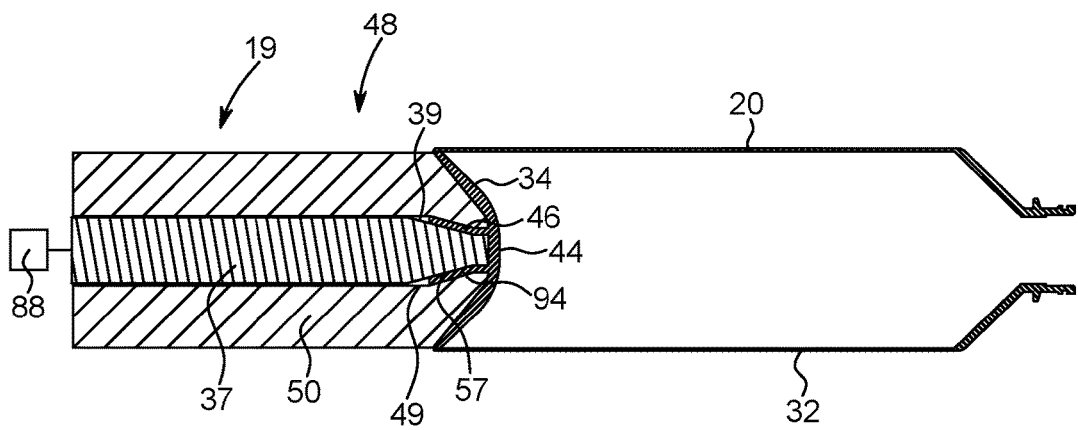
FIG. 19E is a side cross-sectional view of the syringe and the syringe engagement mechanism in a third position.

With reference to FIGS. 19C-19E, the piston 19 has an outer piston sleeve 50 with an abutment section 52 for contacting the end wall 34 of the syringe 20. The abutment section 52 may be shaped to correspond to the shape of the end wall 34 such that the abutment section 52 is in surface-to-surface contact with at least a portion of the end wall 34. The abutment section 52 defines a surface over which the sidewall 32 of the syringe 20 may roll over during a filling or dispensing process by reciprocal movement of the piston 19. An opening 55 is formed in a central portion of the abutment section 52. The opening 55 is configured to receive at least a portion of the engagement portion 46 of the syringe 20. Desirably, an inner diameter of the opening 55 is larger than an outer diameter of the widest portion of the engagement portion 46 to allow free insertion of the engagement portion 46 into the opening 55. An inner surface of the outer piston sleeve 50 may narrow at the distal end of the outer piston sleeve 50. The engagement portion 46 of the syringe 20 is configured to contact at least a portion of the inner surface of the outer piston sleeve 50 when the central rod 37 engages the engagement portion 46.

The central rod 37 may have a distal end with a conical portion 39. The conical portion 39 is configured for contacting the inner portion of the sidewall 94 of the engagement portion 46. The central rod 37 is axially movable relative to the outer piston sleeve 50. Axial movement of the central rod 37 is independent of the axial movement of the outer piston sleeve 50. The movement of the central rod 37 relative to the outer piston sleeve 50 is configured to allow engagement or disengagement of the central rod 37 with the engagement portion 46 of the syringe 20.

With continued reference to FIGS. 19C-19E, to connect the piston 19 with the syringe 20, the piston 19 is moved distally in the direction of arrow A shown in FIG. 19C toward the end wall 34 of the syringe 20. Prior to the abutment section 52 contacting the end wall 34, the central rod 37 is moved proximally in the direction of arrow B to open the opening 55 in the abutment section 52. As the abutment section 52 contacts the end wall 34 of the syringe 20, the engagement portion 46 is received within the opening 55 of the abutment section 52. The central rod 37 is then moved distally in the direction of arrow C shown in FIG. 19D until the conical portion 39 of the central rod 37 is inserted into the annular space 47 of the engagement portion 46. Due to the conical shape of the conical portion 39, the sidewall 94 of the engagement portion 46 is split into a plurality of sidewall segments (see FIG. 19B). The sidewall 94 of the engagement portion 46 is retained in a space 49 between the inner surface 57 of the outer piston sleeve 50 and the outer surface of the conical portion 39 of the central rod 37 (FIG. 19E). With the engagement of the sidewall 94 of the engagement portion 46 with the abutment section 52 and the central rod 37, the piston 19 can be moved in a proximal direction to fill the interior of the syringe 20 with fluid or in the distal direction to deliver the fluid from the interior of the syringe 20.

With reference to FIGS. 20A-20E, a syringe 20 in combination with an engagement mechanism 48 (shown in FIGS. 20C-20E) of a piston 19 is shown in accordance with another example of the present disclosure. The syringe 20 and the piston 19 shown in FIGS. 20A-20E are substantially similar to the syringe 20 and the piston 19 shown in FIGS. 19A-19E. As the disclosure of the syringe 20 and the piston 19 shown in FIGS. 19A-19E is generally applicable to the syringe 20 and the piston 19 shown in FIGS. 20A-20E, only the relative differences between the syringes and pistons are discussed hereinafter.

Figure 20A:
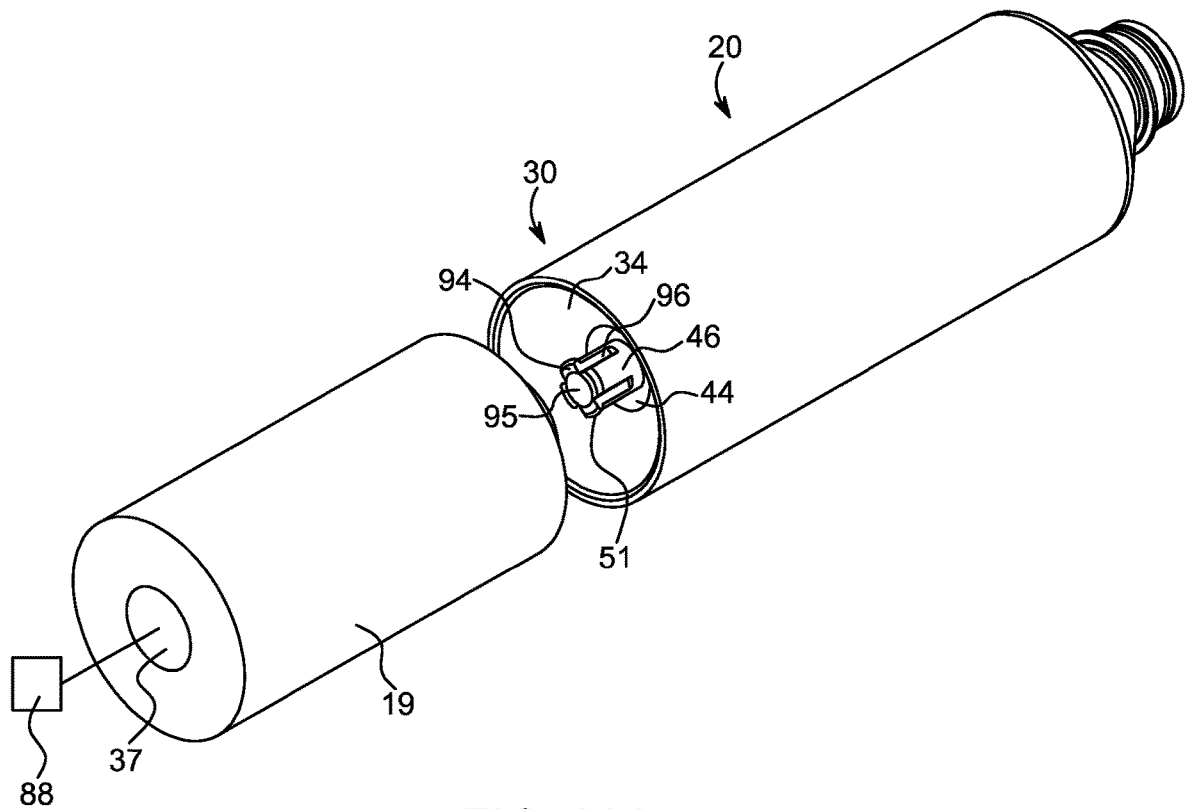
FIG. 20A is an exploded perspective view of a syringe and a piston having a syringe engagement mechanism in accordance with one example of the present disclosure.
Figure 20B:
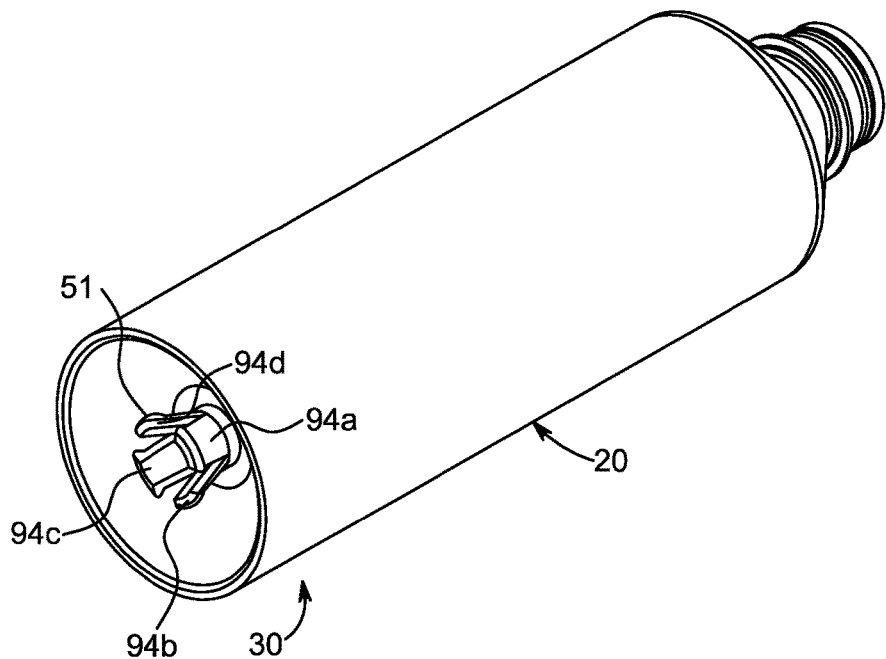
FIG. 20B is a rear perspective view of the syringe shown in FIG. 20A shown after engagement with the syringe engagement mechanism.
Figure 20C:
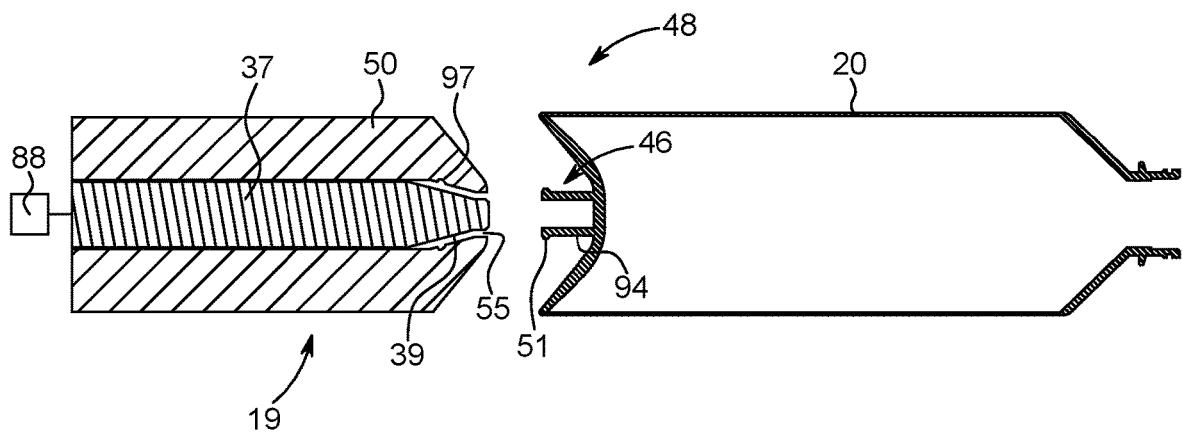
FIG. 20C is a side cross-sectional view of the syringe and the syringe engagement mechanism in a first position.
Figure 20D:
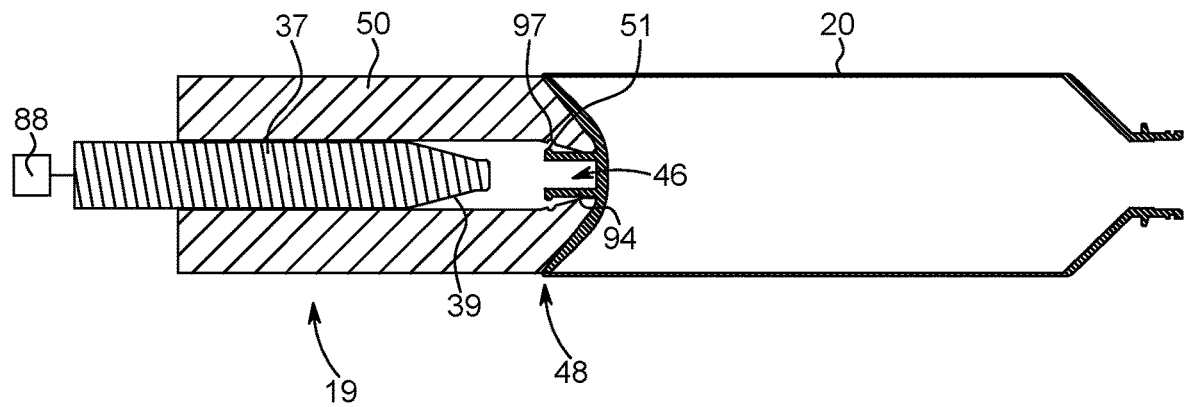
FIG. 20D is a side cross-sectional view of the syringe and the syringe engagement mechanism in a second position.
Figure 20E:
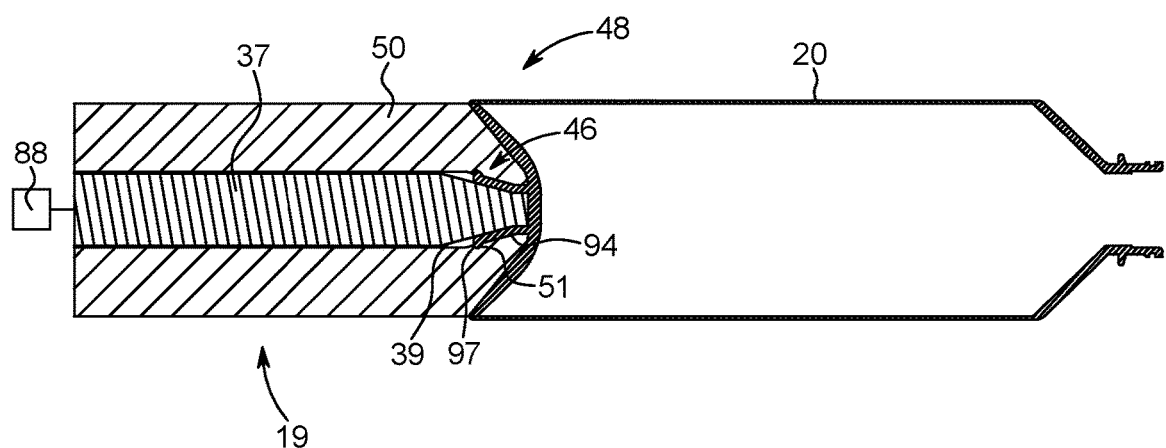
FIG. 20E is a side cross-sectional view of the syringe and the syringe engagement mechanism in a third position.

With reference to FIGS. 20A-20B, the engagement portion 46 has an annular shape with a sidewall 94 defining a central opening 95 configured to receive the central rod 37. The sidewall 94 may be expandable between a first configuration shown in FIG. 20A and a second configuration shown in FIG. 20B. For example, the sidewall 94 may be a frangible sidewall that separates from a single, circumferential sidewall 94 shown in FIG. 20A, to a plurality of sidewall segments 94a-94d shown in FIG. 20B. In some examples, the sidewall 94 may separate into a plurality of sidewall segments 94a-94d due to interaction with the central rod 37. The sidewall 94 has one or more grooves 96 extending in a direction along a longitudinal axis of the syringe 20 over at least a portion of the longitudinal length of the engagement portion 46. The one or more grooves 96 may have a smaller thickness than the sidewall 94. The one or more grooves 96 define weakened areas of the sidewall 94 such that the sidewall 94 may split into the plurality of sidewall segments 94a-94d along the one or more grooves 96.

With continued reference to FIGS. 20A-20B, the engagement portion 46 has a lip 51 that protrudes radially outward relative to the outer surface of the sidewall 94. The lip 51 may be formed at the proximal end of the engagement portion 46, such as at a terminal end of the engagement portion 46. The lip 51 is configured to be received within a recess 97 on the inner surface of the outer piston sleeve 50. In other examples, the lip 51 may protrude radially inward relative to the inner surface of the sidewall 94 such that the lip 51 is received within the recess 97 formed on the outer surface of the conical portion 39 of the central rod 37.

In further examples, the lip 51 may be formed on one of an outer surface of the central rod 37 and the inner surface of the outer piston sleeve 50, while the recess 97 is formed on the other of the outer surface of the central rod 37 and the inner surface of the outer piston sleeve 50. The lip 51 may be received within at least a portion of the recess 97 when the central rod 37 is at its distal-most position. In this manner, the engagement portion 46 is retained in a space between the inner surface of the outer piston sleeve 50 and the outer surface of the conical portion 39 of the central rod 37. The sidewall of the engagement portion 46 may be compressed or deformed at the interface between the lip 51 and the recess 97.

FIGS. 21A-21E show a proximal end 30 of a syringe 20 in combination with an engagement mechanism 48 (shown in FIGS. 19C-19E) of a piston 19 in accordance with another example of the present disclosure. The components of the syringe 20 shown in FIGS. 21A-21E are substantially similar or identical to the components of the syringe 20 described herein with reference to FIGS. 2A-2B, except where otherwise noted. The engagement portion 46 of the syringe 20 is configured for interacting with one or more surfaces of the engagement mechanism 48 that engage and disengage the engagement portion 46 of the syringe 20 with movement of a central rod 37.

Figure 21A:
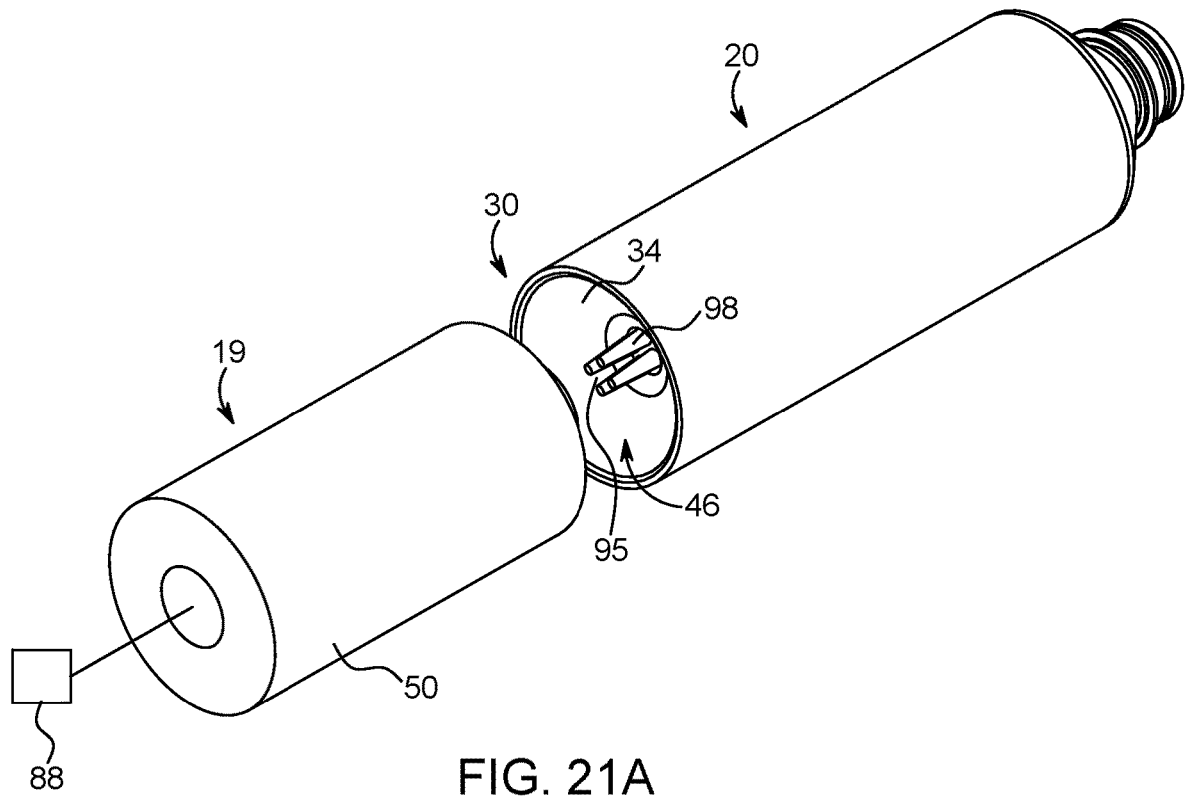
FIG. 21A is an exploded perspective view of a syringe and a piston having a syringe engagement mechanism in accordance with one example of the present disclosure.
Figure 21B:
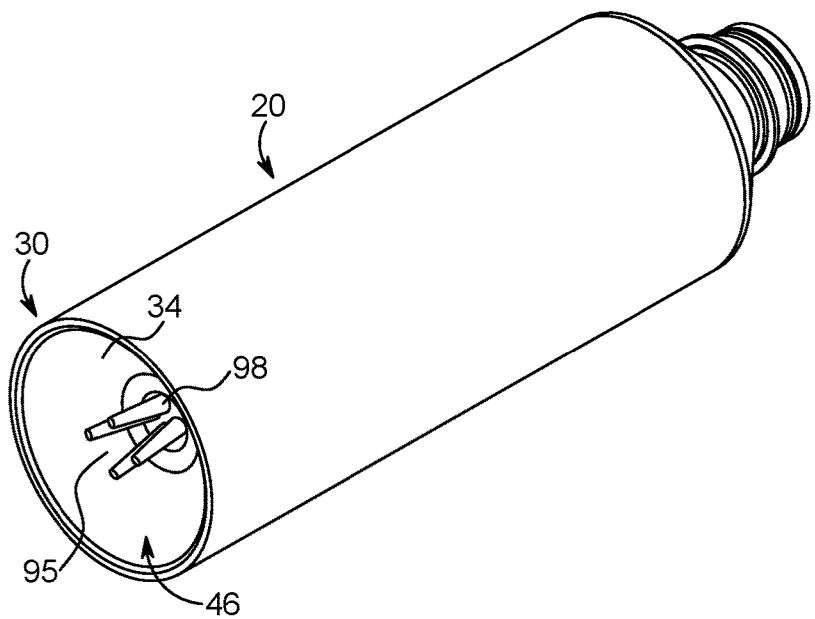
FIG. 21B is a rear perspective view of the syringe shown in FIG. 21A shown after engagement with the syringe engagement mechanism.

With specific reference to FIG. 21A, the end wall 34 of the syringe 20 may have a piston engagement portion 46 extending proximally from the end wall 34. In some examples, the engagement portion 46 may extend in a proximal direction along a longitudinal axis of the syringe 20 from an approximate midpoint of the end wall 34. The engagement portion 46 may have a plurality of engagement elements 98 defining a central opening 95 therebetween configured to receive the central rod 37. The engagement elements 98 may be expandable between a first configuration shown in FIG. 21A and a second configuration shown in FIG. 21B. For example, the engagement elements 98 may be arranged in a first position such that the engagement elements 98 define a circle with a first diameter. The engagement elements 98 may then be expanded to a second position such that the engagement elements 98 are spread apart radially to define a circle with a second diameter larger than the first diameter. In some examples, the engagement elements 98 may separate due to interaction with the central rod 37. The engagement elements 98 may have a circular or any other cross-sectional shape.

The engagement portion 46 may be substantially flush with the proximal end 30 of the syringe 20, or it may extend proximally beyond the proximal end 30 of the syringe 20 or be recessed distally into the dome-shaped proximal end 30. The engagement portion 46 may be monolithically formed with the syringe body, or it may be removably or non-removably attached to the end wall 34, such as by welding, adhesion, or clip attachment, or other fastening mechanism. In some examples, the plurality of engagement elements 98 of the engagement portion 46 may form a substantially circular shape. In other examples, the engagement elements 98 may form a star shape, or a shape having any regular or irregular geometric shape.

The engagement portion 46 is configured for interacting with the central rod 37 of the piston 19 of the fluid injector 10, as described herein. In various examples, the proximal/distal movement of the central rod 37 may be effected by a proximal/distal movement of the piston 19, such as due to linear or rotational movement of the central rod 37. In some examples, the proximal/distal movement of the central rod 37 may be independent of the proximal/distal movement of the piston 19, such as by a drive mechanism 88. The drive mechanism 88 may be electrically, pneumatically, and/or hydraulically operated. For example, the drive mechanism 88 may have an electric or electromechanical mechanism, such as a linear or rotary electric motor, or a solenoid. In some examples, the drive mechanism 88 may be selectively energized, such as during proximal or distal movement of the central rod 37. In other examples, the rod drive mechanism 88 may be constantly energized, regardless of whether the central rod 37 is stationary, or moving in the proximal or distal direction. The drive mechanism 88 may have a locking mechanism (not shown) for locking the central rod 37 in its position.

Figure 21C:
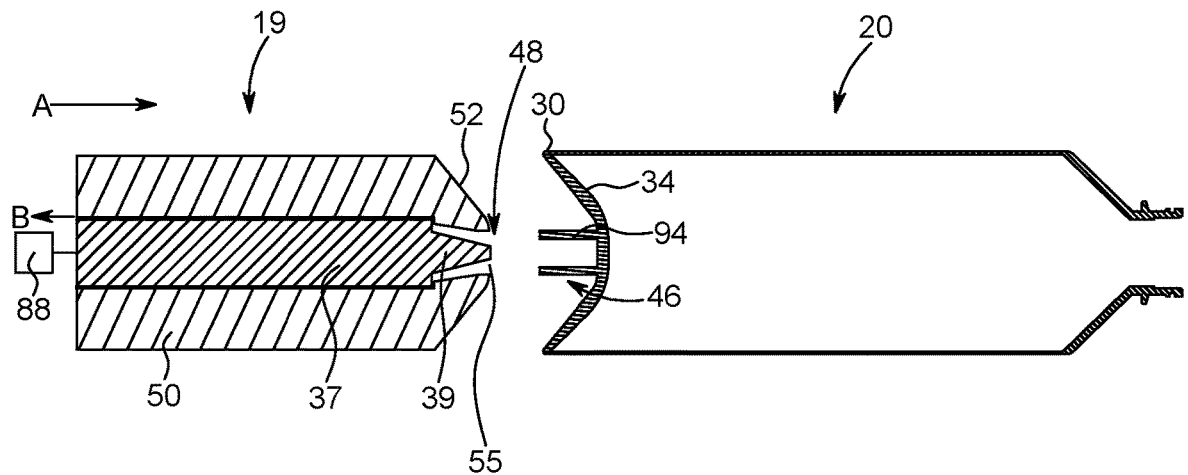
FIG. 21C is a side cross-sectional view of the syringe and the syringe engagement mechanism in a first position.
Figure 21D:
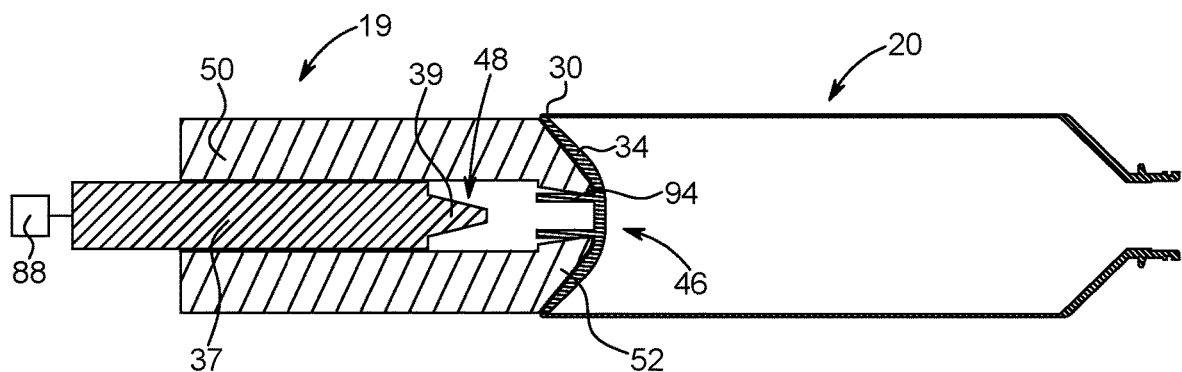
FIG. 21D is a side cross-sectional view of the syringe and the syringe engagement mechanism in a second position.
Figure 21E:
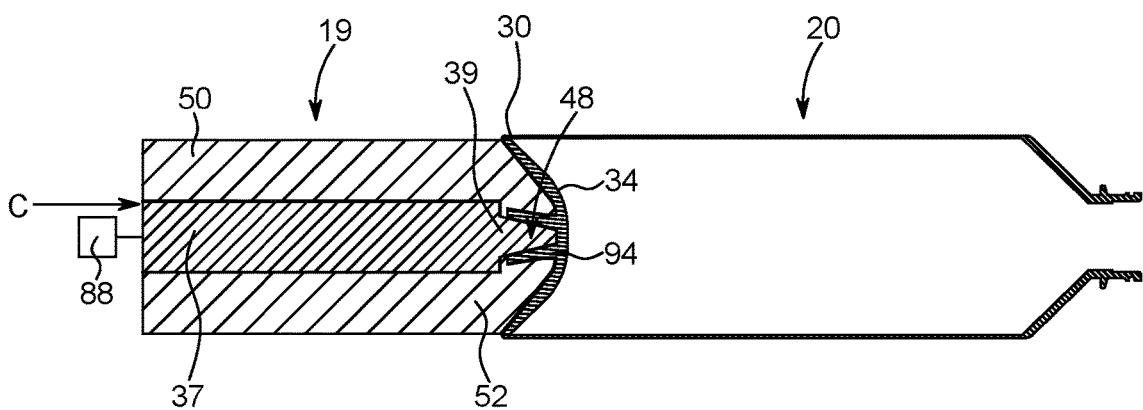
FIG. 21E is a side cross-sectional view of the syringe and the syringe engagement mechanism in a third position.

With reference to FIGS. 21C-21E, the piston 19 has an outer piston sleeve 50 with an abutment section 52 for contacting the end wall 34 of the syringe 20. The abutment section 52 may be shaped to correspond to the shape of the end wall 34 such that the abutment section 52 is in surface-to-surface contact with at least a portion of the end wall 34. The abutment section 52 defines a surface over which the sidewall 32 of the syringe 20 may roll over during a filling or dispensing process by reciprocal movement of the piston 19. An opening 55 is formed in a central portion of the abutment section 52. The opening 55 is configured to receive at least a portion of the engagement portion 46 of the syringe 20. Desirably, an inner diameter of the opening 55 is larger than an outer diameter of the widest portion of the engagement portion 46 to allow free insertion of the engagement portion 46 into the opening 55. An inner surface of the outer piston sleeve 50 may narrow at the distal end of the outer piston sleeve 50. The engagement portion 46 of the syringe 20 is configured to contact at least a portion of the inner surface of the outer piston sleeve 50 when the central rod 37 engages the engagement portion 46.

The central rod 37 may have a distal end with a conical portion 39. The conical portion 39 is configured for contacting the inner portion of the sidewall of the engagement portion 46. The central rod 37 is axially movable relative to the outer piston sleeve 50. Axial movement of the central rod 37 is independent of the axial movement of the outer piston sleeve 50. The movement of the central rod 37 relative to the outer piston sleeve 50 is configured to allow engagement or disengagement of the central rod 37 with the engagement portion 46 of the syringe 20.

With continued reference to FIGS. 21C-21E, to connect the piston 19 with the syringe 20, the piston 19 is moved distally in the direction of arrow A shown in FIG. 21C toward the end wall 34 of the syringe 20. Prior to the abutment section 52 contacting the end wall 34, the central rod 37 is moved proximally in the direction of arrow B to open the opening 55 in the abutment section 52. As the abutment section 52 contacts the end wall 34 of the syringe 20, the engagement portion 46 is received within the opening 55 of the abutment section 52. The central rod 37 is then moved distally in the direction of arrow C shown in FIG. 21D until the conical portion 39 of the central rod 37 is inserted into the central opening 95 of the engagement portion 46. Due to the conical shape of the conical portion 39, the engagement elements 98 of the engagement portion 46 are spread apart to a larger diameter circular configuration (see FIG. 21B). The engagement elements 98 of the engagement portion 46 are retained in a space between the inner surface of the outer piston sleeve 50 and the outer surface of the conical portion 39 of the central rod 37 (FIG. 21E). With the engagement of the engagement elements 98 of the engagement portion 46 with the abutment section 52 and the central rod 37, the piston 19 can be moved in a proximal direction to fill the interior of the syringe 20 with fluid or in the distal direction to deliver the fluid from the interior of the syringe 20.

Figure 22:
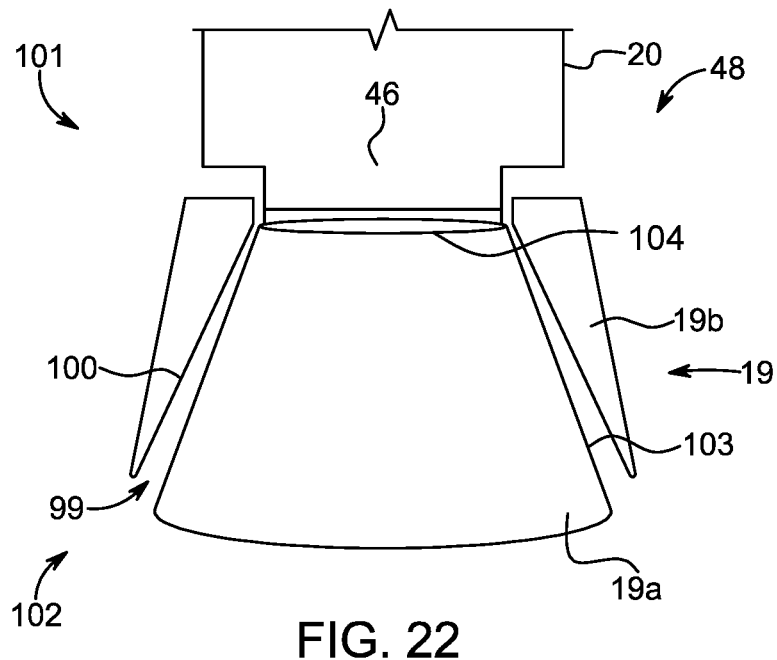
FIG. 22 is a side cross-sectional view of a syringe and a piston having a syringe engagement mechanism in accordance with one example of the present disclosure.

With reference to FIG. 22, an engagement mechanism 48 of a piston 19 is shown in accordance with another example of the present disclosure. The piston 19 has a first annular portion 19a and a second annular portion 19b that is concentric with the first annular portion 19a and positioned such that it surrounds the first annular portion 19a. The first annular portion 19a has a central opening 104 configured for receiving the engagement portion 46 of a syringe 20. An outer surface 103 of the first annular portion 19a has a conical shape such that an outer diameter of the first annular portion 19a increases in a direction from a distal end 101 toward a proximal end 102 of the piston 19.

With continued reference to FIG. 22, the first annular portion 19a is received within a central opening 99 of the second annular portion 19b. An inner surface 100 of the second annular portion 19b has a conical shape such that an inner diameter of the second annular portion 19b increases in a direction from the distal end 101 toward the proximal end 102 of the piston 19. In some examples, the inner surface 100 of the second annular portion 19b may be complementary to an outer surface 103 of the first annular portion 19a.

The first and second annular portions 19a, 19b are movable axially relative to one another by a drive mechanism (not shown), such as a drive mechanism 88 described herein with reference to FIGS. 7A-7B. For example, the second annular portion 19b is movable in an axial direction relative to the first annular portion 19a between a first position, wherein the first annular portion 19a is engaged with the engagement portion 46 of the syringe 20, and a second position, wherein the engagement portion 46 of the syringe 20 can be freely inserted into or removed from the first annular portion 19a. Relative movement of the first and second annular portions 19a, 19b toward each other clamps the second annular portion 19b around the first annular portion 19a. Clamping of the second annular portion 19b around the first annular portion 19a reduces a diameter of the central opening 104 of the first annular portion 19a. In this manner, when the engagement portion 46 of the syringe is positioned within the central opening 104 of the first annular portion 19a, the engagement portion 46 is retained within the piston 19 by frictional contact with an inner surface of the first annular portion 19a. Relative movement of the first and second annular portions 19a, 19b away from each other releases the clamping engagement of the second annular portion 19b with the first annular portion 19a, thereby allowing the engagement portion 46 of the syringe to be removed from the central opening 104 of the first annular portion 19a.

Figure 23:
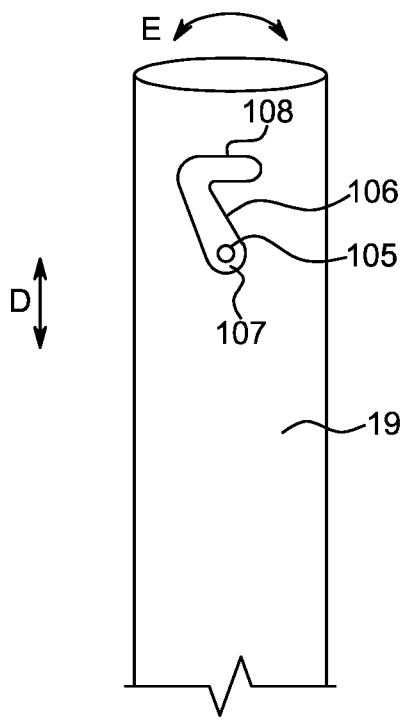
FIG. 23 is a side cross-sectional view of a syringe and a piston having a syringe engagement mechanism in accordance with one example of the present disclosure.

With reference to FIG. 23, the one or more pins 105 on the piston 19 may be movable within a track 106 on a second portion of the piston 19, such as the outer sleeve (not shown). The track 106 has a first end 107 and a second end 108, wherein the one or more pins 105 are movable from the first end 107 toward the second end 108 with axial movement of the piston 19 in a proximal-to-distal direction in a direction of arrow D in FIG. 23 and/or with rotational movement of the piston 19 about its longitudinal axis in a clockwise or counterclockwise direction in a direction of arrow E in FIG. 23. Such pin 105 and track 106 arrangement is similar to the dowel 63 and slot 65 arrangement described herein with reference to FIGS. 4A-4B.

Figure 24:
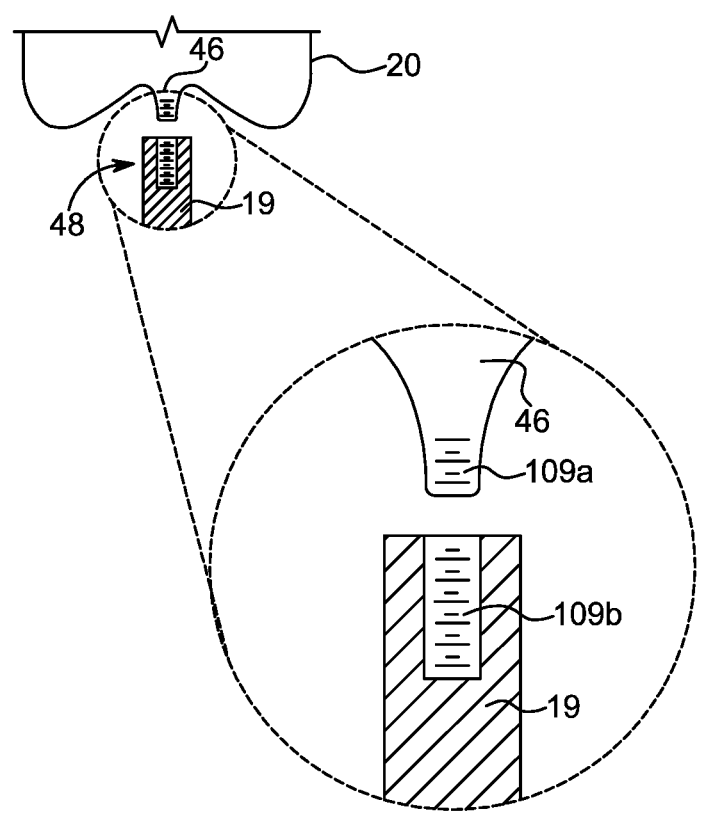
FIG. 24 is a side cross-sectional view of a syringe and a piston having a syringe engagement mechanism in accordance with one example of the present disclosure.

With reference to FIG. 24, an engagement mechanism 48 of a piston 19 is shown in accordance with another example of the present disclosure. The engagement mechanism 48 is configured for releasably connecting the engagement portion 46 of a syringe 20 with the piston 19. In some examples, the piston 19 has a first threaded portion 109a that is configured for threadably connecting with a second threaded portion 109b on the engagement portion 46 of the syringe 20. In some examples, the first threaded portion 109a is a male threaded portion that is configured for being threadably inserted into the second threaded portion 109b that is configured as a female threaded portion. In other examples, the first threaded portion 109a is a female threaded portion that is configured for threadably receiving the second threaded portion 109b that is configured as a male threaded portion. In other examples, the first threaded portion 109a on the piston 19 may have a self-taping thread that is threaded into the engagement portion 46 which is optionally non-threaded. The piston 19 may be rotatably driven by a drive mechanism (not shown) in a first direction, such as in a clockwise direction, to engage the first threaded portion 109a with the second threaded portion 109b, and in a second direction opposite the first direction, such as in a counter-clockwise direction, to disengage the first threaded portion 109a from the second threaded portion 109b.

Figure 25A:
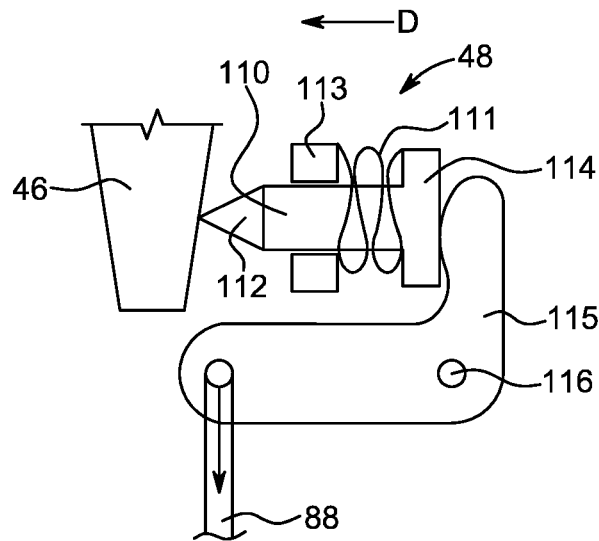
FIGS. 25A-25B are side views of a syringe and a piston having a syringe engagement mechanism in accordance with one example of the present disclosure.
Figure 25B:
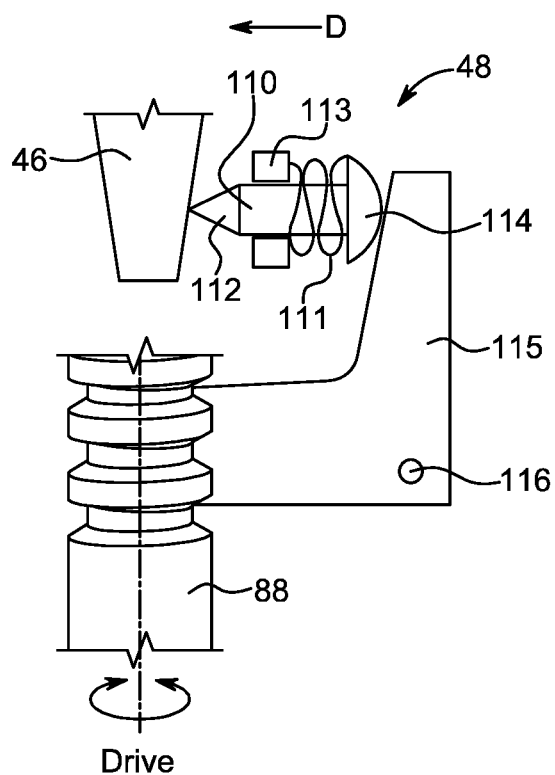

With reference to FIGS. 25A-25B, an engagement mechanism 48 of a piston 19 is shown in accordance with another example of the present disclosure. The engagement mechanism 48 includes at least one pin 110 that is movable radially inward and outward relative to an engagement portion 46 of the syringe (not shown). The at least one pin 110 may have a pointed first end 112 that is configured for contacting the body of the engagement portion 46. In some examples, the at least one pin 110 is biased to a first or disengaged position (shown in FIGS. 25A-25B) by a biasing mechanism 111, such as a spring or a Belleville washer. A stop surface 113 may be provided to limit the movement of the pin 110 in a direction toward the engagement portion 46. A second end 114 of the at least one pin 110 is in contact with a pivoting lever 115. Pivoting movement of the lever 115 about its pivot pin 116 causes at least a portion of the lever 115 to contact the second end 114 of the at least one pin 110 and urge the at least one pin 110 in a radially inward direction of arrow D toward the engagement portion 46 of the syringe. The pivoting movement of the lever 115 may be effected by a drive mechanism 88, such as linear drive mechanism (FIG. 25A) or a rotational drive mechanism (FIG. 25B).

Figure 26A:
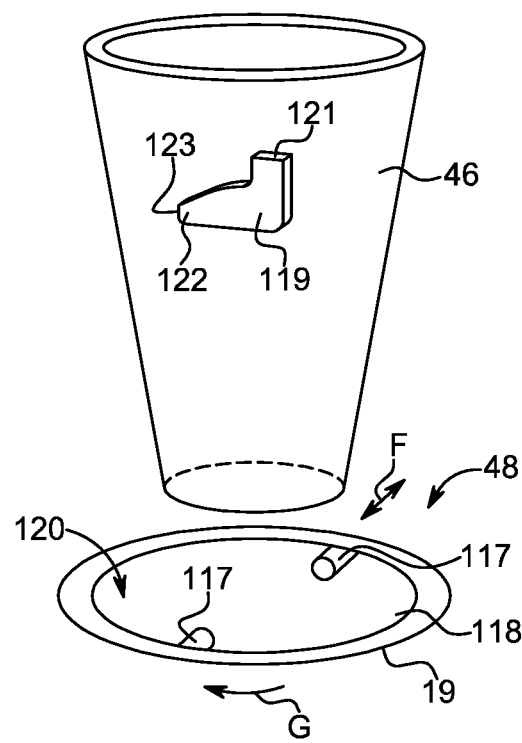
FIG. 26A is a perspective view of a syringe and a piston having a syringe engagement mechanism in accordance with one example of the present disclosure.
Figure 26B:
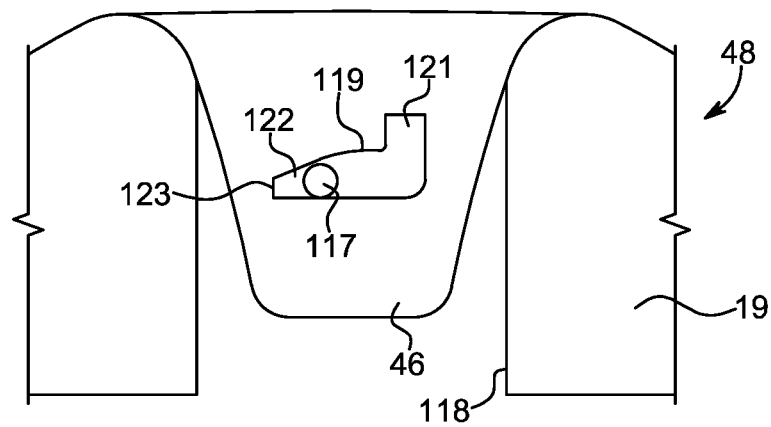
FIG. 26B is a side cross-sectional view of the syringe and the syringe engagement mechanism shown in FIG. 26A.

With reference to FIGS. 26A-26B, an engagement mechanism 48 of a piston 19 is shown in accordance with another example of the present disclosure. The engagement mechanism 48 is a bayonet-type mechanism having one or more pins 117 extending radially inward from an inner surface 118 of a hollow piston 19 and configured for interacting with one or more slots 119 on the engagement portion 46 of the syringe 20. In some examples, the engagement mechanism 48 has a pair of pins 117 diametrically opposed to one another. The pins 117 are radially extendable and retractable relative to the inner surface 118 of the piston 19 in a direction of arrow F in FIG. 26A. For example, the pins 117 may be fully withdrawn (retracted radially outward) into the piston 19 to allow insertion of the engagement portion 46 of the syringe into the central opening of the piston 19.

Upon insertion of the engagement portion 46 of the syringe into a central opening 120 of the hollow piston 19, the pins 117 are extended in a radially inward direction from the inner surface 118 of the piston 19 to enter the slot 119 on the engagement portion 46 of the syringe 20. In some examples, the engagement portion 46 may have the same number of slots 119 as the number of pins 117 on the piston 19 such that each slot 119 receives one pin 117. In some examples, each slot 119 may be L-shaped with a first end 121 and a second end 122. During initial engagement of the piston 19 with the engagement portion 46 of the syringe, each pin 117 is inserted into the first end 121 of the slot 119. The piston 19 is then rotated in the direction of arrow G in FIG. 26A to move the pin 117 within the slot 119 from the first end 121 toward the second end 122. The pin 117 is positioned within the second end 122 of the slot 119 with distal movement of the piston 19 relative to the engagement portion 46 until the pin 117 engages a terminal end 123 of the second end 122 of the slot 119. To release the piston 19 from the engagement portion 46, the pins 117 are retracted in a radially outward direction away from the slots 119 such that the engagement portion 46 of the syringe can be removed from the central opening of the piston 19.

Figure 27A:
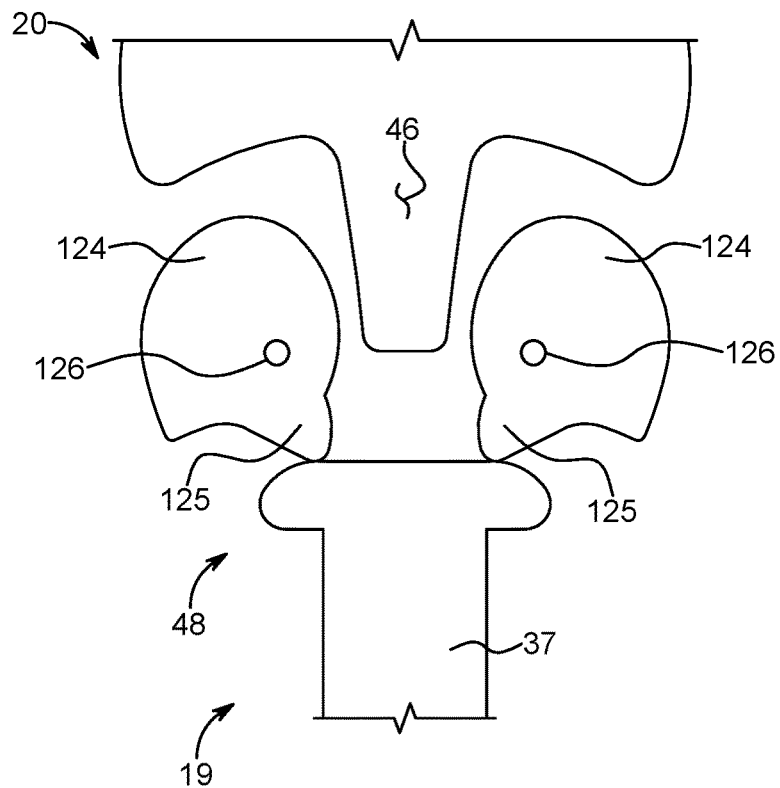
FIG. 27A is a side view of a syringe and a piston having a syringe engagement mechanism in accordance with one example of the present disclosure with the syringe engagement mechanism shown in a first position.
Figure 27B:
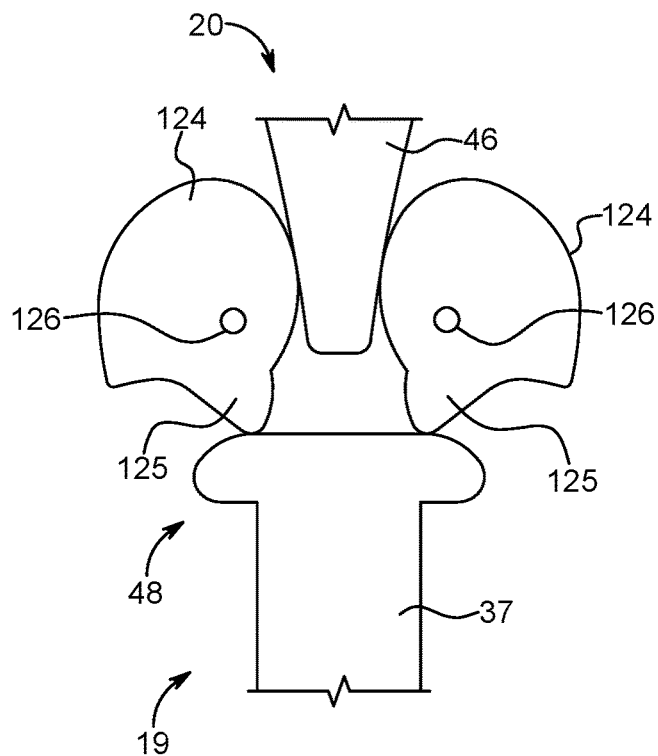
FIG. 27B is a side view of the syringe engagement mechanism of FIG. 27A shown in a second position.

Referring now to FIGS. 27A-27B, the proximal end of a syringe 20 is shown in combination with an engagement mechanism 48 of a piston 19 in accordance with another example of the present disclosure. The engagement portion 46 of the syringe 20 is configured for interacting with one or more rotating cam members 124. In an unlocked state as shown in FIG. 27A, the cam members 124 are radially moveable with respect to the engagement portion 46 of the syringe 20. In a locked state as shown in FIG. 27B, a central or actuating rod 37 moving in proximal/distal direction engages a lobe 125 on each of the cam members 124, causing each cam member 124 to rotate about a respective pivot pin 126. Rotating the cam members 124 in this manner causes the cam members 124 to engage the engagement portion 46 of the syringe 20. In some examples, proximal/distal movement of the actuating rod 37 may be dependent upon proximal/distal movement of the piston 19. In other examples, proximal/distal movement of the central rod 37 may be independent of the proximal/distal movement of the piston 19. For example, the actuating rod 37 may be controlled by a rod drive mechanism substantially similar to the drive mechanism 88 described herein with reference to FIGS. 7A-7B.

Figure 28:
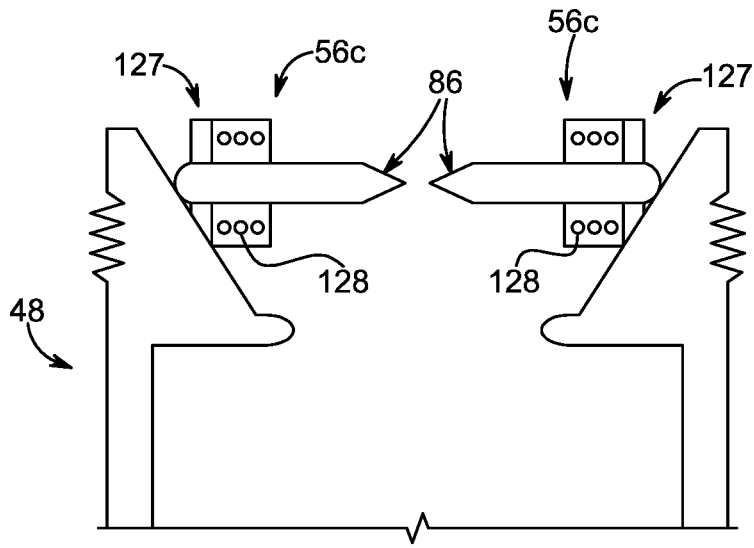
FIG. 28 is a side cross-sectional view of a syringe and a piston having a syringe engagement mechanism in accordance with one example of the present disclosure.

Referring now to FIG. 28, an engagement mechanism 48 in accordance with another example of the present disclosure includes one or more electrically actuated engagement elements 56c moveable in a radial direction with respect to an engagement portion of a syringe (not shown). In some examples, each engagement element 56c has a pointed terminal end 86 for contacting the outer surface of the engagement portion of the syringe, substantially as described herein with reference to the engagement of the engagement elements 56 with the engagement portion 46 of the syringe 20 in FIGS. 3A-3B. Movement of each of the engagement elements 56c may be effected by respective actuators 127, causing the engagement elements 56c to move in the radial direction to either engage or disengage the engagement portion of the syringe. In various examples, each actuator 127 may include a spring 128 made from a shape-memory alloy such as Nitinol, such that application of an electrical charge to the spring 128 causes the actuator 127 to retract in the radial direction. In this manner, each actuator 127 may cause the corresponding engagement element 56c to disengage from the engagement portion of the syringe. Removal of the electrical charge from the spring 128 causes the actuator 127 to return to an engaged position with respect to the engagement portion of the syringe. In some examples, removal of the electrical charge from the spring 128 causes the actuator 127 to return to a disengaged position with respect to the engagement portion of the syringe.

Figure 29:
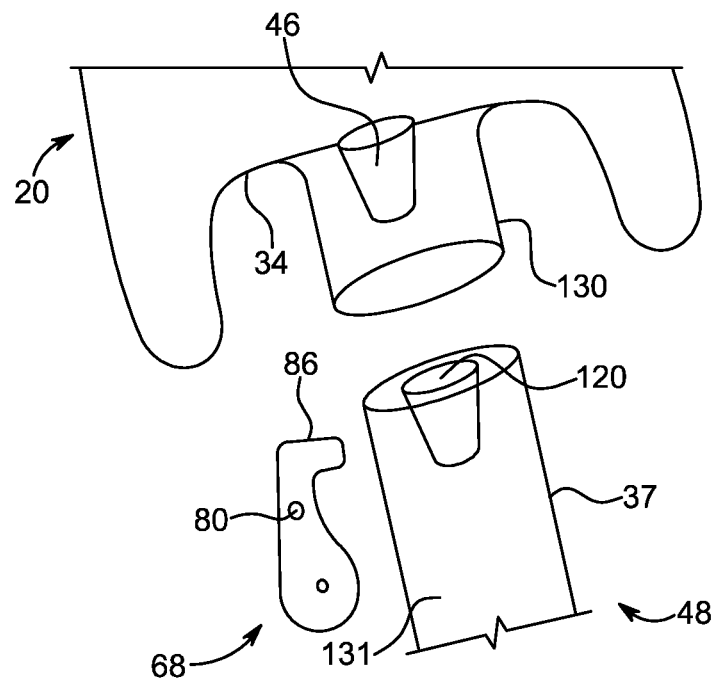
FIG. 29 is a side cross-sectional view of a syringe and a piston having a syringe engagement mechanism in accordance with one example of the present disclosure.

Referring now to FIG. 29, an engagement mechanism 48 in accordance with another example of the present disclosure is shown in combination with the proximal end 30 of a syringe 20. The components of the syringe 20 shown in FIG. 29 are substantially similar or identical to the components of the syringe 20 described herein with reference to FIGS. 2A-2B except where otherwise noted. The syringe 20 in FIG. 29 further includes a flexible sleeve 130 arranged surrounding the engagement portion 46. The engagement mechanism 48 includes one or more engagement arms 68 rotatable around respective pivot pins 80, substantially similar to the engagement arms 68 and pivot pins 80 described herein with reference to FIGS. 10A-11D. In some examples, the engagement arms 68 are limited to the extent to which they can rotate about the pivot pins 80. For example, the engagement arms 68 may be limited to rotate so far as to engage the flexible sleeve 130. The central rod 37 has a central opening 120 configured to receive the engagement portion 46 of the syringe 20. When the engagement portion 46 of the syringe 20 is inserted into the central opening 120 of the central rod 37, the flexible sleeve 130 is positioned between an exterior surface 131 of the central rod 37 and the engagement arms 68. With movement of the engagement arms 68 in a radially inward direction such that the terminal end 86 thereof engages the exterior surface of the flexible sleeve 130, the flexible sleeve 130 is retained on the central rod 37 such that movement of the central rod 37 in a proximal/distal direction also causes a corresponding movement of the syringe 20.

Proximal/distal movement of the central rod 37 may be controlled by a rod drive mechanism, substantially similar to the rod drive mechanism 88 described herein with reference to FIGS. 7A-7B. In some examples, movement of the engagement arms 68 between a closed position and an open position may be based on the proximal/distal movement of the central rod 37. In other examples, movement of the engagement arms 68 may be independent of the movement of the central rod 37.

Figure 30:
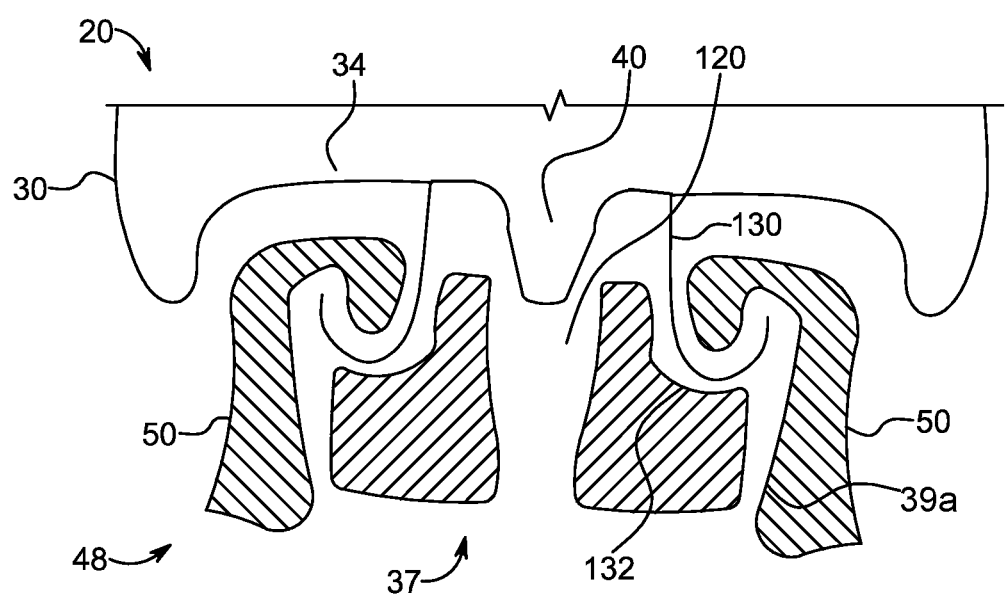
FIG. 30 is a side cross-sectional view of a syringe and a piston having a syringe engagement mechanism in accordance with one example of the present disclosure.

Referring now to FIG. 30, a proximal end 30 of a syringe 20 is shown in combination with an engagement mechanism 48 in accordance with another example of the present disclosure. The example shown in FIG. 30 is substantially similar to the example of FIG. 29. Therefore, only the differences between the syringe 20 and the engagement mechanism 48 of FIG. 29 and the syringe 20 and the engagement mechanism 48 of FIG. 30 are discussed hereinafter.

The flexible sleeve 130 of the engagement portion 46 of the syringe 20 is made from a resilient material such that the flexible sleeve 130 may stretch both radially and longitudinally without breaking. The distal end of the central rod 37 has an arcuate profile 132 corresponding to a complementary arcuate profile 39a of the outer piston sleeve 50. Due to the arcuate profiles of the central rod 37 and the outer piston sleeve 50, the flexible sleeve 130 of the engagement portion 46 deforms as the central rod 37 moves distally into abutment with the end wall 34 of the syringe 20. The syringe 20 is retained in the outer piston sleeve 50 due to frictional force between the central rod 37, the syringe 20, and the outer piston sleeve 50. As shown in FIG. 30, the central rod 37 may include a central opening 120 to receive a central portion of the engagement portion 46 of the syringe 20.

Figure 31A:
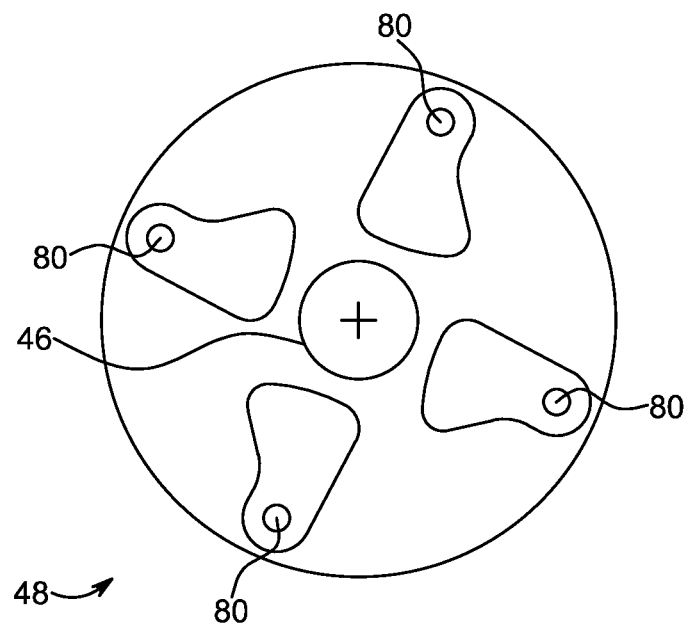
FIG. 31A is a top view of a piston having a syringe engagement mechanism in accordance with another example of the present disclosure.
Figure 31B:
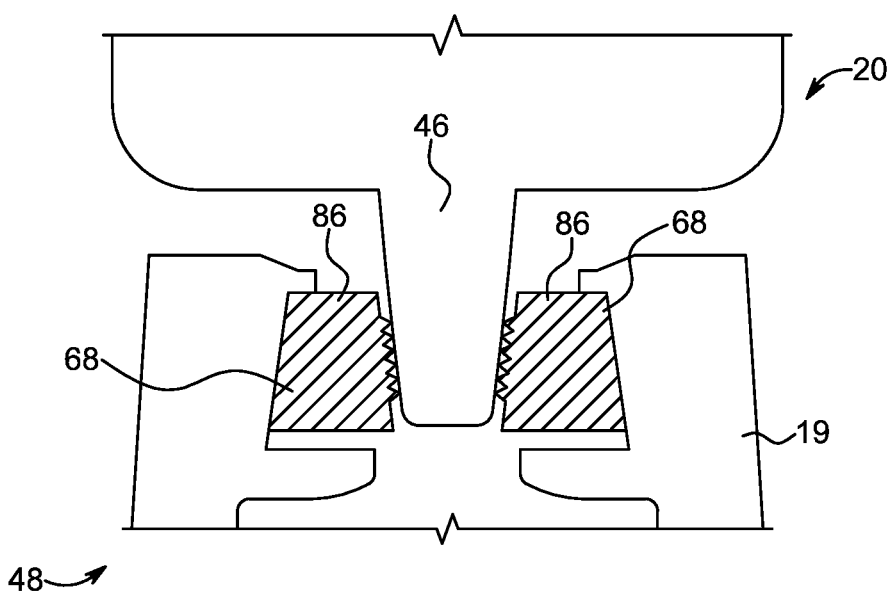
FIG. 31B is a side cross-sectional view of the syringe engagement mechanism shown in FIG. 31A.

Referring now to FIGS. 31A-B, an engagement mechanism 48, in accordance with another example of the present disclosure, includes one or more engagement arms 68, each rotatable about a corresponding pivot pin 80 extending in a direction parallel to the longitudinal axis of a syringe 20. In some examples, as shown in FIG. 31B, each engagement arm 68 may include a pointed terminal end 86 for contacting the outer surface of the engagement portion 46 of the syringe 20, substantially as described herein with reference to the engagement between the pointed terminal ends 86 of the engagement arms 68 with the engagement portion 46 of the syringe 20 shown in FIGS. 10A-11D. In some examples, the engagement arms 68 may be biased toward an engaged or closed state in which the terminal ends 86 engage the engagement portion 46 of the syringe 20. In some examples, rotation of the engagement arms 68 is controlled by a drive mechanism (not shown), such as a motor. In other examples, rotation of the engagement arms 68 may be controlled by any suitable electrical, pneumatic, or hydraulic actuating device.

Figure 32A:
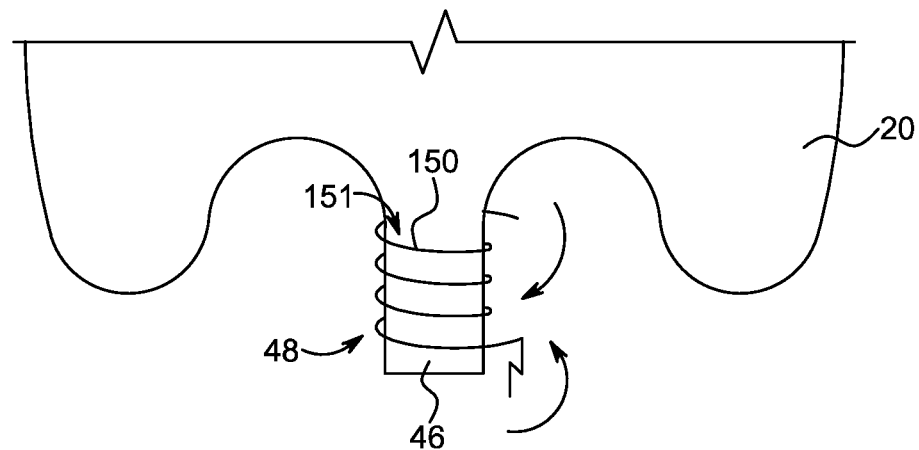
FIG. 32A is a side cross-sectional view of a syringe and a piston having a syringe engagement mechanism in accordance with one example of the present disclosure.

With reference to FIG. 32A, an engagement mechanism 48 of a piston (not shown) is shown in accordance with another example of the present disclosure. The engagement mechanism 48 is configured for releasably connecting the engagement portion 46 of a syringe 20 with the piston. In some examples, the engagement mechanism 48 includes a wrapped spring 150 having a central opening 151 configured for receiving the engagement portion 46 of the syringe 20. By twisting the spring 150 about its longitudinal axis, such as by pulling the terminal ends of the spring 150 in opposite directions, a diameter of the central opening 151 is reduced from a first diameter, wherein the engagement portion 46 can be freely inserted into and removed from the central opening 151, to a second diameter, wherein the inner surface of the spring 150 engages the outer surface of the engagement portion 46.

Figure 32B:
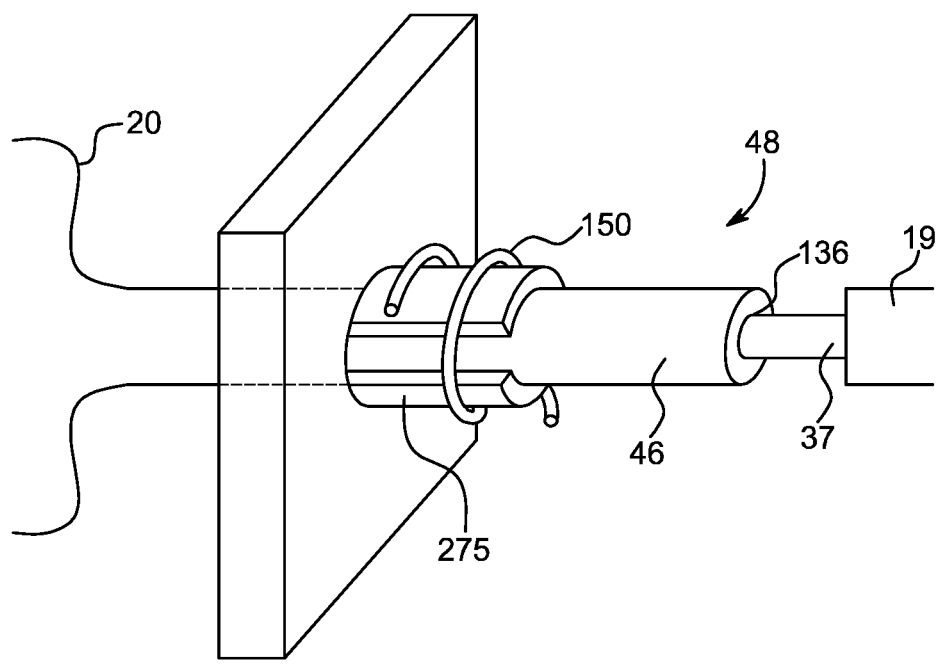
FIG. 32B is a side cross-sectional view of a syringe and a piston having a syringe engagement mechanism in accordance with one example of the present disclosure.

With reference to FIG. 32B, an engagement mechanism 48 of a piston 19 is shown in accordance with another example of the present disclosure. The engagement mechanism 48 is configured for releasably connecting the engagement portion 46 of a syringe 20 with the piston 19. The engagement portion 46 of the syringe 20 has an opening 136 that is configured to receive a central rod 37 of the piston 19. The central rod 37 is movable in a proximal/distal direction to allow insertion into and withdrawal from the opening 136. A split collar 275 extends around an outer surface of the engagement portion 46. The split collar 275 has a longitudinal gap such that the opposing sides of the split collar 275 are movable toward each other to reduce an inner diameter of the split collar 275. In one example, when the split collar 275 is in the compressed engaged position, an inner diameter of the split collar 275 is reduced to contact the outer surface of the engagement portion 46 of the syringe 20. The split collar 275 may be moved between the open disengaged position and the compressed engaged position using a wrapped spring 150, such as the wrapped spring 150 discussed herein with reference to FIG. 32A. By twisting the spring 150 about its longitudinal axis, such as by pulling the terminal ends of the spring 150 in opposite directions, a diameter of the spring 150 is reduced from a first diameter, wherein split collar 275 is opened to allow the engagement portion 46 of the syringe 20 to be freely inserted into and removed from the split collar 275, to a second diameter, wherein the diameter of the spring 150 is reduced, thereby reducing the diameter of the split collar 275 such that the inner surface of the split collar 275 engages the outer surface of the engagement portion 46. In this manner, the engagement portion 46 of the syringe 20 may be compressed between the inner surface of the split collar 275 and the outer surface of the central rod 37.

Figure 33A:
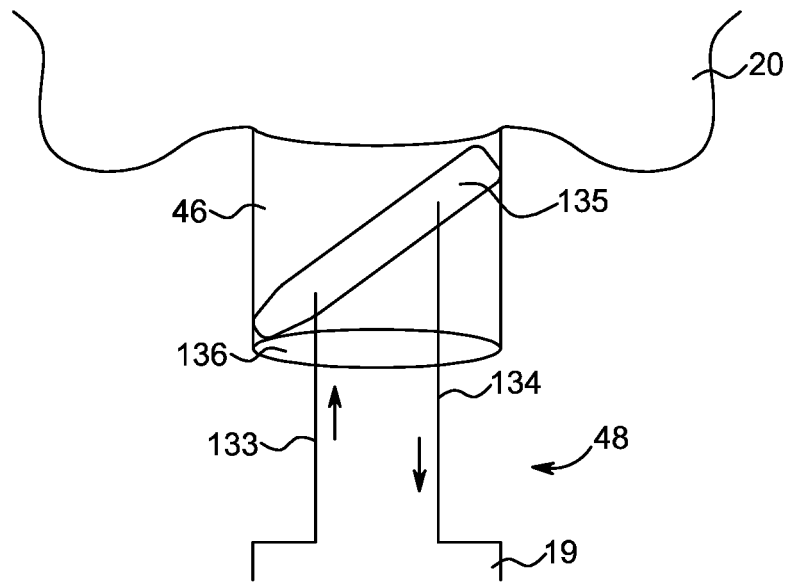
FIG. 33A is a side cross-sectional view of a syringe and a piston having a syringe engagement mechanism in accordance with one example of the present disclosure with the syringe engagement mechanism shown in a first position.
Figure 33B:
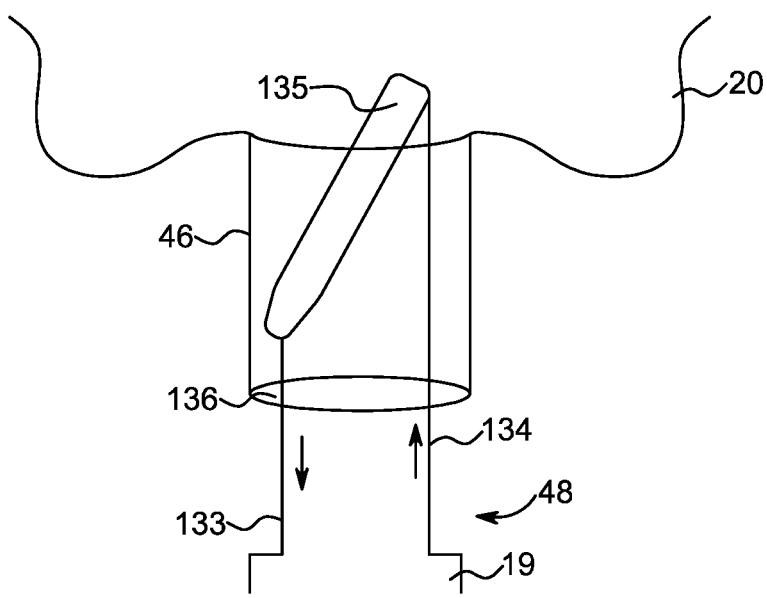
FIG. 33B is a side cross-sectional view of the syringe engagement mechanism and the syringe of FIG. 33A with the syringe engagement mechanism shown in a second position.

With reference to FIGS. 33A and 33B, an engagement mechanism 48 of a piston 19 is shown in accordance with another example of the present disclosure. The engagement mechanism 48 is configured for releasably connecting the engagement portion 46 of a syringe 20 with the piston 19. In some examples, the engagement mechanism 48 includes a pair of posts 133, 134 with a wedge member 135 provided on a distal end of each post 133, 134. The posts 133, 134 and wedge member 135 are received in an opening 136 on the engagement portion 46 of the syringe 20. The piston 19 moves the engagement mechanism 48 distally and proximally within the engagement portion 46. To lock the engagement mechanism 48 with the engagement portion 46, the engagement mechanism 48 is inserted into the opening 136 of the engagement portion 46 with the wedge member 135 positioned at an angle relative to a longitudinal axis of the posts 133, 134. After the engagement mechanism 48 has been inserted into the opening 136 of the engagement portion 46, one of the posts 133, 134 is driven in a distal direction while the other post 133, 134 is pulled in a proximal direction. Alternatively, one of the posts 133, 134 is driven in a distal or proximal direction while the other post 133, 134 is stationary.

As the posts 133, 134 are moved, the wedge member 135 is rotated to a position in which the wedge member 135 contacts the inner surface of the engagement portion 46. In one example, the outer diameter of the wedge member 135 is larger than the inner diameter of the opening 136 such that the wedge member 135 is held in a frictional engagement with the engagement portion 46. After the wedge member 135 contacts the inner surface of the engagement portion 46, the piston 19 can be moved in a proximal direction to fill the interior of the syringe 20 with fluid or in the distal direction to deliver the fluid from the interior of the syringe 20. To release the engagement mechanism 48 from the engagement portion 46, one post 133, 134 is driven in a distal direction while the other post 133, 134 is pulled in a proximal direction so that the wedge member 135 is turned to an angled position relative to the longitudinal axis of the posts 133, 134. Alternatively, one of the posts 133, 134 is driven in a distal or proximal direction while the other post 133, 134 is stationary.

Figure 34A:
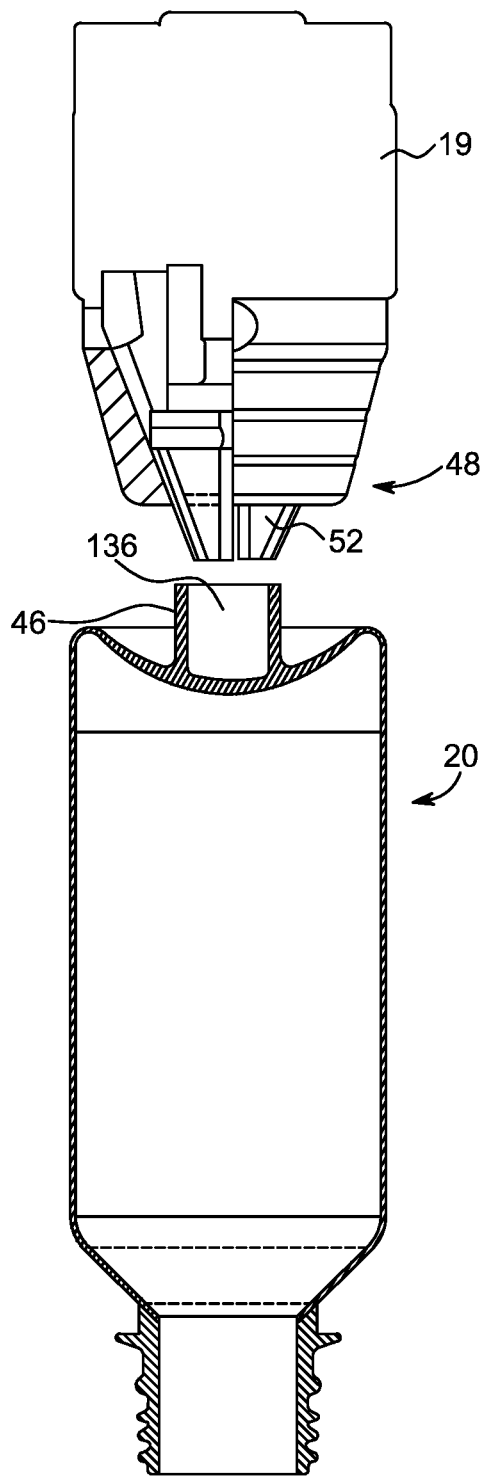
FIG. 34A is a side cross-sectional view of a syringe and a piston having a syringe engagement mechanism in accordance with one example of the present disclosure.
Figure 34B:
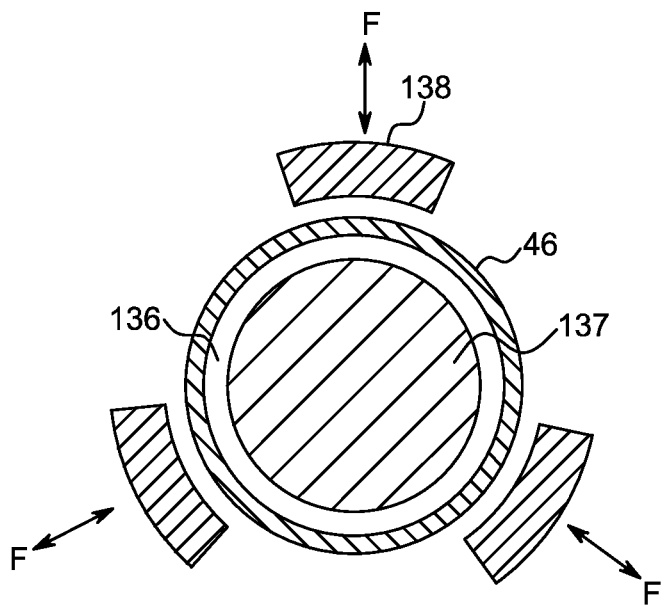
FIG. 34B is a top cross-sectional view of the syringe engagement mechanism and the syringe shown in FIG. 34A.

With reference to FIGS. 34A and 34B, an engagement mechanism 48 of a piston (not shown) is shown in accordance with another example of the present disclosure. The engagement mechanism 48 is configured for releasably connecting the engagement portion 46 of a syringe 20 with the piston. In some examples, the engagement mechanism 48 is a keyless or keyed chuck that configured to releasably engage the engagement portion 46 of the syringe 20. The engagement mechanism 48 includes an inner member 137 and a plurality of contact arms 138 provided in a circular arrangement around the inner member 137. The inner member 137 is configured to be received within an opening 136 of the engagement portion 46. The piston 19 may drive the engagement mechanism 48 towards the engagement portion 46 to insert the inner member 137 into the opening 136.

With continued reference to FIGS. 34A-34B, the contact arms 138 are configured to move between an expanded first position and a contracted second position in a direction of arrow F in FIG. 34B. As the engagement mechanism 48 is driven towards the engagement portion 46, the contact arms 138 are positioned in the expanded first position so that the engagement portion 46 can be received between the inner member 137 and the contact arms 138. After the inner member 137 is inserted into the engagement portion 46, the engagement mechanism 48 is moved to the closed position, such as by rotating at least a portion of the piston 19 to move the contact arms 138 into contact with an outer surface of the engagement portion 46. As the contact arms 138 are moved inwardly towards the inner member 137, the engagement portion 46 of the syringe 20 is clamped between the contact arms 138 and the inner member 137. After the engagement portion 46 is frictionally retained between the contact arms 138 and the inner member 137, the piston 19 can be moved in a proximal direction to fill the interior of the syringe 20 with fluid or in the distal direction to deliver the fluid from the interior of the syringe 20. To release the engagement mechanism 48 from the engagement portion 46, the engagement mechanism 48 is moved to the open position, such as by rotating at least a portion of the piston 19 to move the contact arms 138 in a radially outward direction and out of contact with an outer surface of the engagement portion 46.

Figure 35:
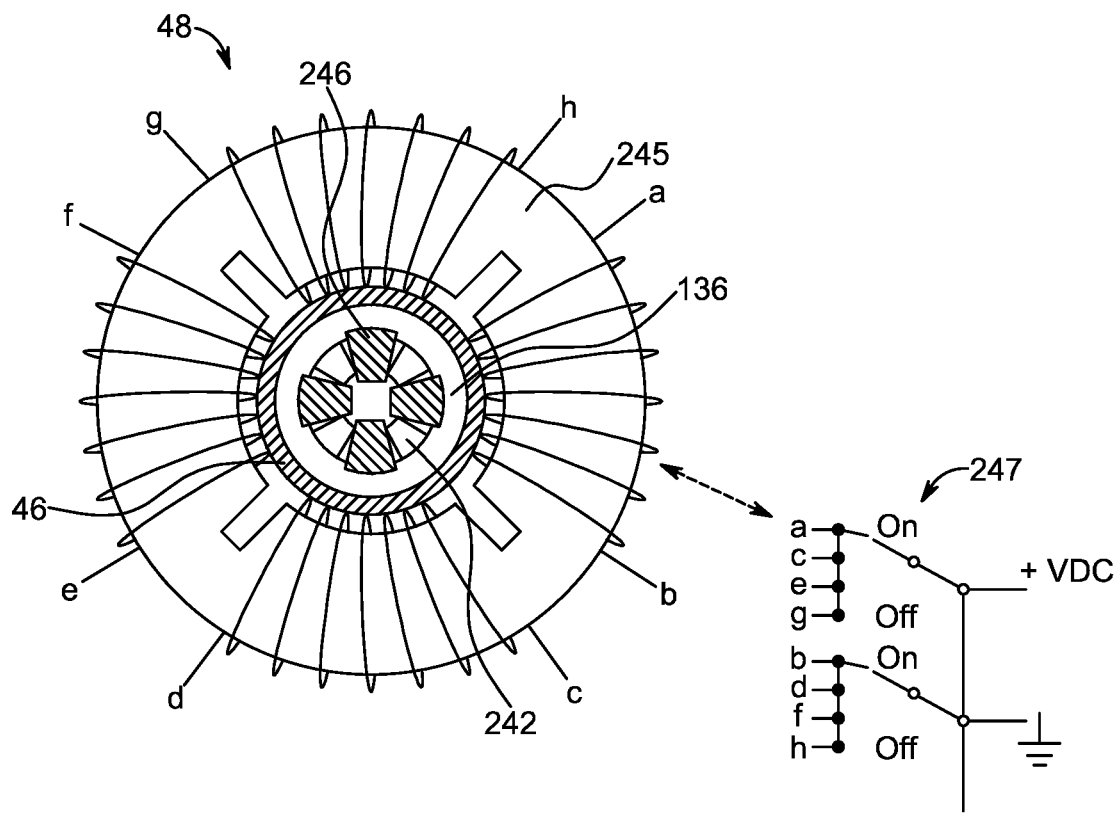
FIG. 35 is a top cross-sectional view of a syringe and a piston having a syringe engagement mechanism in accordance with one example of the present disclosure.

With reference to FIG. 35, an engagement mechanism 48 of a piston (not shown) is shown in accordance with another example of the present disclosure. The engagement mechanism 48 is configured for releasably connecting the engagement portion 46 of a syringe with the piston. In one example, the engagement mechanism 48 includes an outer ring 245 and an inner ring 242. When interlocked with the engagement portion 46 of the syringe, the inner ring 242 is received in an opening 136 of the engagement portion 46, while the outer ring 245 is positioned around the outer diameter of the engagement portion 46. In some examples, the outer ring 245 is an electromagnet. In some examples, the inner ring 242 includes a plurality of sliding, ferromagnetic clamps 246. A switch 247 is connected (either directly or wirelessly) to the outer ring 245. When the switch 247 is positioned in an off position, the engagement mechanism 48 is inactive. After the engagement mechanism 48 has been inserted into the engagement portion 46, the switch 247 can be moved to an on position. When the switch 247 is activated, the electromagnet of the outer ring 245 activates the ferromagnetic clamps 246 of the inner ring 242, such that the clamps 246 are attracted/moved towards the outer ring 245, thereby clamping the engagement portion 46 of the syringe between the inner ring 242 and the outer ring 245. After the engagement portion 46 has been engaged with the engagement mechanism 48, the piston can be moved in a proximal direction to fill the interior of the syringe with fluid or in the distal direction to deliver the fluid from the interior of the syringe. To release the engagement mechanism 48 from the engagement portion 46, the switch 247 is turned to the off position to deactivate the electromagnet of the outer ring 245 to unclamp the inner ring 242.

While examples of a fluid delivery system and a syringe for use therefor were provided in the foregoing description, those skilled in the art may make modifications and alterations to these examples without departing from the scope and spirit of the disclosure. Accordingly, the foregoing description is intended to be illustrative rather than restrictive. The disclosure described hereinabove is defined by the appended claims, and all changes to the disclosure that fall within the meaning and the range of equivalency of the claims are to be embraced within their scope.

We claim:

1. An engagement mechanism configured to be associated with a reciprocally movable piston of a fluid injector and configured for releasably engaging an engagement portion either at a proximal end of a plunger in a syringe or extending from a proximal end wall of a rolling diaphragm syringe, the engagement mechanism comprising:
   a plurality of engagement elements reversibly and radially movable relative to the engagement portion between a first position, where the plurality of engagement elements are disengaged from the engagement portion, and a second position, where the plurality of engagement elements are engaged with the engagement portion; and
   a drive mechanism for moving the plurality of engagement elements between the first position and the second position,
   wherein the plurality of engagement elements are progressively movable from the first position to the second position with a movement of the reciprocally movable piston in a proximal direction to continuously increase a gripping force on the engagement portion.

2. The engagement mechanism of claim 1, wherein the drive mechanism is configured to be operatively connected to the reciprocally movable piston such that the plurality of engagement elements are movable from the first position to the second position with the movement of the reciprocally movable piston in the proximal direction.

3. The engagement mechanism of claim 1, wherein the plurality of engagement elements are movable from the second position to the first position with a movement of the reciprocally movable piston in a distal direction.

4. The engagement mechanism of claim 1, wherein the drive mechanism moves the plurality of engagement elements between the first position and the second position independently of the movement of the reciprocally movable piston in the proximal direction or a movement of the reciprocally movable piston in a distal direction.

5. The engagement mechanism of claim 1, wherein the drive mechanism comprises at least one of the following: a linear electric motor or actuator, a rotary electric motor or actuator, a solenoid, a pneumatic mechanism, a hydraulic mechanism, an electromagnetic mechanism, an electroactive polymer mechanism, a nitinol wire-based mechanism, and any combination thereof.

6. The engagement mechanism of claim 1, wherein the drive mechanism comprises a rod linearly or rotatably movable by a motor, and wherein linear or rotary movement of the rod reversibly moves the plurality of engagement elements between the first position and the second position.

7. The engagement mechanism of claim 1, wherein the drive mechanism comprises:
    an outer piston sleeve fixed relative to the reciprocally movable piston of the fluid injector;
    an abutment section movably received within the outer piston sleeve at a distal end of the outer piston sleeve, wherein the abutment section is operatively engaged with the plurality of engagement elements; and
    an inner piston sleeve movably received within the outer piston sleeve and connected with the abutment section such that movement of the inner piston sleeve causes movement of the abutment section, wherein the inner piston sleeve is movable by a piston rod movably coupled to the reciprocally movable piston,
    wherein the movement of the reciprocally movable piston in the proximal direction moves the outer piston sleeve proximally relative to the abutment section, and
    wherein proximal movement of the outer piston sleeve relative to the abutment section moves the plurality of engagement elements from the first position to the second position.

8. The engagement mechanism of claim 7, wherein the abutment section has an outer engagement surface configured for contacting the proximal end of the plunger or the proximal end wall of the rolling diaphragm syringe and a central opening on the outer engagement surface configured for receiving the engagement portion.

9. The engagement mechanism of claim 1, wherein each of the plurality of engagement elements is pivotally movable between the first position and the second position by rotation about a pivot pin.

10. The engagement mechanism of claim 1, wherein each of the plurality of engagement elements is movable between the first position and the second position by movement of a pin along an inclined ramp.

11. The engagement mechanism of claim 1, wherein each of the plurality of engagement elements is linearly movable between the first position and the second position in a radially inward or outward direction relative to a longitudinal axis of the reciprocally movable piston.

12. The engagement mechanism of claim 1, wherein the plurality of engagement elements are biased to the first position by a biasing mechanism.

13. A fluid injector comprising:
    at least one injector head comprising at least one reciprocally movable piston;
    an engagement mechanism associated with the at least one reciprocally movable piston and configured for releasably engaging an engagement portion at either a proximal end of a plunger in a syringe or extending from a proximal end wall of a rolling diaphragm syringe, the engagement mechanism comprising:
        a plurality of engagement elements reversibly and radially movable relative to the engagement portion of either the syringe or the rolling diaphragm syringe between a first position, where the plurality of engagement elements are disengaged from the engagement portion of either the syringe or the rolling diaphragm syringe, and a second position, where the plurality of engagement elements are engaged with the engagement portion of either the syringe or the rolling diaphragm syringe; and
        a drive mechanism for moving the plurality of engagement elements between the first position and the second position,
        wherein the plurality of engagement elements are progressively movable from the first position to the second position with a movement of the at least one reciprocally movable piston in a proximal direction to continuously increase a gripping force on the engagement portion.

14. The fluid injector of claim 13, wherein the drive mechanism is operatively connected to the at least one reciprocally movable piston such that the plurality of engagement elements are movable from the first position to the second position with the movement of the at least one reciprocally movable piston in the proximal direction.

15. The fluid injector of claim 13, wherein the plurality of engagement elements are movable from the second position to the first position with a movement of the at least one reciprocally movable piston in a distal direction.

16. The fluid injector of claim 13, wherein the drive mechanism comprises at least one of the following a linear electric motor or actuator, a rotary electric motor or actuator, a solenoid, a pneumatic mechanism, a hydraulic mechanism, an electromagnetic mechanism, an electroactive polymer mechanism, a nitinol wire-based mechanism, and any combination thereof.

17. The fluid injector of claim 13, wherein the drive mechanism comprises a rod linearly or rotatably movable by a motor, and wherein linear or rotary movement of the rod reversibly moves the plurality of engagement elements between the first position and the second position.

18. The fluid injector of claim 13, wherein each of the plurality of engagement elements is pivotally movable between the first position and the second position by rotation about a pivot pin.

19. The fluid injector of claim 13, wherein each of the plurality of engagement elements is linearly movable between the first position and the second position in a radially inward or outward direction relative to a longitudinal axis of the at least one reciprocally movable piston.

20. The engagement mechanism of claim 13, wherein the plurality of engagement elements are biased to the first position by a biasing mechanism.

\* \* \* \* \*